(12) United States Patent
Yonishi et al.

(10) Patent No.: US 7,407,961 B2
(45) Date of Patent: Aug. 5, 2008

(54) PYRAZINE DERIVATIVES AND PHARMACEUTICAL USE THEREOF

(75) Inventors: Satoshi Yonishi, Osaka (JP); Satoshi Aoki, Osaka (JP); Yuji Matsushima, Osaka (JP); Atsushi Akahane, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 495 days.

(21) Appl. No.: 10/972,340

(22) Filed: Oct. 26, 2004

(65) Prior Publication Data

US 2005/0113387 A1 May 26, 2005

(30) Foreign Application Priority Data

Oct. 27, 2003 (AU) .............................. 2003905895
May 24, 2004 (AU) .............................. 2004902764

(51) Int. Cl.
*A61K 31/4965* (2006.01)
*C07D 401/00* (2006.01)
*C07D 403/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)

(52) U.S. Cl. ................................. 514/255.05; 544/405
(58) Field of Classification Search ............ 514/255.05; 544/405
See application file for complete search history.

(56) References Cited

U.S. PATENT DOCUMENTS 6,673,802 B2 * 1/2004 Castelhano et al. ...... 514/263.2
6,995,161 B2 * 2/2006 Yoon et al. ............. 514/255.06

OTHER PUBLICATIONS

Parry et al, "Functionalized Pyridylboronic Acids and Their Suzuki Cross-Coupling Reactions to Yield Novel Heteorarylpyridines" Journal Organic Chemistry, vol. 67, pp. 7541-7543 (2002).*
Popoli et al, "Adenosine A2a Receptor Antagonism and Neuroprotection: Mechanisms, Lights, and Shadows" Critical Reviews in Neurobiology, vol. 16(1&2), pp. 99-106 (2004).*
Fredholm and Svenningsson, "Adenosine-dopamine interactions: Development of a concept and some comments on therapeutic possibilities" Neurology, vol. 61 (Suppl. 6), pp. S5-S9 (2003).*
Maemoto et al, "Pharmacological Characterization of FR194921, a New, Potent, Selective, and Orally Active Antagonist for Central Adenosine A1 Receptors" Journal of Pharmacological Science, vol. 96, pp. 42-52 (2004).*
Pitsikas and Borsini, "The Adenosine A1 Receptor Antagonist BIIP 20 Counteracts Scopolamine-Induced Behavioral Deficits in the Passive Avoidance Task in the Rat" European Journal of Pharmacology, vol. 328, pp. 19-22 (1997).*
Yacoubi et al, "Adenosine A2A receptor antagonists are potential antidepressants: evidence based on pharmacology and A2A knockout mice." British Journal of Pharmacology, vol. 134, pp. 68-77 (2001).*
Chen et al, "A2A Adenosine Receptor Deficiency Attenuates Brain Injury Induced by Transient Focal Ischemia in Mice" The Journal of Neuroscience, vol. 19(21), pp. 9192-9200 (1999).*
Monopoli et al, "Blockade of adenosine A2A receptors by SCH 58261 results in neuroprotective effects in cerebral ischaemia in rats" Neuroreport, vol. 9, pp. 3955-3959 (1998).*
Ledent et al, "Aggressiveness, hypoalgesia and high blood pressure in mice lacking the adenosine A2a receptor" Nature, vol. 388, pp. 674-678 (2004).*

* cited by examiner

*Primary Examiner*—Zachary C Tucker
(74) *Attorney, Agent, or Firm*—Oblon, Spivak, McClelland, Maier & Neustadt, P.C.

(57) ABSTRACT

A pyrazine derivative of the following formula (I):

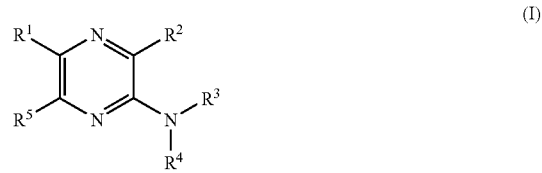

or a salt thereof.

The pyrazine compound (I) and a salt thereof of the present invention are adenosine antagonists and are useful for the prevention and/or treatment of depression, dementia (e.g. Alzheimer's disease, cerebrovascular dementia, dementia accompanying Parkinson's disease, etc.), Parkinson's disease, anxiety, pain, cerebrovascular disease (e.g. stroke, etc.), heart failure and the like.

14 Claims, No Drawings

PYRAZINE DERIVATIVES AND PHARMACEUTICAL USE THEREOF

TECHNICAL FIELD

The present invention relates to a novel pyrazine derivative and a salt thereof, which are useful as medicaments.

BACKGROUND ART

Adenosine is a ubiquitous biochemical messenger. Adenosine binds to and activates seven-transmembrane spanning G-protein coupled receptors, eliciting a variety of physiological responses. Adenosine receptors are divided into four known subtypes (i.e., $A_1$, $A_{2a}$, $A_{2b}$, and $A_3$). These receptor subtypes mediate different, and sometimes opposing, effects. Activation of the adenosine $A_1$ receptor, for example, elicits an increase in renal vascular resistance, while activation of the adenosine $A_{2a}$ receptor elicits a decrease in renal vascular resistance. Accordingly, adenosine antagonists are useful in the prevention and/or treatment of numerous diseases, including cardiac and circulatory disorders, degenerative disorders of the central nervous system, respiratory disorders, and many diseases for which diuretic treatment is suitable.

Some 2-aminopyridine compounds to exhibit adenosine receptor antagonism are known (WO 02/14282, WO 01/25210, etc.), and some 2-aminopyrimidine compounds are also known (US 2001/0027196, etc.).

However, it is generally difficult to produce a pyrazine which is substituted by four different substituents, and for example the synthesis of a pyrazine compound of the formula A:

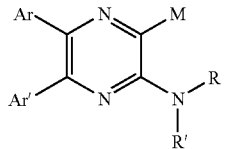

(A)

wherein Ar and Ar' are independently same or different aryl; and

R, R' and M are independently hydrogen or suitable substituent;

is reported (e.g. (1) *J. Org. Chem.*, 40, 2341 (1975), (2) *J. Heterocyclic Chem.*, 15, 665 (1978), (3) *J. Chem. Soc., Perkin Trans.* 1, 885 (1994), (4) *Synthesis*, 931 (1994), (5) WO-02/088084, etc.), however the Ar and Ar' thereof are same, and the selective synthesis of a pyrazine compound A wherein Ar and Ar' are different is not shown as far as we know, and 2-amino-6-aryl-5-(6-oxo-1,6-dihydro-pyrid-3-yl)-pyrazine compounds and derivatives thereof are novel, so there has been no knowledge about these compounds, so far. In addition, any pyrazine derivatives having both of adenosine $A_1$ and $A_{2a}$ inhibitory activities are not known.

DISCLOSURE OF INVENTION

The present invention relates to a novel pyrazine derivative and a pharmaceutically acceptable salt thereof, which are useful as medicaments with no or less toxicity (particularly the convulsive toxicity); processes for preparing the preparation of pyrazine derivative and a salt thereof; a pharmaceutical composition comprising, as an active ingredient, said pyrazine derivative or a pharmaceutically acceptable salt thereof; a use of said pyrazine derivative or a pharmaceutically acceptable salt thereof as a medicament; and a method for using said pyrazine derivative or a pharmaceutically acceptable salt thereof for therapeutic purposes, which comprises administering said pyrazine derivative or a pharmaceutically acceptable salt thereof to a human being or an animal.

The pyrazine derivatives and a salt thereof are adenosine antagonists (especially, $A_1$ receptor and $A_2$ (particularly $A_{2a}$) receptor dual antagonists) and possess various pharmacological actions such as anticatalepsy action, cognitive enhancing action, analgesic action, locomotor action, antidepressant action, diuretic action, cardioprotective action, cardiotonic action, vasodilating action (e.g. cerebral vasodilating action, etc.), the action of increasing the renal blood flow, renal protective action, improvement action of renal function, enhancing action of lipolysis, inhibition action of anaphylactic bronchoconstriction, acceleration action of the insulin release, the action of increasing the production of erythropoietin, inhibiting action of platelet aggregation, or the like.

They are useful as cognitive enhancer, antianxiety drug, antidementia drug, psychostimulant, analgesic, cardioprotective agent, antidepressant, ameliorants of cerebral circulation, tranquilizer, drug for heart failure, cardiotonic agent, antihypertensive agent, drug for renal failure (renal insufficiency), drug for renal toxicity, renal protective agent, drug for improvement of renal function, diuretic, drug for edema, antiobesity, antiasthmatic, bronchodilator, drug for apnea, drug for gout, drug for hyperuricemia, drug for sudden infant death syndrome (SIDS), ameliorants of immunosuppressive action of adenosine, antidiabetic agent, drug for ulcer, drug for pancreatitis, drug for Meniere's syndrome, drug for anemia; drug for thrombosis, drug for myocardial infarction, drug for obstruction, drug for arteriosclerosis obliterans, drug for thrombophlebitis, drug for cerebral infarction, drug for transient ischemic attack, drug for angina pectoris, or the like; and useful for the prevention and/or treatment of depression, dementia (e.g. Alzheimer's disease, cerebrovascular dementia, dementia accompanying Parkinson's disease, etc.), Parkinson's disease, anxiety, pain, cerebrovascular disease (e.g. stroke, etc.), heart failure; hypertension (e.g. essential hypertension, nephrogenous hypertension, etc.); circulatory insufficiency (acute circulatory insufficiency) caused by, for example, ischemia/reperfusion injury (e.g. myocardial ischemia/reperfusion injury, cerebral ischemia/reperfusion injury, peripheral ischemia/reperfusion injury, etc.), shock (e.g. endotoxin shock, hemorrhagic shock, etc.), surgical procedure, or the like; post-resuscitation asystole; bradyarrhythmia; electro-mechanical dissociation; hemodynamic collapse; SIRS (systemic inflammatory response syndrome); multiple organ failure; renal failure (renal insufficiency) (e.g. acute renal failure, etc.), renal toxicity [e.g. renal toxicity induced by a drug such as cisplatins, gentamicin, FR-900506 (disclosed in EP-0184162), cyclosporin (e.g. cyclosporin A) or the like; glycerol, etc.], nephrosis, nephritis, edema (e.g. cardiac edema, nephrotic edema, hepatic edema, idiopathic edema, drug edema, acute angioneurotic edema, hereditary angioneurotic edema, carcinomatous ascites, gestational edema, etc.); obesity, bronchial asthma, gout, hyperuricemia, sudden infant death syndrome, immunosuppression, diabetes, ulcer such as peptic ulcer (e.g. gastric ulcer, duodenal ulcer, etc.), pancreatitis, Meniere's syndrome, anemia, dialysis-induced hypotension, constipation, ischemic bowel disease, ileus (e.g. mechanical ileus, adynamic ileus, etc.); and myocardial infarction, thrombosis (e.g. arterial thrombosis, cerebral thrombosis, etc.), obstruction, arteriosclerosis obliterans, thrombophlebitis, cerebral infarction, transient ischemic attack, angina pectoris, or the like.

The novel pyrazine derivative or a salt thereof of the present invention can be shown by the following formula (I):

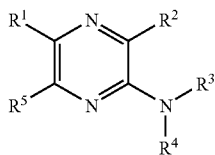

(I)

wherein
R¹ is

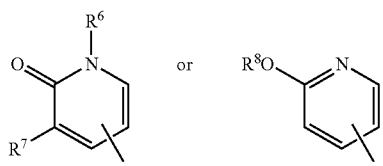

wherein
R⁶ is hydrogen, or optionally substituted lower alkyl;
R⁷ is hydrogen or halogen;
R⁸ is lower alkyl;
R² is hydrogen; hydroxy; halogen; cyano; or lower alkyl, lower alkenyl, lower alkynyl, lower alkoxy, aryloxy, arylthio, acyl, aryl, heterocyclic group or amino, each of which is optionally substituted by substituent(s);
R³ and R⁴ are independently hydrogen, lower alkyl or acyl; and
R⁵ is lower alkyl, lower alkenyl, lower alkynyl, cyano, aryl or heterocyclic group, each of which is optionally substituted by substituent(s);

or a salt thereof.

The preferred embodiments of the pyrazine compound of the present invention represented by the general formula (I) are as follows.

(1) The pyrazine compound of the general formula (I)
wherein
R¹ is

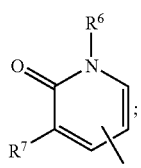

wherein
R⁶ is hydrogen, lower alkyl, aryl(lower)alkyl, heteroaryl (lower)alkyl;
R⁷ is hydrogen or halogen;
R² is hydrogen, halogen, cyano, optionally substituted lower alkyl, optionally substituted lower alkynyl, lower alkoxy, aryloxy, arylthio, carbamoyl, carboxy, protected carboxy or optionally substituted amino;
R³ and R⁴ are independently hydrogen or lower alkyl; and
R⁵ is aryl or heteroaryl each of which is optionally substituted by one or more substituent(s);

or a salt thereof.

(2) The pyrazine compound of (1) above
wherein
R² is hydrogen, halogen, cyano, hydroxylated(lower)alkyl, lower alkynyl, lower alkoxy, aryloxy, arylthio, carboxy, esterified carboxy, carbamoyl, amidated carboxy, amino or mono- or di-(lower)alkylamino;
R³ and R⁴ are independently hydrogen;
R⁵ is aryl or heteroaryl, each of which is optionally substituted by one or more substituent (s) selected from the group consisting of halogen and lower alkoxy;
R⁶ is hydrogen or lower alkyl; and
R⁷ is hydrogen;

or a salt thereof.

(3) The pyrazine compound of (2) above
wherein
R² is hydrogen, bromo, cyano, hydroxymethyl, hydroxyethyl, hydroxypropyl, ethynyl, methoxy, ethoxy, propoxy, phenyloxy, phenylthio, carboxy, carbamoyl, mono- or di-methylaminocarbonyl, pyridylmethylaminocarbonyl, hydroxymethylaminocarbonyl or mono- or di-methylamino;
R³ and R⁴ are independently hydrogen;
R⁵ is phenyl, pyridyl, furyl, thienyl, pyrrolyl or pyrazolyl, each of which is optionally substituted by one or more substituent(s) selected from the group consisting of fluoro, chloro and methoxy;
R⁶ is hydrogen, methyl, ethyl, n-propyl, isopropyl, n-butyl or t-butyl; and
R⁷ is hydrogen;

or a salt thereof.

(4) The pyrazine compound of (3) above
wherein
R² is hydrogen, cyano, ethynyl, methoxy, phenyloxy, phenylthio, carboxy, carbamoyl or methylamino; and
R⁵ is phenyl, furyl or thienyl, each of which is optionally substituted by one or more substituent (s) selected from the group consisting of fluoro, chloro and methoxy;

or a salt thereof.

(5) The pyrazine compound of (4) above
wherein
R² is hydrogen, cyano, carboxy, carbamoyl or methylamino;
R⁵ is phenyl which is optionally substituted by one or more fluoro; and
R⁶ is hydrogen, methyl, ethyl or isopropyl;

or a salt thereof.

The object compound (I) and a salt thereof of the present invention can be prepared by the following processes.

Process 1

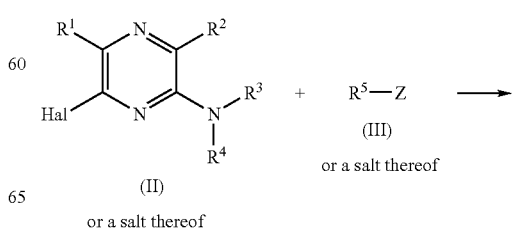

-continued
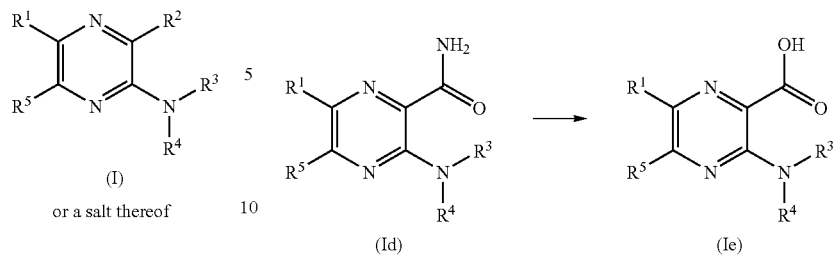
(I)
or a salt thereof
Process 2
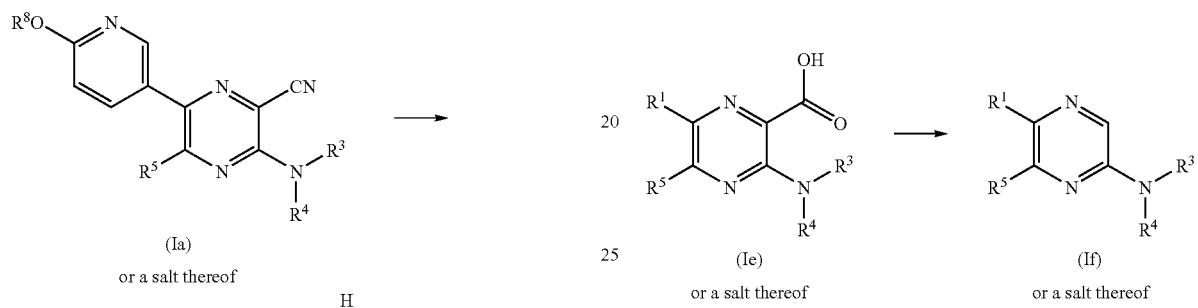
Process 3
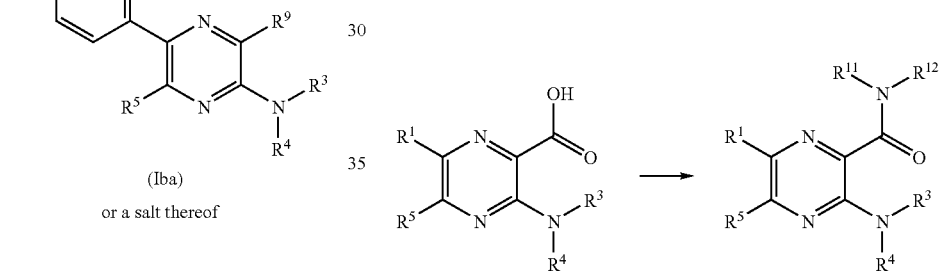
Process 4
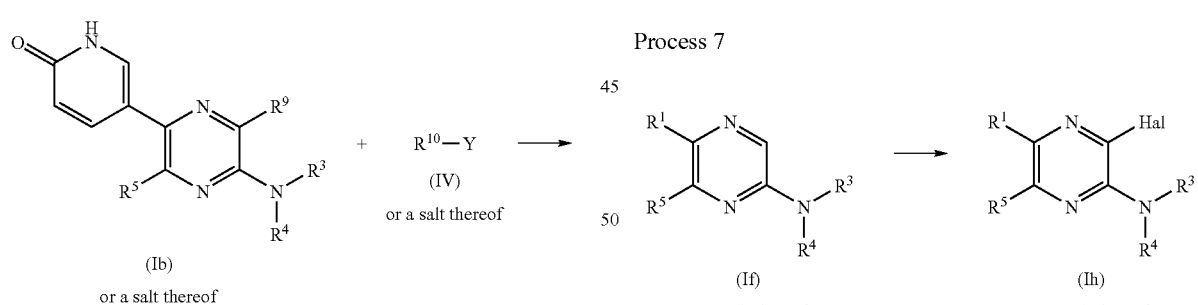
Process 5
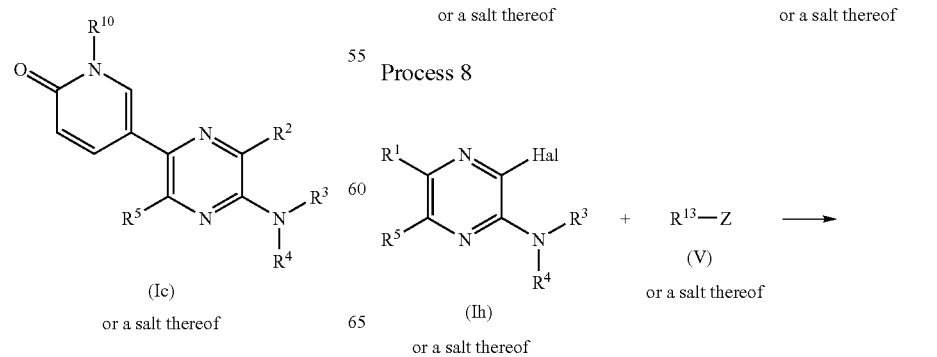

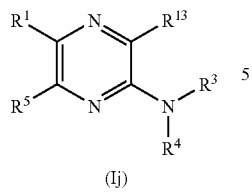

(Ij)

or a salt thereof

[wherein $R^1$, $R^2$, $R^3$, $R^4$, $R^5$ and $R^8$ are each as defined above;
$R^9$ is cyano, carbamoyl or carboxy;
$R^{10}$ is optionally substituted lower alkyl;
$R^{11}$ and $R^{12}$ are independently hydrogen, lower alkyl, lower alkoxy or cyclo(lower)alkyl, each of which is optionally substituted by substituent(s); or $R^{11}$ and $R^{12}$, together with the nitrogen atom to which they are attached, represent a optionally substituted N-containing heterocyclic group;
$R^{13}$ is lower alkyl, lower alkenyl, lower alkynyl, lower alkoxy, aryloxy, arylthio, acyl, aryl, heterocyclic group or amino, each of which is optionally substituted by substituent(s);
Y is a leaving group;
Hal is a halogen atom; and
Z is hydrogen, an alkali metal (e.g. lithium, sodium, potassium, etc.), $SnBu_3$, $BW_2$ or Met-Hal;
  wherein $BW_2$ is a part of organoboron compound such as $B(OH)_2$, $B(CHCH_3CH(CH_3)_2)_2$, tetramethyl-1,3,2-dioxaborolan-2-yl, 9-borabicyclo[3.3.1]nonanyl, or the like; and
  Met-Hal is a part of metal halide compound such as MgBr, ZnCl, or the like.

The starting compounds or a salt thereof can be prepared, for example, by the following reaction schemes.

Process A

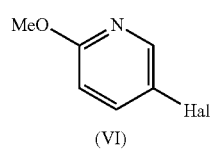

(VI)

or a salt thereof

Step 1

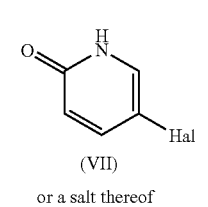 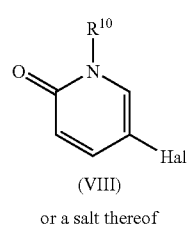

(VII)       (IV)       (VIII)
or a salt thereof  or a salt thereof  or a salt thereof Step 2
$R^{10}-Y$ Process B $R^1 \diagdown Hal$  Step 1  →  $R^1 \diagdown \diagup$  Step 2  →
(IX)                            ∥
or a salt thereof              O
                               (X)
                          or a salt thereof -continued

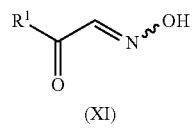

(XI)

or a salt thereof

Process C $R^1 \diagdown \diagup \diagdown N\diagdown OH$    aminomalonitrile
      ∥                         ─────────────→
      O                         or a salt thereof (XI)

or a salt thereof (XII)

or a salt thereof

Process D

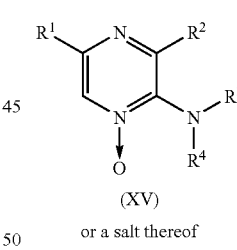

(XIII)         (XIV)
or a salt thereof  or a salt thereof

Process E (XV) + $PO(Hal)_3$ →
(XVI)
or a salt thereof or a salt thereof (II)

or a salt thereof

[wherein $R^1$, $R^2$, $R^3$, $R^4$, $R^{10}$, Y and Hal are each as defined above.]

In addition to the processes as mentioned above, the object compound (I) and a salt thereof can be prepared, for example, according to the procedures as illustrated in Examples in the present specification or in a manner similar thereto.

The starting compounds can be prepared, for example, according to the procedures as illustrated in Preparations in the present specification or in a manner similar thereto.

The object compound (I) and a salt thereof can be prepared according to the methods as shown in Preparations or Examples, or in a manner similar thereto.

It is also to be noted that the solvating form of the compound (I) (e.g. hydrate, etc.) and any form of the crystal of the compound (I) are included within the scope of the present invention.

It is also to be noted that radiolabelled derivatives of the compound (I), which are suitable for biological studies, are included within the scope of the present invention.

Suitable salts of the object compound (I) are conventional pharmaceutically acceptable ones and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, fumarate, methanesulfonate, benzenesulfonate, formate, toluenesulfonate, etc.), an inorganic acid salt (e.g. hydrochloride, hydrobromide, hydriodide, sulfate, phosphate, etc.), a salt with an amino acid (e.g. arginine, aspartic acid, glutamic acid, etc.), and the like.

Suitable examples and illustrations of the various definitions which the present invention includes within the scope thereof and which appear in the above and following description in the present specification are explained in detail as follows.

The term "optionally substituted" refers to "unsubstituted or substituted".

The term "lower" is intended to mean 1 to 6 carbon atom(s) unless otherwise indicated.

Suitable "lower alkyl" and "(lower)alkyl" moiety in the term of "mono- or di-(lower)alkylamino" may include straight or branched ones such as methyl, ethyl, propyl, isopropyl, butyl, tert-butyl, pentyl, hexyl or the like, in which the preferred one may be methyl, ethyl or isopropyl.

Suitable "optionally substituted lower alkyl" may include lower alkyl which is optionally substituted by suitable substituent(s) such as lower alkoxy, hydroxy, aryloxy, cyclo(lower)alkyl, amino, aryl, heterocyclic group, acyl or the like.

Suitable "lower alkoxy" may include straight or branched ones such as methoxy, ethoxy, propoxy, isopropoxy, butoxy, tert-butoxy, pentyloxy, hexyloxy or the like.

Suitable "optionally substituted lower alkoxy" may include lower alkoxy which is optionally substituted by suitable substituent(s) such as hydroxy, cyclo(lower)alkyl, amino, aryl, heterocyclic group, acyl or the like.

Suitable "cyclo(lower)alkyl" may be cyclo(C3-C8)alkyl such as cyclopropyl, cyclobutyl, cyclopentyl, cyclohexyl, cycloheptyl, cyclooctyl or the like, in which the preferred one may be cyclohexyl.

Suitable "lower alkenyl" may include straight or branched ones such as vinyl, propenyl, allyl, isopropenyl, butenyl, pentenyl, hexenyl or the like, in which the preferred one may be vinyl.

Suitable "optionally substituted lower alkenyl" may include lower alkenyl which is optionally substituted by suitable substituent(s) such as lower alkoxy, hydroxy, cyclo(lower)alkyl, amino, aryl, heterocyclic group, acyl or the like.

Suitable "lower alkynyl" may include straight or branched ones such as ethynyl, propynyl, butynyl, pentynyl, hexynyl or the like, in which the preferred one may be ethynyl.

Suitable "optionally substituted lower alkynyl" may include lower alkynyl which is optionally substituted by suitable substituent(s) such as lower alkoxy, hydroxy, cyclo(lower)alkyl, amino, aryl, heterocyclic group, acyl or the like.

Suitable "aryl" and "aryl" moiety in the term of "aryloxy" or "arylthio" may include phenyl, naphthyl, indenyl, anthryl, or the like, in which the preferred one may be (C6-C10)aryl, and the more preferred one may be phenyl.

Suitable "aryl(lower)alkyl" may include phenyl(lower)alkyl (e.g. benzyl, phenethyl, etc.), diphenyl(lower)alkyl (e.g. benzhydryl, etc.), triphenyl(lower)alkyl (e.g. trityl, etc.), naphthyl(lower)alkyl, indenyl(lower)alkyl or anthryl(lower)alkyl and the like, in which the preferred one may be phenyl(lower)alkyl, and the more preferred one may be phenyl(C1-C4)alkyl.

Suitable "optionally substituted aryl" may include aryl which is optionally substituted by suitable substituent(s), preferably 1 to 3 substituent(s), such as lower alkyl, lower alkoxy, hydroxy, halogen, etc. Suitable examples of optionally substituted aryl include lower alkylphenyl, lower alkoxyphenyl and halophenyl.

Suitable "heterocyclic group" may be saturated or unsaturated monocyclic or polycyclic heterocyclic groups containing at least one heteroatom selected from among oxygen, sulfur and nitrogen.

The particularly preferred example of said heterocyclic group may include 3-through 8-membered unsaturated heteromonocyclic groups containing 1 through 4 nitrogen atom(s), such as pyrrolyl, pyrrolinyl, imidazolyl, pyrazolyl, pyridyl and its N-oxide, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), dihydrotriazinyl (e.g. 4,5-dihydro-1,2,4-triazinyl, 2,5-dihydro-1,2,4-triazinyl, etc.), etc.;

3-through 8-membered saturated heteromonocyclic groups containing 1 through 4 nitrogen atom(s), such as azetidinyl, pyrrolidinyl, imidazolidinyl, piperidyl (e.g. piperidino, etc.), piperazinyl, etc.;

unsaturated condensed heterocyclic groups containing 1 through 5 nitrogen atom(s), such as indolyl, isoindolyl, indolizinyl, benzimidazolyl, quinolyl, isoquinolyl, indazolyl, benzotriazolyl, tetrazolopyridyl, tetrazolopyridazinyl (e.g. tetrazolo[1,5-b]pyridazinyl etc.), dihydrotriazolopyridazinyl, etc.;

3-through 8-membered unsaturated heteromonocyclic groups containing 1 or 2 oxygen atoms and 1 through 3 nitrogen atom(s), such as oxazolyl, isoxazolyl, oxadiazolyl (e.g. 1,2,4-oxadiazolyl, 1,3,4-oxadiazolyl, 1,2,5-oxadiazolyl, etc.), etc.;

3-through 8-membered saturated heteromonocyclic groups containing 0.1 or 2 oxygen atom(s) and 1 through 3 nitrogen atoms, such as morpholinyl, oxazolidinyl (e.g. 1,3-oxazolidinyl etc.), etc.;

unsaturated condensed heterocyclic groups containing 1 or 2 oxygen atom(s) and 1 through 3 nitrogen atom(s), such as benzoxazolyl, benzoxadiazolyl, etc.;

3-through 8-membered unsaturated heteromonocyclic groups containing 1 or 2 sulfur atom(s) and 1 through 3 nitrogen atom(s), such as thiazolyl, isothiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl), etc.;

3-through 8-membered saturated heteromonocyclic groups containing 1 or 2 sulfur atom(s) and 1 through 3 nitrogen atom(s), such as thiazolidinyl etc.;

3-through 8-membered unsaturated heteromonocyclic groups containing 1 sulfur atom, such as thienyl etc.;

unsaturated condensed heterocyclic groups containing 1 or 2 sulfur atoms and 1 through 3 nitrogen atom(s), such as benzothiazolyl, benzothiadiazolyl, etc.;

3-through 8-membered unsaturated heteromonocyclic groups containing 1 or 2 oxygen atom(s), such as furyl, pyranyl, dioxolyl, etc.;

3-through 8-membered saturated heteromonocyclic groups containing 1 or 2 oxygen atom(s), such as oxolanyl, tetrahydropyranyl (e.g. tetrahydro-2H-pyran-2-yl etc.), dioxolanyl, etc.; and unsaturated condensed heterocyclic groups containing 1 or 2 oxygen atom(s), such as isobenzofuranyl, chromenyl (e.g. 2H-chromen-3-yl etc.), dihydrochromenyl (e.g. 3,4-dihydro-2H-chromen-4-yl etc.), etc.

Suitable "optionally substituted heterocyclic group" may include heterocyclic group which is optionally substituted by suitable substituent(s), preferably 1 to 3 substituent(s), such as lower alkyl, lower alkoxy, hydroxy, halogen, or the like.

Suitable "N-containing heterocyclic group" may be aforesaid "heterocyclic group", in which said group contains at least one N atom in its ring members, such as pyrrolyl, pyrrolinyl, imidazolyl, pyrazolyl, triazolyl, tetrazolyl, dihydrotriazinyl, azetidinyl, pyrrolidinyl, imidazolidinyl, piperidyl, piperazinyl, indolyl, isoindolyl, indazolyl, benzotriazolyl, dihydrotriazolopyridazinyl, morpholinyl, oxazolidinyl, thiazolynyl, thiazolidinyl, etc.

Suitable "heteroaryl" and "heteroaryl" moiety in the term of "heteroaryl(lower)alkyl" may be aforesaid "heterocyclic group", in which those categorized as an aromatic heterocyclic group, such as pyrrolyl, pyrrolinyl, imidazolyl, pyrazolyl, pyridyl, pyrimidinyl, pyrazinyl, pyridazinyl, triazolyl, tetrazolyl, dihydrotriazinyl, indolyl, isoindolyl, indolizinyl, benzimidazolyl, quinolyl, isoquinolyl, indazolyl, benzotriazolyl, tetrazolopyridyl, tetrazolopyridazinyl, dihydrotriazolopyridazinyl, oxazolyl, isoxazolyl, oxadiazolyl, benzoxazolyl, benzoxadiazolyl, thiazolyl, isothiazolyl, thiazolinyl, thiadiazolyl, thienyl, benzothiazolyl, benzothiadiazolyl, furyl, pyranyl, dioxolyl, isobenzofuranyl, chromenyl, dihydrochromenyl, etc.

Suitable "acyl" may include lower alkanoyl, aroyl, carboxy, protected carboxy, and the like.

Suitable examples of aforesaid "lower alkanoyl" may be formyl, acetyl, propionyl, butyryl, isobutyryl, pivaloyl, hexanoyl, or the like, in which the preferred one may be (C1-C4) alkanoyl.

Suitable examples of aforesaid "aroyl" may be benzoyl, toluoyl, or the like.

Suitable examples of aforesaid "protected carboxy" may be i) esterified carboxy, in which suitable esterified carboxy may include lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.), aryl(lower)alkoxycarbonyl (e.g. benzyloxycarbonyl, phenethyloxycarbonyl, 2-phenylpropoxycarbonyl, 4-phenylbutoxycarbonyl, 4-phenylpentyloxycarbonyl, 1,3-diphenylhexyloxycarbonyl, etc.), and the like;

ii) amidated carboxy, in which suitable amidated carboxy may include carbamoyl, N-(lower)alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc.), N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(t-butyl)carbamoyl, N-pentyl-N-hexylcarbamoyl, etc.], N-lower alkyl-N-aryl(lower)alkylcarbamoyl (e.g. N-methyl-N-benzylcarbamoyl, etc), and the like.

Suitable "halogen" may be fluoro, chloro, bromo and iodo.

Suitable "a leaving group" may include halogen, hydroxy, acyloxy such as alkanoyloxy (e.g. acetoxy, propionyloxy, etc.) or sulfonyloxy (e.g. mesyloxy, tosyloxy, etc.), or the like.

Suitable "optionally substituted amino" may include amino, mono- or di-(lower)alkylamino (e.g. methylamino, dimethylamino, methylethylamino, etc.), acylamino (e.g. lower alkoxycarbonylamino (e.g. methoxycarbonylamino, ethoxycarbonylamino, etc.), sulfonylamino (e.g. mesylamino, etc.), ureido, etc.), or the like.

The processes for preparing the object pyrazine compound (I) are explained in detail in the following.

Process 1

The compound (I) or a salt thereof can be prepared by subjecting the compound (II) or a salt thereof to coupling reaction with the compound (III) or a salt thereof.

This reaction is usually carried out in a conventional solvent such as water, acetone, dioxane, acetonitrile, 1,2-dimethoxyethane, chloroform, dichloromethane, 1,2-dichloroethane, tetrahydrofuran, ethyl acetate, N,N-dimethylformamide, methanol, ethanol, diethyl ether, 1,3-dimethyl-2-imidazolidinone, N-methylpyrrolidone, N,N'-dimethylpropyleneurea, a mixture thereof or any other organic solvent which does not adversely affect the reaction.

Some of the present reaction is preferably carried out in the presence of an organic or inorganic base such as an alkali metal (e.g. sodium, potassium, etc.), an alkaline earth metal (e.g. magnesium, calcium, etc.), the hydride or hydroxide or alkoxide or carbonate or hydrogencarbonate or alkanoic acid thereof, trialkylamine (e.g. triethylamine, trimethylamine, etc.), hydrazine, pyridine compound (e.g. pyridine, lutidine, picoline, 4-dimethylaminopyridine, etc.), quinoline, and the like.

Some of the present reaction is preferably carried out in the presence of a catalyst such as palladium(II) acetate, tetrakis(triphenylphosphine)palladium(0), and the like.

The reaction temperature is not critical, and the reaction is usually carried out at ambient temperature, under warming or heating.

Process 2

The compound (Iba) or a salt thereof can be prepared by subjecting the compound (Ia) or a salt thereof to hydrolysis.

This reaction is carried out in accordance with a conventional method.

The hydrolysis is preferably carried out in the presence of a base or an acid including Lewis acid.

Suitable base includes an inorganic base and an organic base such as an alkali metal (e.g. sodium, potassium, etc.), an alkaline earth metal (e.g. magnesium, calcium, etc.), the hydroxide or carbonate or hydrogencarbonate thereof, trialkylamine (e.g. triethylamine, trimethylamine, etc.), hydrazine, pyridine compound (e.g. pyridine, lutidine, picoline, 4-dimethylaminopyridine, etc.), 1,5-diazabicyclo[4.3.0]non-5-ene, quinoline, 1,4-aiazabicyclo[2.2.2]octane, 1,8-diazabicyclo[5.4.0]undec-7-ene, or the like.

Suitable acid includes an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, hydrogen chloride, hydrogen bromide, etc.).

The elimination using Lewis acid such as boron tribromide, boron trichloride, boron trifluoride, aluminum chloride or the like is preferably carried out in the presence of cation trapping agents (e.g. anisole, phenol, etc.).

The hydrolysis in this case usually carried out in the presence of an acid including Lewis acid, and these acid(s) including Lewis acid(s) can be used in the mixture, and the point(s) or the number of being hydrolyzed can be different by the condition (see the example part (examples 2, 7, 10 and 15) in detail).

The reaction is usually carried out in a solvent such as water, an alcohol (e.g. methanol, ethanol, isopropyl alcohol, etc.), tetrahydrofuran, dioxane, toluene, dichloromethane, 1,2-dichloroethane, chloroform, N,N-dimethylformamide, N,N-dimethylacetamide, or any other organic solvent which does not adversely affect the reaction, or a mixture thereof.

A liquid base or acid can be also used as the solvent.

The reaction temperature is not critical and the reaction is usually carried out under cooling to heating.

Process 3

The compound (Ic) or a salt thereof can be prepared by subjecting the compound (Ib) or a salt thereof to the alkylation with the compound (IV) or a salt thereof.

Suitable salt of the compound (IV) can be referred ones as exemplified for the compound (I).

This reaction is carried out in a solvent such as water, phosphate buffer, acetone, chloroform, acetonitrile, nitrobenzene, dichloromethane, 1,2-dichloroethane, formamide, N,N-dimethylformamide, methanol, ethanol, sec-butanol, amyl alcohol, diethyl ether, dioxane, 1,2-dimethoxyethane, tetrahydrofuran, dimethyl sulfoxide, or any other organic solvent which does not adversely affect the reaction, preferably in ones having strong polarities. Among the solvents, hydrophilic solvents may be used in a mixture with water. When the compound (IV) is in a liquid state, it can also be used as a solvent. The reaction is preferably conducted in the presence of a base, for example, inorganic base such as alkali metal hydroxide, alkali metal alkoxide (e.g. potassium t-butoxide), alkali metal carbonate, alkali metal bicarbonate, alkali metal hydride (e.g. sodium hydride, etc.), or organic base such as trialkylamine (e.g. triethylamine, etc.), or basic resin, and the like.

The reaction temperature is not critical, and the reaction is usually carried out at ambient temperature, under warming or heating.

The present reaction is preferably carried out in the presence of alkali metal halide (e.g. sodium iodide, potassium iodide, etc.), or the like.

When Y is —OH, activation of OH with triphenylphosphine, or the like, and di(lower)alkyl azodicarboxylate (e.g. diethyl azodicarboxylate, diisopropyl azodicarboxylate, etc.), or the like, may be necessary.

Process 4

The compound (Ie) or a salt thereof can be prepared by subjecting the compound (Id) or a salt thereof to hydrolysis using a base or an acid.

This reaction can be carried out in the same manner as the aforementioned hydrolysis using a base in Process 2, and therefore the reagents to be used and the reaction conditions (e.g., solvent, reaction temperature, etc.) can be referred to those of Process 2.

Process 5

The compound (If) or a salt thereof can be prepared by decarboxylation of the compound (Ie) or a salt thereof.

This reaction is carried out in accordance with a conventional method such as thermal decomposition, acid decomposition and the like; more suitable one in this case is thermal decomposition.

The reaction is usually carried out in a conventional inactive solvent such as quinoline, dichlorobenzene, mesitylene, dodecane, Dowtherm® (phenyl ether-biphenyl eutectic mixture) or any other organic solvent which does not adversely affect the reaction, or a mixture thereof; more suitable one in this case is 1,2-dichlorobenzene.

The reaction temperature is not critical, and the reaction is usually carried out on 100° C.-200° C. heating condition.

Process 6

The compound (Ig) or a salt thereof can be prepared by amidation of the compound (Ie) or a salt thereof.

The reaction is usually carried out in a conventional solvent such as water, acetone, dioxane, acetonitrile, chloroform, dichloromethane, 1,2-dichloroethane, tetrahydrofuran, ethyl acetate, N,N-dimethylformamide, pyridine or any other organic solvent which does not adversely affect the reaction, or a mixture thereof.

The reaction is preferably carried out in the presence of a conventional condensing agent such as N,N'-dicyclohexylcarbodiimide; N-cyclohexyl-N'-morpholinoethyl-carbodiimide; N-cyclohexyl-N'-(4-diethylaminocyclohexyl)-carbodiimide; N,N'-diisopropylcarbodiimide; N-ethyl-N'-(3-dimethylaminopropyl)carbodiimide; N,N-carbonyl-bis-(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazoblium hydroxide intramolecular salt; 1-(p-chlorobenzenesulfonyloxy)-6-chloro-1H-benzotriazole;

so-called Vilsmeier reagent prepared by the reaction of N,N-dimethylformamide with thionyl chloride, phosgene, phosphorus oxychloride, etc.; or the like.

The reaction may also be carried out in the presence of an organic or inorganic base such as an alkali metal bicarbonate, tri(lower)alkylamine, pyridine, N-(lower)-alkylmorpholine, N,N-di(lower)alkylbenzylamine, or the like.

The reaction temperature is not critical, and the reaction is usually carried out under cooling to heating.

Process 7

The compound (Ih) or a salt thereof can be prepared by subjecting the compound (If) or a salt thereof to halogenation with a halogenating agent such as N-halosuccinimide (e.g. N-chlorosuccinimide, N-bromosuccinimide, etc.), or the like.

The reaction is usually carried out in a solvent such as tetrahydrofuran, dioxane, toluene, dichloromethane, 1,2-dichloroethane, chloroform, N,N-dimethylformamide, N,N-dimethylacetamide, or any other organic solvent which does not adversely affect the reaction, or a mixture thereof.

Process 8

The compound (Ij) or a salt thereof can be prepared by subjecting the compound (Ih) or a salt thereof to coupling reaction with the compound (V) or a salt thereof.

This reaction can be carried out in the same manner as the aforementioned coupling reaction in Process 1, and therefore the reagents to be used and the reaction conditions (e.g., solvent, reaction temperature, etc.) can be referred to those of Process 1.

Process A

The compound (VII) or a salt thereof can be prepared by subjecting the compound (VI) or a salt thereof to hydrolysis using an acid (exemplified by Step 1). This reaction can be carried out in the same manner as the aforementioned hydrolysis using an acid in Process 2, and therefore the reagents to be used and the reaction conditions (e.g., solvent, reaction temperature, etc.) can be referred to those of Process 2.

And the object compound (VIII) can be prepared by subjecting the compound (VII) or a salt thereof to the alkylation with the compound (IV) or a salt thereof (exemplified by Step 2). This reaction can be carried out in the same manner as in the aforementioned Process 3, and therefore the reagents to be used and the reaction conditions (e.g., solvent, reaction temperature, etc.) can be referred to those of Process 3.

Process B

The compound (X) or a salt thereof can be prepared from the acetylation of the compound (IX) (exemplified by Step 1) by the methods disclosed in Preparation 1 mentioned later or the similar manner thereto.

And the object compound (XI) can be prepared by subjecting the compound (X) to the oxime-formation reaction (exemplified by Step 2) that disclosed in Preparation 2 mentioned later or the similar manners thereto.

Process C

The compound (XII) or a salt thereof can be prepared by reacting the compound (XI) or a salt thereof with aminomalonitrile or a salt thereof.

The present reaction is preferably carried out in the presence of a catalyst such as p-toluenesulfonic acid, and the like.

This reaction is usually carried out in a conventional solvent such as water, acetone, dioxane, acetonitrile, 1,2-dimethoxyethane, chloroform, dichloromethane, 1,2-dichloroethane, tetrahydrofuran, ethyl acetate, N,N-dimethylformamide, methanol, ethanol, isopropanol, t-butanol, diethyl ether, isopropyl ether, a mixture thereof or any other organic solvent which does not adversely affect the reaction.

The reaction temperature is not critical, and the reaction is usually carried out at ambient temperature, under warming or heating.

This reaction can be carried out by the method disclosed in Preparation 3 mentioned later or the similar manner thereto.

Process D

The compound (XVI) or a salt thereof can be prepared by subjecting the compound (XIII) or a salt thereof to hydrolysis using an acid.

Process E

The compound (II) or a salt thereof can be prepared by reacting the compound (XV) or a salt thereof with the compound (XVI) or a salt thereof.

This reaction is usually carried out in a conventional solvent such as acetone, dioxane, acetonitrile, 1,2-dimethoxyethane, chloroform, dichloromethane, 1,2-dichloroethane, tetrahydrofuran, ethyl acetate, N,N-dimethylformamide, diethyl ether, isopropyl ether, a mixture thereof or any other organic solvent which does not adversely affect the reaction.

This reaction can be carried out by the method disclosed in Preparation 4 mentioned later or the similar manner thereto.

Above processes, all starting materials and product compounds may be salts. The compounds of above processes can be converted to salts according to a conventional method.

The object compound (I) of the present invention is an adenosine antagonist and possesses the various pharmacological actions as stated before.

In order to show the usefulness of the compound (I) of the present invention, the pharmacological test result of the representative compound of the present invention is shown in the following.

Test 1: Adenosine Antagonistic Activity

[I] Test Method

The adenosine antagonistic activity [Ki(nM)] of the test compound was examined by radioligand binding techniques using 8-cyclopentyl-1,3-dipropylxanthine, [dipropyl-2,3-$^3$H(N)] ([$^3$H]DPCPX, 4.5 nM) for human $A_1$ receptor and [$^3$H] CGS 21680 (20 nM) for human $A_{2a}$ receptor.

[II] Test Compound

3-Amino-6-(1-ethyl-6-oxo-1,6-dihydro-3-pyridyl)-5-phenyl-2-pyrazinecarboxamide (Example 4)

3-Amino-6-(1-methyl-6-oxo-1,6-dihydro-3-pyridyl)-5-phenyl-2-pyrazinecarbonitrile (Example 11)

3-Amino-S-(3,4-difluorophenyl)-6-(1-isopropyl-6-oxo-1,6-dihydro-3-pyridyl)-2-pyrazinecarbonitrile (Example 39)

3-Amino-N-(cyanomethyl)-6-(1-isopropyl-6-oxo-1,6-dihydro-3-pyridyl)-5-phenyl-2-pyrazinecarboxamide (Example 46)

5-[5-amino-6-(hydroxymethyl)-3-phenyl-2-pyrazinyl]-1-isopropyl-2(1H)-pyridone (Example 47)

3-Amino-N-(2-hydroxyethyl)-6-(1-isopropyl-6-oxo-1,6-dihydro-3-pyridyl)-5-phenyl-2-pyrazinecarboxamide (Example 49)

5-(5-amino-6-bromo-3-phenyl-2-pyrazinyl)-3-bromo-1-isopropyl-2(1H)-pyridone (Example 53)

5-[5-Amino-3-(2-thienyl)-2-pyrazinyl]-1-isopropyl-2(1H)-pyridone (Example 115)

5-[5-Amino-3-(3,5-difluorophenyl)-2-pyrazinyl]-1-isopropyl-2(1H)-pyridone (Example 129)

5-(5-amino-6-bromo-3-phenyl-2-pyrazinyl)-1-isopropyl-2(1H)-pyridone (Example 141)

5-[5-Amino-6-(2-furyl)-3-phenyl-2-pyrazinyl]-1-isopropyl-2(1H)-pyridone (Example 144)

5-(5-amino-6-phenoxy-3-phenyl-2-pyrazinyl)-1-isopropyl-2(1H)-pyridone (Example 151)

[III] Test Result

TABLE 1

| Test compound | Adenosine receptor binding (Ki:nM) | |
|---|---|---|
| (Example No.) | $A_1$ | $A_{2a}$ |
| 4 | 5.09 | 2.34 |
| 11 | 22.47 | 2.35 |
| 39 | 23.99 | 6.52 |
| 46 | 5.25 | 1.49 |
| 47 | 22.27 | 7.52 |
| 49 | 6.07 | 1.69 |
| 53 | 0.93 | 0.91 |
| 115 | 4.89 | 0.84 |
| 129 | 10.71 | 3.90 |
| 141 | 0.61 | 0.23 |
| 144 | 1.78 | 0.54 |
| 151 | 1.57 | 0.32 |

Test 2: Anticatalepsy Activity in Mouse

[I] Test Method

The test compound (3.2 mg/kg) was administered orally with ddY mice (n=7). Then, haloperidol (0.32 mg/kg) was injected intraperitoneally 30 min. after the administration of the compound. Thirty min after the injection, the cataleptic responses of mice were measured. The forelimbs of each mouse were placed on a 3 cm high, 3 mm wide horizontal bar, and the duration of cataleptic posture was measured for up to 30 sec.

[II] Test Compound

3-Amino-6-(1-ethyl-6-oxo-1,6-dihydro-3-pyridyl)-5-phenyl-2-pyrazinecarboxamide (Example 4)

3-Amino-6-(1-methyl-6-oxo-1,6-dihydro-3-pyridyl)-5-phenyl-2-pyrazinecarbonitrile (Example 11)

3-Amino-5-(3,4-difluorophenyl)-6-(1-isopropyl-6-oxo-1,6-dihydro-3-pyridyl)-2-pyrazinecarbonitrile (Example 39)

3-Amino-N-(cyanomethyl)-6-(1-isopropyl-6-oxo-1,6-dihydro-3-pyridyl)-5-phenyl-2-pyrazinecarboxamide (Example 46)

5-[5-amino-6-(hydroxymethyl)-3-phenyl-2-pyrazinyl]-1-isopropyl-2(1H)-pyridone (Example 47)

3-Amino-N-(2-hydroxyethyl)-6-(1-isopropyl-6-oxo-1,6-dihydro-3-pyridyl)-5-phenyl-2-pyrazinecarboxamide (Example 49)

5-(5-amino-6-bromo-3-phenyl-2-pyrazinyl)-3-bromo-1-isopropyl-2(1H)-pyridone (Example 53)

5-[5-Amino-3-(2-thienyl)-2-pyrazinyl]-1-isopropyl-2(1H)-pyridone (Example 115)

5-[5-Amino-3-(3,5-difluorophenyl)-2-pyrazinyl]-1-isopropyl-2(1H)-pyridone (Example 129)

5-(5-amino-6-bromo-3-phenyl-2-pyrazinyl)-1-isopropyl-2(1H)-pyridone (Example 141)

5-[5-Amino-6-(2-furyl)-3-phenyl-2-pyrazinyl]-1-isopropyl-2(1H)-pyridone (Example 144)

5-(5-amino-6-phenoxy-3-phenyl-2-pyrazinyl)-1-isopropyl-2(1H)-pyridone (Example 151)

[III] Test Result

TABLE 2

| Test compound (Example No.) | Manifestation rate of Catalepsy (number of mouse) |
| --- | --- |
| 4 | 0/7 |
| 11 | 0/7 |
| 39 | 0/7 |
| 46 | 0/7 |
| 47 | 1/7 |
| 49 | 1/7 |
| 53 | 0/7 |
| 115 | 0/7 |
| 129 | 0/7 |
| 141 | 0/7 |
| 144 | 0/7 |
| 151 | 0/7 |

The pyrazine compound (I) and a salt thereof of this invention are useful as adenosine antagonists (especially, $A_1$ receptor and $A_2$ (particularly $A_{2a}$) receptor dual antagonists) and for the prevention and/or the treatment of depression, dementia (e.g. Alzheimer's disease, cerebrovascular dementia, dementia accompanying Parkinson's disease, etc.), Parkinson's disease, anxiety, pain, cerebrovascular disease, heart failure, hypertension, circulatory insufficiency, post-resuscitation, asystole, bradyarrhythmia, electromechanical dissociation, hemodynamic collapse, SIRS (systemic inflammatory response syndrome), multiple organ failure, renal failure (renal insufficiency), renal toxicity, nephrosis, nephritis, edema, obesity, bronchial asthma, gout, hyperuricemia, sudden infant death syndrome, immunosuppression, diabetes, ulcer, pancreatitis, Meniere's syndrome, anemia, dialysis-induced hypotension, constipation, ischemic bowel disease, ileus, myocardial infarction, thrombosis, obstruction, arteriosclerosis obliterans, thrombophlebitis, cerebral infarction, transient ischemic attack, angina pectoris, and the like.

Adenosine antagonists can be useful for Parkinson's disease by co-administrating with L-3,4-dihidroxy-phenylalanine (L-DOPA), which is the most popular drug for Parkinson's disease (R. Grondin et al., Neurology, 52, 1673 (1999)). So the combination use of the pyrazine compound (I) and a salt thereof of this invention with L-DOPA may be also useful for treatment and/or prevention of Parkinson's disease with decreasing or reducing the side effect such as the onset of dyskinesia eliciting by the long-team application of L-DOPA, and so on.

Further, in view of the field using these compounds for as a medicament, these compounds should be durable to some degree. And the duration time of the pyrazine compound (I) or a salt thereof of this invention are expected to be long-lasting.

The pharmaceutical composition of this invention can be used in the form of a pharmaceutical preparation, for example, in a solid, semisolid or liquid form, which contains the pyrazine compound (I) or a pharmaceutically acceptable salt thereof as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. In addition, auxiliary, stabilizing agents, thickening agents, coloring agents and perfumes may be used where necessary. The pyrazine compound (I) or a pharmaceutically acceptable salt thereof is included in a pharmaceutical composition in an amount sufficient to produce the desired aforesaid pharmaceutical effect upon the process or condition of diseases.

For applying the composition to a human being or an animal, it is preferable to apply it by intravenous, intramuscular, pulmonary or oral administration, or insufflation. While the dosage of therapeutically effective amount of the pyrazine compound (I) varies depending on the age and condition of each individual patient to be treated, in the case of intravenous administration, a daily dose of 0.01-100 mg of the pyrazine compound (I) per kg weight of a human being or an animal, in the case of intramuscular administration, a daily dose of 0.1-100 mg of the pyrazine compound (I) per kg weight of a human being or an animal, and in case of oral administration, a daily dose of 0.5-100 mg of the pyrazine compound (I) per kg weight of a human being or an animal is generally given for the prevention and/or treatment of the aforesaid diseases.

The following preparations and examples are given for the purpose of illustrating the present invention in more detail.

The abbreviations, symbols and terms used in the preparations and examples have the following meanings.

AcOH acetic acid
$CHCl_3$ chloroform
$CH_2Cl_2$ dichloromethane
DME 1,2-dimethoxyethane
DMF N,N-dimethylformamide
DMSO dimethyl sulfoxide
EtOAc ethyl acetate
EtOH ethanol
IPA isopropyl alcohol
IPE isopropyl ether
MeOH methanol
MeCN acetonitrile
NMP N-methylpyrrolidone
THF tetrahydrofuran
HCl hydrochloric acid
$NEt_3$ triethylamine t-BuOK potassium tert-butoxide
$K_2CO_3$ potassium carbonate
$MgSO_4$ magnesium sulfate
NaOAc sodium acetate
$Na_2CO_3$ sodium carbonate
NaH sodium hydride
$NaHCO_3$ sodium bicarbonate
NaOH sodium hydroxide
EtI ethyl iodide
MeI methyl iodide
n-PrBr n-propyl bromide
i-PrI isopropyl iodide
CuI cuprous iodide (copper(I) iodide)
$PdCl_2$ $(PPh_3)_2$ dichlorobis(triphenylphosphine)-palladium(II)
$Pd(OAc)_2$ palladium(II) acetate
$Pd(PPh_3)_4$ tetrakis(triphenylphosphine)-palladium(II)
aq. aqueous
conc. concentrated
sat. saturated Preparation 1

2-Methoxybromopyridine (25 g) and n-butyl vinyl ether (66.6 g) were dissolved in DMF (250 ml). To the solution were added 1,3-bis(diphenylphosphino)propane (3.62 g) and $Pd(OAc)_2$ (896 mg) and aq. $K_2CO_3$ under nitrogen atmosphere. The reaction mixture was stirred for 2 hours at 100-120° C. The mixture was cooled to 25° C. To the solution was added 1N aq. HCl (625 ml). The solution was stirred for 1 hour at 25-30° C. The solution was portioned to EtOAc and water. The organic layer was separated. The aqueous layer was extracted with EtOAc. The combined organic solution was washed with water and brine, and dried over $MgSO_4$. Evaporation of solvent in vacuo gave oily residue. The residue was purified by chromatography on silica gel (EtOAc:n-Hexane=1:5, v/v) to give 2-methoxy-5-acetylpyridine as a solid (12.14 g).

$^1$H-NMR (DMSO-$d_6$ δ): 2.56 (3H, s), 3.95 (3H, s), 6.92 (1H, d, J=8.4 Hz), 8.17 (1H, dd, J=2.4, 8.4 Hz), 8.30 (1H, d, J=2.4 Hz) MS (ESI$^+$): 152 [M+H]$^+$

Preparation 2

2-Methoxy-5-acetylpyridine (12.1 g) and t-butyl nitrite (9.92 g) were dissolved in THF (120 ml). The solution was cooled at 0-5° C. To the solution was added t-BuOK (10.8 g) at 5-25° C. The reaction mixture was stirred at 25° C. for 2 hours. To the mixture was added 1N HCl (105 ml). The solution was portioned to EtOAc and water. The organic layer was separated. The aqueous layer was extracted with EtOAc. The combined organic solution was washed with 10% aq. NaOAc and brine successively, dried over $MgSO_4$. Evaporation of solvent in vacuo gave solid residue. The residue was pulverized with IPE (150 ml). The precipitated crystals were collected by filtration, to give (1E)-(6-methoxy-3-pyridyl)(oxo)acetaldehyde oxime as a solid (5.45 g) (anti, syn mixture (anti:syn=1:1)). Evaporation of solvent in the filtrate gave a residue. The residue was pulverized with IPE. The precipitated crystals were collected by filtration, to give (1E)-(6-methoxy-3-pyridyl)(oxo)acetaldehyde oxime as a solid (2.5 g) (anti, syn mixture (anti:syn=1:1)).

Anti Form $^1$H-NMR (DMSO-$d_6$ δ): 3.95 (3H, s), 6.95 (1H, d, J=8.4 Hz), 8.00 (1H, s), 8.23 (1H, dd, J=2.4, 8.4 Hz), 8.85 (1H, d, J=2.4 Hz), 12.7 (1H, s) MS (ESI$^+$): 181 [M+H]$^+$, 203 [M+Na]$^+$ Syn Form $^1$H-NMR (DMSO-$d_6$ δ): 3.96 (3H, s), 7.00 (1H, d, J=8.4 Hz), 7.59 (1H, s), 8.09 (1H, dd, J=2.4, 8.4 Hz), 8.64 (1H, d, J=2.4 Hz), 11.8 (1H, s), MS (ESI$^+$): 181 [M+H]$^+$, 203 [M+Na]$^+$ Preparation 3

(1E)-(6-Methoxy-3-pyridyl)(oxo)acetaldehyde oxime (5.4 g) and aminomalonitrile p-toluenesulfonate (7.6 g) were suspended in 2-propanol (108 ml) and stirred at 25° C. To the mixture was added p-toluenesulfonic acid (5.71 g). The mixture was heated at 50° C. for 2 hours, then at ambient temperature for 1 hour. The above reaction mixture was concentrated in vacuo. To the concentrated solution was added sat. aq. NaOAc. Crystals were precipitated. The suspension was stirred at 20° C. for 15 hours. The crystals were collected by filtration, and dried in vacuo to give 3-amino-6-(6-methoxy-3-pyridyl)-2-pyrazinecarbonitrile 4-oxide as powder (6.65 g).

$^1$H-NMR (DMSO-$d_6$ δ): 3.90 (3H, s), 6.92 (1H, d, J=8.6 Hz), 8.06 (2H, brs), 8.23 (1H, dd, J=2.4, 8.6 Hz), 8.74 (1H, d, J=2.4 Hz), 9.21 (1H, s) MS (ESI$^+$): 244 [M+H]$^+$, IR (KBr): 3386, 3186, 2238, 1639, 1610, 1489, 1189 cm$^{-1}$ Preparation 4

3-Amino-6-(6-methoxy-3-pyridyl)-2-pyrazinecarbonitrile 4-oxide (6.65 g) was dissolved in DME (133 ml). To the solution was added phosphorus oxychloride (12.6 g) at 25° C. The mixture was stirred at ambient temperature for 2 hours. To the mixture was added water (520 ml). The solution was stirred at 20-25° C. for 15 hours. The precipitated crystals were collected by filtration and dried in vacuo, to give 3-amino-5-chloro-6-(6-methoxy-3-pyridyl)-2-pyrazinecarbonitrile as powder (4.6 g). The filtrate was extracted with EtOAc. The organic solution was washed with brine, dried over $MgSO_4$. Evaporation of solvent in vacuo gave oily residue. The residue was purified by chromatography on silica gel (EtOAc:n-Hexane=1:1, v/v) to give 3-amino-5-chloro-6-(6-methoxy-3-pyridyl)-2-pyrazinecarbonitrile as powder (1.0 g).

$^1$H-NMR (DMSO-$d_6$ δ): 3.93 (3H, s), 6.92 (1H, d, J=8.6 Hz), 7.88 (2H, s), 7.95 (1H, dd, J=2.4, 8.6 Hz), 8.43 (1H, d, J=2.4 Hz) MS (ESI$^+$): 262 [M+H]$^+$, 284 [M+Na]$^+$, IR (KBr): 3384, 3187, 2227, 1656, 1610, 1475, 1209 cm$^{-1}$

Preparation 5

2-Methoxy-5-bromo-pyridine (615 g) was dissolved in 6N HCl (3 l). The solution was heated at 99-105° C. The mixture was refluxed and stirred for 5 hours. The above reaction mixture was cooled to 5° C. The pH of the solution was adjusted to 6.5 with 10% aq. NaOH. The precipitated crystal was collected by filtration and washed with water (500 ml), and dried in vacuo, to give 5-bromo-2(1H)-pyridone (570 g) as crystal.

$^1$H-NMR (DMSO-$d_6$ δ): 6.36 (1H, d, J=9.8 Hz), 7.55 (1H, dd, J=2.8, 9.8 Hz), 7.69 (1H, d, J=2.4 Hz), 11.7 (1H, s) MS (ESI$^+$): 196 and 198 [M+Na]$^+$

Preparation 6 t-BuOK (32.2 g) was added to the suspension of 5-bromo-2(1H)-pyridone (50 g) in DME (500 ml). The mixture was stirred for 30 minutes. To the mixture was added $K_2CO_3$ (27.8 g) and 2-iodopropane (81.6 g). The reaction mixture was refluxed with stirring for 3 hours. The above mixture was cooled to 20-25° C. The precipitated salt was removed by filtration and washed with DME (100 ml). Evaporation of solvent in vacuo gave solidly residue. The residue was dissolved in $CHCl_3$ (150 ml). The solution was washed with 0.1N HCl and brine, and dried over $MgSO_4$. Evaporation of solvent in vacuo gave solidly residue. To the residue was added n-hexane (150 ml) to pulverize the residue. The precipitate was collected by filtration and dried in vacuo to give 5-bromo-1-isopropyl-2(1H)-pyridone (41.2 g).

$^1$H-NMR (DMSO-$d_6$ δ): 1.29 (6H, d, J=6.8 Hz), 4.99 (1H, m), 6.36 (1H, d, J=9.6 Hz), 7.48 (1H, dd, J=2.4, 9.6 Hz), 7.96 (1H, d, J=2.4 Hz) MS (ESI$^+$): 216 and 218 [M+H]$^+$, 238 and 240 [M+Na]$^+$

Preparation 7

5-Bromo-1-isopropyl-2(1H)-pyridone (50 g) was dissolved in n-butyl vinyl ether (250 ml). To the solution were added 1,3-bis(diphenylphosphino)propane (6.3 g) and powdered $K_2CO_3$ (38.2 g) and Pd(OAc)$_2$ (1.56 g) at 25° C. The mixture was heated at 90-95° C. with stirring for 8 hours. The reaction mixture was cooled to 25-30° C. To the cooled mixture was added $CHCl_3$ (125 ml). The precipitated salt was removed by filtration and washed with $CHCl_3$ (125 ml). Evaporation of solvent in the filtrate in vacuo gave oily residue. The residue was dissolved in $CHCl_3$ (125 ml). To the solution was added 1N HCl (125 ml). The reaction mixture was stirred at 25-30° C. for 1 hour. The organic layer was separated. The aqueous layer was extracted with $CHCl_3$ (100 ml). The combined organic layer was washed with 10% aq. $NaHCO_3$ (50 ml) and dried over $MgSO_4$ (25 g) and silica gel (25 g). $MgSO_4$ and silica gel were removed by filtration and washed with $CHCl_3$. Evaporation of solvent in the filtrate in vacuo gave oily residue, which was crystallized from n-hexane (500 ml). The crystal was collected by filtration and dried in vacuo at 40° C., to give 5-acetyl-1-isopropyl-2(1H)-pyridone (32.35 g).

$^1$H-NMR (DMSO-$d_6$ δ): 1.37 (6H, d, J=6.8 Hz), 2.47 (3H, s), 5.02 (1H, m), 6.44 (1H, d, J=9.6 Hz), 7.82 (1H, dd, J=2.6, 9.6 Hz), 8.41 (1H, d, J=2.6 Hz) MS (ESI$^+$): 180 [M+H]$^+$, 202 [M+Na]$^+$

Preparation 8

5-Acetyl-1-isopropyl-2(1H)-pyridone was dissolved in $CH_2Cl_2$ (300 ml). The solution was cooled to −30∼−25° C. To the cooled solution were added 4N hydrogen chloride in dioxane (55.3 ml) and t-butyl nitrite (10.4 g) at −30∼−25° C. The temperature of the reaction mixture was raised to 20-25° C. The mixture was stirred at the same temperature for 3 hours. The precipitated crystal was collected by filtration, and dried in the air at ambient temperature, to give (1E)-(1-isopropyl-6-oxo-1,6-dihydro-3-pyridyl)(oxo)acetaldehyde oxime (14.0 g).

$^1$H-NMR (DMSO-$d_6$ δ): 1.35 (6H, d, J=6.8 Hz), 5.02 (1H, m), 6.47 (1H, d, J=9.6 Hz), 7.89 (1H, dd, J=2.4, 9.6 Hz), 8.00 (1H, s), 8.69 (1H, d, J=2.4 Hz), 12.65 (1H, brs) MS (ESI$^+$): 209 [M+H]$^+$, 231 [M+Na]$^+$, IR (KBr): 3129, 1660, 1617, 1529, 1018 cm$^{-1}$

Preparation 9

The mixture of (1E)-(1-isopropyl-6-oxo-1,6-dihydro-3-pyridyl)(oxo)acetaldehyde oxime (14 g) and aminomalonitrile p-toluenesulfonate (17 g) and IPA (210 ml) was heated at 75-80° C. and stirred for 2 hours at the same temperature. The reaction mixture was cooled to 0-5° C. and stirred for 2 hours. The precipitate was collected by filtration, and dried in vacuo, to give 3-amino-6-(1-isopropyl-6-oxo-1,6-dihydro-3-pyridyl)-2-pyrazinecarbonitrile 4-oxide (9.2 g).

$^1$H-NMR (DMSO-$d_6$ δ): 1.36 (6H, d, J=6.8 Hz), 5.09 (1H, m), 6.48 (1H, d, J=9.6 Hz), 7.92-7.99 (3H, m), 8.28 (1H, d, J=2.6 Hz), 9.25 (1H, s) MS (ESI$^+$): 293 [M+Na]$^+$, IR (KBr): 3122, 2200, 1656, 1598, 1531, 1174 cm$^{-1}$

Preparation 10

3-Amino-6-(1-isopropyl-6-oxo-1,6-dihydro-3-pyridyl)-2-pyrazinecarbonitrile 4-oxide (9 g) was dissolved in 25% hydrogen bromide solution of ACOH (90 ml) at 20-25° C. The reaction mixture was stirred for 2 hours at ambient temperature. To the reaction mixture was added dioxane (180 ml). The suspension was stirred for 2 hours at ambient temperature. The precipitate was collected by filtration and washed with dioxane, and dried in the air at ambient temperature. The above powder was suspended in water (90 ml). The pH of the suspension was adjusted to 8-8.5 with 1N NaOH (70 ml). The suspension was stirred at ambient temperature. The precipitate was collected by filtration and washed with water, and dried in vacuo at 50° C., to give 3-amino-6-(1-isopropyl-6-oxo-1,6-dihydro-3-pyridyl)-2-pyrazinecarboxamide 4-oxide (8.80 g).

$^1$H-NMR (DMSO-$d_6$ δ): 1.39 (6H, d, J=6.8 Hz), 5.10 (1H, m), 6.46 (1H, d, J=9.4 Hz), 7.88 (2H, s), 7.89 (1H, s), 8.32 (1H, dd, J=2.4, 9.4 Hz), 8.41 (1H, d, J=2.4 Hz), 8.51 (1H, s), 9.15 (1H, s) MS (ESI$^+$): 312 [M+Na]$^+$, IR (KBr): 3440, 1660, 1596, 1554, 1186 cm$^{-1}$

Preparation 11

3-Amino-6-(1-isopropyl-6-oxo-1,6-dihydro-3-pyridyl)-2-pyrazinecarboxamide 4-oxide (8 g) was dissolved in DMF (80 ml). The solution was cooled to −30° C. To the cooled solution was added phosphoryl chloride (12.7 g) dropwise at −30∼−40° C. After addition of phosphoryl chloride, the temperature of the reaction mixture was raised to −10∼−5° C. The mixture was stirred at −10∼−5° C. for 1 hour. To the reaction mixture was added water (400 ml). The suspension was stirred at 30-35° C. for 15 hours. The pH of the suspension was adjusted to 4.5. The suspension was cooled to 0-5° C. and stirred at the same temperature for 2 hours. The precipitate was collected by filtration and washed with water, and dried in vacuo at 40-50° C., to give 3-amino-5-chloro-6-(1-isopropyl-6-oxo-1,6-dihydro-3-pyridyl)-2-pyrazinecarboxamide (7.1 g).

$^1$H-NMR (DMSO-$d_6$ δ): 1.34 (6H, d, J=7.0 Hz), 5.09 (1H, m), 6.44 (1H, d, J=9.4 Hz), 7.74 (1H, s), 7.85 (1H, dd, J=2.4, 9.4 Hz), 7.85 (2H, s), 8.13 (1H, d, J=2.4 Hz), 8.13 (1H, s) MS (ESI$^+$): 330 and 332 [M+Na]$^+$, IR (KBr): 3284, 1673, 1604, 1461, 1187 cm$^{-1}$

Preparation 12

3-Amino-6-(1-isopropyl-6-oxo-1,6-dihydro-3-pyridyl)-2-pyrazinecarboxamide 4-oxide (29.1 g) was dissolved in DMF (290 ml). The solution was cooled to −30° C. To the cooled solution was added phosphoryl chloride (46.3 g) dropwise at −30∼−40° C. After addition of phosphoryl chloride, the temperature of the reaction mixture was raised to 40-45° C. The mixture was stirred at 40-45° C. for 1 hour. To the reaction mixture was added water (1160 ml). The suspension was stirred at 30-35° C. for 15 hours. The pH of the suspension was adjusted to 7 with 12% aq. NaOH (400 ml). The suspension was cooled to 0-5° C. and stirred at the same temperature for 2 hours. The precipitate was collected by filtration and washed with water, and dried in vacuo at 40-50° C., to give 3-amino-5-chloro-6-(1-isopropyl-6-oxo-1,6-dihydro-3-pyridyl)-2-pyrazinecarbonitrile (17.2 g).

$^1$H-NMR (DMSO-$d_6$ δ): 1.34 (6H, d, J=7.0 Hz), 5.09 (1H, m), 6.44 (1H, d, J=9.4 Hz), 7.74 (1H, s), 7.85 (1H, dd, J=2.4, 9.4 Hz), 7.85 (2H, s), 8.13 (1H, d, J=2.4 Hz), 8.13 (1H, s) MS (ESI$^+$): 330 [M+Na]$^+$, IR (KBr): 3291, 1662, 1600, 1465, 1182 cm$^{-1}$

Preparation 13

To a solution of 1-(diphenylmethyl)-3-azetidinol hydrochloride (5.0 g) in DMF (25 ml), was added sodium hydride under ice-bath cooling. After 10 minute stirring at the same temperature, the mixture was allowed to warm to 25° C. and then stirred for 15 hours. EtOAc (500 ml) and water (200 ml) were poured into the mixture. The organic layer was separated, washed with water and brine, and dried over MgSO$_4$. The solvent was removed under reduced pressure. The residue was purified by column chromatography (silica gel; 200 ml, toluene:EtOAc=15:1-8:1) to give 1-(diphenylmethyl)-3-methoxyazetidine (3.41 g).

$^1$H-NMR (DMSO-$d_6$ δ): 2.7-2.9 (2H, m), 3.12 (3H, s), 3.3-3.5 (2H, m), 3.99 (1H, m), 4.40 (1H, s), 7.1-7.4 (6H, m), 7.3-7.5 (4H, m) MS (ESI$^+$): 254 [M+H]$^+$

Preparation 14

To a solution of 1-(diphenylmethyl)-3-methoxyazetidine (3.4 g) in MeOH (35 ml), was added 20% palladium hydroxide on carbon (0.7 g). And then the mixture was stirred under hydrogen atmosphere for 2.5 hours. 1N HCl (20 ml) was added to the mixture and the catalyst was removed by filtration and washed with 1N HCl. The solvent was removed under reduced pressure. Water and EtOAc were poured into the residue, and the aqueous layer was separated, washed with EtOAc. The solvent was removed under reduced pressure and the residue was azeotroped with EtOH and dried in vacuo. n-Hexane was poured into the residue and a crystal was isolated by filtration, washed with n-hexane, and dried in vacuo to give 3-methoxyazetidine hydrochloride (1.58 g)

$^1$H-NMR (DMSO-$d_6$ δ): 3.21 (3H, s), 3.6-3.9 (2H, m), 4.0-4.4 (3H, m) MS (ESI$^+$): 88 [M+H]$^+$ (free form)

Preparation 15

The mixture of 5-bromo-2(1H)-pyridone (200 g) and MeI (324 g) and K$_2$CO$_3$ (318 g) in DME (2 l) was heated at 80° C. with stirring for 2 hours. The above mixture was cooled to room temperature. The precipitated salt was removed by filtration and washed with DME. Evaporation of solvent in the filtrate in vacuo gave oily residue. The residue was portioned to EtOAc and water. The organic layer was separated. Aqueous layer was extracted with EtOAc twice. The combined organic solution was dried over MgSO$_4$. Evaporation of solvent in vacuo gave crystal residue. The residue was pulverized with IPE and n-hexane (1:3, 1000 ml). The precipitate was collected by filtration and dried in vacuo to give 5-bromo-1-methyl-2(1H)-pyridone as white powder (182.5 g).

$^1$H-NMR (DMSO-$d_6$ δ): 3.40 (3H, s), 6.36 (1H, d, J=9.6 Hz), 7.51 (1H, dd, J=2.8, 9.6 Hz), 8.03 (1H, d, J=2.8 Hz) MS (ESI$^+$): 210 and 212 [M+Na]$^+$ Preparation 16

5-Bromo-1-methyl-2(1H)-pyridone (150 g) was dissolved in DMF (1500 ml). To the solution were added 1,3-bis(diphenylphosphino)propane (21.7 g), n-butyl vinyl ether (400 g), and 3M aq. potassium carbonate (262.5 ml) and Pd(OAc)$_2$ (10.2 g). The mixture was heated at 80° C. and stirred for 3 hours at the same temperature. The reaction mixture was cooled to 25-30° C. and poured to 1N HCl (1485 ml). The mixture was stirred for 2 hours at 30-40° C. The solution was extracted with EtOAc (1500 ml, three times). The aqueous layer was extracted with CH$_2$Cl$_2$ (1000 ml, three times). The collected organic solution was dried over MgSO$_4$. Evaporation of solvent gave solidly residue, which was pulverized with IPA (150 ml) and IPE (1500 ml). The suspension was stood in the refrigerator overnight. The precipitate was collected by filtration, dried in vacuo, to give 5-acetyl-1-methyl-2(1H)-pyridone as white powder (128 g).

$^1$H-NMR (DMSO-$d_6$ δ): 2.41 (3H, s), 3.52 (3H, s), 6.42 (1H, d, J=9.6 Hz), 7.84 (1H, dd, J=2.4, 9.6 Hz), 8.66 (1H, d, J=2.4 Hz) MS (ESI$^+$): 152 [M+H]$^+$, 174 [M+Na]$^+$

Preparation 17

(1E)-(1-Methyl-6-oxo-1,6-dihydro-3-pyridyl)(oxo) acetaldehyde oxime

The title compound was obtained in a similar manner to that of Preparation 8.

$^1$H-NMR (DMSO-$d_6$ δ): 3.57 (3H, s), 6.47 (1H, d, J=9.6 Hz), 7.93 (1H, dd, J=2.4, 9.6 Hz), 8.03 (1H, s), 8.76 (1H, d, J=2.4 Hz), 12.62 (1H, s) MS (ESI$^+$): 203 [M+Na]$^+$

Preparation 18

3-Amino-6-(1-methyl-6-oxo-1,6-dihydro-3-pyridyl)-2-pyrazinecarbonitrile 4-oxide

The title compound was obtained in a similar manner to that of Preparation 9.

$^1$H-NMR (DMSO-$d_6$ δ): 3.50 (3H, s), 6.47 (1H, d, J=9.6 Hz), 7.96 (2H, s), 7.96-8.02 (1H, m), 8.43 (1H, d, J=2.4 Hz), 9.04 (1H, s) MS (ESI$^+$): 244 [M+Na]$^+$

Preparation 19

3-Amino-6-(1-methyl-6-oxo-1,6-dihydro-3-pyridyl)-2-pyrazinecarbonitrile 4-oxide (97 g) was added to 25% hydrogen bromide solution of AcOH (700 ml) at 25-30° C. The mixture was stirred for 2 hours at ambient temperature. To the mixture was added 12% aq. NaOH (2100 ml) and water (1000 ml). The mixture was stirred overnight at the refrigerator. The resultant precipitated crystals were collected by filtration, and washed with water, and dried in vacuo, to give 3-amino-6-(1-methyl-6-oxo-1,6-dihydro-3-pyridyl)-2-pyrazinecarboxamide 4-oxide as powder (52 g).

$^1$H-NMR (DMSO-$d_6$ δ): 3.52 (3H, s), 6.45 (1H, d, J=9.6 Hz), 7.82 (2H, s), 7.92 (1H, s), 8.26 (1H, dd, J=2.6, 9.6 Hz), 8.54 (1H, s), 8.72 (1H, d, J=2.6 Hz), 8.97 (1H, s) MS (ESI$^+$): 262 [M+H]$^+$, 284 [M+Na]$^+$

Preparation 20

3-Amino-5-chloro-6-(1-methyl-6-oxo-1,6-dihydro-3-pyridyl)-2-pyrazinecarbonitrile The title compound was obtained in a similar manner to that of Preparation 12.

¹H-NMR (DMSO-d₆ δ): 3.25 (3H, s), 6.45 (1H, d, J=9.4 Hz), 7.70 (1H, dd, J=2.6, 9.4 Hz), 7.83 (2H, s), 8.06 (1H, d, J=2.6 Hz) MS (ESI⁺): 262 and 263 [M+H]⁺, 284 and 286 [M+Na]⁺

Preparation 21

To a suspension of 3-amino-6-(1-methyl-6-oxo-1,6-dihydro-3-pyridyl)-2-pyrazinecarboxamide 4-oxide (1.0 g) in DMF was added phosphoric trichloride (1.07 ml) at −40° C. for 20 minutes. This reaction mixture was warmed to −10° C. and stirred for 1 hour. To this solution was added water (40 ml) and stirred at 40° C. for 14 hours. The pH of the resulting suspension was adjusted to 4.5 with 30% The pH of the aqueous mixture was adjusted to 6-7 with 12% aq. NaOH. The precipitate was collected by filtration and washed with water to give 3-amino-5-chloro-6-(1-methyl-6-oxo-1,6-dihydro-3-pyridyl)-2-pyrazinecarboxamide (263 mg) as a yellow powder.

MS (ESI⁺): 280 [M+H]⁺

EXAMPLE 1

3-Amino-5-chloro-6-(6-methoxy-3-pyridyl)-2-pyrazinecarbonitrile (1.35 g) was dissolved in dioxane (135 ml). To the solution were added phenylboronic acid (1.89 g) and Pd(PPh₃)₄ (179 mg) and Na₂CO₃ (2.19 g) in water (27 ml) at 25° C. The reaction mixture was heated at 80° C. for 2 hours, then at ambient temperature for 3 hours. The above mixture was portioned to EtOAc and water. The organic layer was separated and washed with aq. Na₂CO₃ and brine, and dried over MgSO₄. Evaporation of solvent in vacuo gave oily residue, which was purified by chromatography on silica gel (EtOAc:n-Hexane=1:1, v/v) to give 3-amino-6-(6-methoxy-3-pyridyl)-5-phenyl-2-pyrazinecarbonitrile as yellow crystal which was crystallized from EtOAc (1.15 g).

¹H-NMR (DMSO-d₆ δ): 3.81 (3H, s), 6.73 (1H, d, J=8.6 Hz), 7.35 (5H, s), 7.51 (2H, s), 7.54 (1H, dd, J=2.4, 8.6 Hz), 7.99 (1H, d, J=2.4 Hz) MS (ESI⁺): 304 [M+H]⁺, 326 [M+Na]⁺, IR (KBr): 3357, 3183, 2238, 1648, 1598, 1544, 1195 cm⁻¹, m.p.: 201-205° C. (IPE)

EXAMPLE 2

3-Amino-6-(6-methoxy-3-pyridyl)-5-phenyl-2-pyrazinecarbonitrile (500 mg) was dissolved in dioxane (10 ml) and conc. HCl (5 ml). The solution was stirred at 80° C. for 5 hours. The reaction mixture was cooled to 25-30° C. and concentrated in vacuo to give a residue. To the residue was added water and 1N NaOH to adjust the pH of the aqueous mixture to 6-7. The precipitated crystals were collected by filtration dried in vacuo to give 3-amino-6-(6-oxo-1,6-dihydro-3-pyridyl)-5-phenyl-2-pyrazinecarboxamide (390 mg).

¹H-NMR (DMSO-d₆ δ): 6.16 (1H, d, J=9.4 Hz), 7.26-7.70 (10H, m), 8.23 (1H, s), 11.66 (1H, s) MS (ESI⁺): 330 [M+Na]⁺, MS (ESI⁻): 306 [M−H]⁻, IR (KBr): 3309, 1656, 1610, 1544, 1201 cm⁻¹, m.p.: 215-220° C. (H₂O)

EXAMPLE 3

3-Amino-6-(6-oxo-1,6-dihydro-3-pyridyl)-5-phenyl-2-pyrazinecarboxamide (61.4 mg) was dissolved in DMF (1 ml) To the solution were added 1M MeI solution in DMF (0.22 ml) and 0.1M t-BuOK solution in DMF (2.2 ml). The mixture was stirred at 20-30° C. for 2 hours. The reaction mixture was portioned EtOAc and water. The organic layer was separated. The aqueous layer was extracted with EtOAc. The combined organic solution was washed with brine and dried over MgSO₄. Evaporation of solvent gave oily residue. The above residue was purified by chromatography on silica gel (EtOAc only-EtOAc:MeOH=93:7, v/v) to give 3-amino-6-(1-methyl-6-oxo-1,6-dihydro-3-pyridyl)-5-phenyl-2-pyrazinecarboxamide, which was crystallized from EtOAc (20 mg).

¹H-NMR (DMSO-d₆ δ): 3.45 (3H, s), 6.12 (1H, d, J=9.4 Hz), 6.97 (1H, dd, J=2.4, 9.4 Hz), 7.4177.62 (8H, m), 8.14 (1H, d, J=2.4 Hz), 8.29 (1H, s) MS (ESI⁺): 344 [M+Na]⁺, IR (KBr): 3353, 1664, 1599, 1531, 1438 cm⁻¹, m.p.: >250° C. (EtOAc)

EXAMPLE 4

3-Amino-6-(1-ethyl-6-oxo-1,6-dihydro-3-pyridyl)-5-phenyl-2-pyrazinecarboxamide

The title compound was obtained in a similar manner to that of Example 3.

¹H-NMR (DMSO-d₆ δ): 1.12 (3H, t, J=7.0 Hz), 3.84 (2H, q, J=7.0 Hz), 6.18 (1H, d, J=9.4 Hz), 7.21 (1H, dd, J=2.4, 9.4 Hz), 7.40-7.72 (8H, m), 7.89 (1H, d, J=2.4 Hz), 8.27 (1H, s) MS (ESI⁺): 336 [M+H]⁺, 358 [M+Na]⁺, IR (KBr): 3154, 1679, 1597, 1535, 1444 cm⁻¹, m.p.: >250° C. (EtOAc)

EXAMPLE 5

3-Amino-6-(6-oxo-1-propyl-1,6-dihydro-3-pyridyl)-5-phenyl-2-pyrazinecarboxamide

The title compound was obtained in a similar manner to that of Preparation 3.

¹H-NMR (DMSO-d₆ δ): 0.77 (3H, t, J=7.4 Hz), 1.52 (2H, m), 3.76 (2H, t, J=7.2 Hz), 6.20 (1H, d, J=9.4 Hz), 7.34-7.47 (8H, m), 7.66-7.72 (2H, m), 8.19 (1H, s) MS (ESI⁺): 350 [M+H]⁺, 372 [M+Na]⁺, IR (KBr): 3421, 1650, 1571, 1515, 1417 cm⁻¹, m.p.: >250° C. (EtOAc)

EXAMPLE 6

3-Amino-6-(6-oxo-1,6-dihydro-3-pyridyl)-5-phenyl-2-pyrazinecarboxamide (92.1 mg) was dissolved in DMF (1 ml) To the solution were added 1M i-PrI solution in DMF (0.33 ml) and 0.1M t-BuOK solution in DMF (3.3 ml). The mixture was stirred at 20-30° C. for 2 hours. The reaction mixture was portioned EtOAc and water. The organic layer was separated. The aqueous layer was extracted with EtOAc. The combined organic solution was washed with brine and dried over MgSO₄. Evaporation of solvent gave oily residue. The above residue was purified by chromatography on silica gel (EtOAc only-EtOAc:MeOH=96:4, v/v) to give 3-amino-6-(1-isopropyl-6-oxo-1,6-dihydro-3-pyridyl)-5-phenyl-2-pyrazinecarboxamide (18 mg) and 3-amino-6-(6-isopropoxy-3-pyridyl)-5-phenyl-2-pyrazinecarboxamide (42 mg).

3-Amino-6-(1-isopropyl-6-oxo-1,6-dihydro-3-pyridyl)-5-phenyl-2-pyrazinecarboxamide ¹H-NMR (DMSO-d₆ δ): 0.97 (6H, d, J=6.8 Hz), 4.90 (1H, m), 6.20 (1H, d, J=9.4 Hz), 7.34-7.47 (8H, m), 7.66-7.72 (2H, m), 8.19 (1H, s) MS (ESI⁺): 350 [M+H]⁺, 372 [M+Na]⁺, IR (KBr): 3417, 1664, 1591, 1533, 1450 cm⁻¹, m.p.: 240-245° C. (EtOAc)

3-Amino-6-(6-isopropoxy-3-pyridyl)-5-phenyl-2-pyrazinecarboxamide

¹H-NMR (DMSO-d₆ δ): 1.26 (6H, d, J=6.8 Hz), 5.20 (1H, m), 6.60 (1H, d, J=8.6 Hz), 7.42 (5H, s), 7.60-7.67 (3H, m), 8.17 (2H, s) MS (ESI+): 350 [M+H]+, 372 [M+Na]+, IR (KBr): 3471, 1683, 1656, 1600, 1488 cm−1

EXAMPLE 7

3-Amino-6-(6-methoxy-3-pyridyl)-5-phenyl-2-pyrazinecarbonitrile (800 mg) was dissolved in dioxane and conc. HC. The solution was stirred at 80° C. for 15 hours. Dioxane was evaporated out. The reaction mixture was cooled to room temperature and concentrated in vacuo to give residue. To the residue was added 1N NaOH to adjust the pH of the aqueous mixture to 6-7. The crystals were collected by filtration, and dried in vacuo to give 3-amino-6-(6-oxo-1,6-dihydro-3-pyridyl)-5-phenyl-2-pyrazinecarboxylic acid as powder (600 mg).

$^1$H-NMR (DMSO-$d_6$ δ): 6.18 (1H, d, J=9.4 Hz), 7.25-7.65 (9H, m), 11.8 (2H, brs) MS (ESI−): 307 [M−H]−

EXAMPLE 8

3-Amino-6-(6-oxo-1,6-dihydro-3-pyridyl)-5-phenyl-2-pyrazinecarboxylic acid (154 mg) was dissolved in DMF(5 ml). To the solution were added EtI (86.1 mg) and t-BuOK (61.9 mg). The mixture was stirred at 20-30° C. for 2 hours. The reaction mixture was portioned EtOAc and water. The organic layer was separated. The aqueous layer was extracted with EtOAc. The combined organic solution was washed with brine and dried over MgSO$_4$. Evaporation of solvent gave oily residue. The above residue was purified by chromatography on silica gel (EtOAc only-EtOAc:MeOH=95:5, v/v) to give ethyl 3-amino-6-(6-oxo-1,6-dihydro-3-pyridyl)-5-phenyl-2-pyrazinecarboxylate (84 mg) and ethyl 3-amino-6-(1-ethyl-6-oxo-1,6-dihydro-3-pyridyl)-5-phenyl-2-pyrazinecarboxylate (28 mg).

Ethyl 3-amino-6-(6-oxo-1,6-dihydro-3-pyridyl)-5-phenyl-2-pyrazinecarboxylate $^1$H-NMR (DMSO-$d_6$ δ): 1.34 (3H, t, J=7.0 Hz), 4.37 (2H, q, J=7.0 Hz), 6.23 (1H, d, J=9.4 Hz), 7.19 (1H, d, J=2.4 Hz), 7.25 (1H, dd, J=2.4, 9.4 Hz), 7.40-7.52 (5H, m) MS (ESI+): 359 [M+Na]+, IR (KBr): 3400, 1697, 1614, 1434, 1130 cm−1, m.p.: 230-238° C. (EtOAc)

Ethyl 3-amino-6-(1-ethyl-6-oxo-1,6-dihydro-3-pyridyl)-5-phenyl-2-pyrazinecarboxylate $^1$H-NMR (DMSO-$d_6$ δ): 1.00 (3H, t, J=7.0 Hz), 1.34 (3H, t, J=7.0 Hz), 3.76 (2H, q, J=7.0 Hz), 4.37 (2H, q, J=7.0 Hz), 6.32 (1H, d, J=9.4 Hz), 7.32 (1H, dd, J=2.6, 9.4 Hz), 7.36-7.5 (8H, m) MS (ESI+): 365 [M+H]+, 387 [M+Na]+, IR (KBr): 3400, 1662, 1600, 1440, 1122 cm−1, m.p.: 175-179° C. (EtOAc)

EXAMPLE 9

3-Amino-6-(6-oxo-1,6-dihydro-3-pyridyl)-5-phenyl-2-pyrazinecarboxylic acid (283 mg) was dissolved in DMF (10 ml). To the solution were added i-PrI (172 mg) and t-BuOK (114 mg). The mixture was stirred at 20-30° C. for 2 hours. The reaction mixture was portioned EtOAc and water. The organic layer was separated. The aqueous layer was extracted with EtOAc. The combined organic solution was washed with brine and dried over MgSO$_4$. Evaporation of solvent gave oily residue. The above residue was purified by chromatography on silica gel (EtOAc only-EtOAc:MeOH=96:4, v/v) to give isopropyl 3-amino-6-(6-oxo-1,6-dihydro-3-pyridyl)-5-phenyl-2-pyrazinecarboxylate as yellow crystal (64 mg).

$^1$H-NMR (DMSO-$d_6$ δ): 1.35 (6H, d, J=6.2 Hz), 5.20 (1H, m), 6.23 (1H, d, J=9.4 Hz), 7.19 (1H, d, J=2.2 Hz), 7.22 (1H, dd, J=2.2, 9.4 Hz), 7.40 (5H, m), 11.6 (1H, s) MS (ESI+): 351 [M+H]+, 373 [M+Na]+, IR (KBr): 3425, 1666, 1612, 1434, 1101 cm−1, m.p.: 250-256° C. (EtOAc)

EXAMPLE 10

3-Amino-6-(6-methoxy-3-pyridyl)-5-phenyl-2-pyrazinecarbonitrile (370 mg) was dissolved in 1,2-dichloroethane (37 ml). To the solution was added 1M boron tribromide solution in CH$_2$Cl$_2$ (12.2 ml) The mixture was stirred at 80° C. for 24 hours. The mixture was cooled to 20-25° C., and portioned to EtOAc and water. The organic layer was separated. The aqueous layer was extracted with EtOAc. The combined organic layer was washed with brine, and dried over MgSO$_4$. Evaporation of solvent in vacuo gave reddish solid residue. The residue was pulverized with water, to give 3-amino-6-(6-oxo-1,6-dihydro-3-pyridyl)-5-phenyl-2-pyrazinecarbonitrile as powder (254 mg).

$^1$H-NMR (DMSO-$d_6$ δ): 6.21 (1H, d, J=9.4 Hz), 7.20-7.98 (7H, m), 11.6 (1H, s) MS (ESI+): 312 [M+Na]+, IR (KBr): 3326, 2221, 1656, 1610, 1544, 1201 cm−1, m.p.: 243-248° C. (H$_2$O)

EXAMPLE 11

3-Amino-6-(6-oxo-1,6-dihydro-3-pyridyl)-5-phenyl-2-pyrazinecarbonitrile (58 mg) was dissolved in DMF (1 ml). To the solution were added 1M MeI solution in DMF (0.22 ml) and 0.1M t-BuOK solution in DMF (2.2 ml). The mixture was stirred at 20-30° C. for 2 hours. The reaction mixture was portioned EtOAc and water. The organic layer was separated. The aqueous layer was extracted with EtOAc. The combined organic solution was washed with brine and dried over MgSO$_4$. Evaporation of solvent gave oily residue. The above residue was purified by chromatography on silica gel (EtOAc only-EtOAc:MeOH=93:7, v/v) to give 3-amino-6-(1-methyl-6-oxo-1,6-dihydro-3-pyridyl)-5-phenyl-2-pyrazinecarbonitrile, which was crystallized from EtOAc (18 mg).

$^1$H-NMR (DMSO-$d_6$ δ): 3.40 (3H, s), 6.17 (1H, d, J=9.4 Hz), 6.97 (1H, dd, J=2.6, 9.4 Hz), 7.40-7.50 (7H, m), 7.81 (1H, d, J=2.6 Hz) MS (ESI+): 304 [M+H]+, 326 [M+Na]+, IR (KBr): 3386, 2221, 1670, 1590, 1542, 1205 cm−1, m.p.: >250° C. (EtOAc)

EXAMPLE 12

3-Amino-6-(1-ethyl-6-oxo-1,6-dihydro-3-pyridyl)-5-phenyl-2-pyrazinecarbonitrile The title compound was obtained in a similar manner to that of Example 11.

$^1$H-NMR (DMSO-$d_6$ δ): 1.03 (3H, t, J=7.0 Hz), 3.79 (2H, q, J=7.0 Hz), 6.25 (1H, d, J=9.4 Hz), 7.19 (1H, dd, J=2.6, 9.4 Hz), 7.44-7.47 (7H, m), 7.58 (1H, d, J=2.6 Hz) MS (ESI+): 318 [M+H]+, 340 [M+Na]+, IR (KBr): 3180, 2221, 1657, 1587, 1535, 1203 cm−1, m.p.: 193-199° C. (IPE)

EXAMPLE 13

3-Amino-6-(6-oxo-1-propyl-1,6-dihydro-3-pyridyl)-5-phenyl-2-pyrazinecarbonitrile (17 mg)

The title compound was obtained in a similar manner to that of Example 11.

$^1$H-NMR (DMSO-$d_6$ δ): 0.71 (3H, t, J=7.4 Hz), 1.44 (2H, m), 3.73 (2H, t, J=7.2 Hz), 6.26 (1H, d, J=9.4 Hz), 7.20 (1H, dd, J=2.6, 9.4 Hz), 7.38-7.47 (7H, m), 7.54 (1H, d, J=2.6 Hz) MS (ESI⁺): 332 [M+H]⁺, 354 [M+Na]⁺, IR (KBr): 3311, 2220, 1658, 1536, 1463, 1201 cm⁻¹, m.p.: 180-183° C. (IPE)

EXAMPLE 14

3-Amino-6-(1-isopropyl-6-oxo-1,6-dihydro-3-pyridyl)-5-phenyl-2-pyrazinecarbonitrile The title compound was obtained in a similar manner to that of Example 11.

¹H-NMR (DMSO-d₆ δ): 0.94 (6H, d, J=6.8 Hz), 4.85-4.92 (1H, m), 6.35 (1H, d, J=9.4 Hz), 7.28 (1H, d, J=2.4 Hz), 7.38-7.49 (8H, m) MS (ESI⁺): 332 [M+H]⁺, 354 [M+Na]⁺, IR (KBr): 3426, 2225, 1664, 1621, 15521, 1106 cm⁻¹, m.p.: 204.5° C. (95% aq. 2-propanol)

EXAMPLE 15

3-Amino-6-(6-methoxy-3-pyridyl)-5-phenyl-2-pyrazinecarbonitrile (100 mg) was dissolved in 30% hydrogen bromide solution in ACOH (1 ml). The solution was stirred at 25-30° C. for 3 hours. To the solution was added water. The pH of the aqueous mixture was adjusted to 6-7 with 12% aq. NaOH. The crystals were precipitated. The suspension was stirred at 25-30° C. for 3 hours, and stood for 10 hours in refrigerator. The crystals was collected by filtration and dried in vacuo, to give 3-amino-6-(6-methoxy-3-pyridyl)-5-phenyl-2-pyrazinecarboxamide (92.5 mg).

¹H-NMR (DMSO-d₆ δ): 3.82 (3H, s), 6.69 (1H, d, J=6.6 Hz), 7.39 (5H, s), 7.64-7.70 (3H, m), 8.17 (2H, s) MS (ESI⁺): 322 [M+H]⁺, 344 [M+Na]⁺, IR (KBr): 3411, 3276, 1689, 1598, 1496, 1286 cm⁻¹, m.p.: 208-212° C. (H₂O)

The following 24 compounds were obtained in a similar manner to that of Example 1.

EXAMPLE 16

3-amino-6-(1-isopropyl-6-oxo-1,6-dihydro-3-pyridyl)-5-phenyl-2-pyrazinecarboxamide ¹H-NMR (DMSO-d₆ δ): 0.97 (6H, d, J=6.8 Hz), 4.90 (1H, m), 6.32 (1H, d, J=9.4 Hz), 7.34-7.46 (6H, m), 7.66-7.72 (4H, m), 8.19 (1H, s) MS (ESI⁺): 350 [M+H]⁺, 372 [M+Na]⁺, IR (KBr): 3417, 1664, 1590, 1533, 1450 cm⁻¹, m.p.: 245° C. (IPA-H₂O)

EXAMPLE 17

3-Amino-5-(2-fluorophenyl)-6-(1-isopropyl-6-oxo-1,6-dihydro-3-pyridyl)-2-pyrazinecarboxamide ¹H-NMR (DMSO-d₆ δ): 0.93 (6H, d, J=6.8 Hz), 4.89 (1H, m), 6.35 (1H, d, J=9.4 Hz), 7.22-7.81 (9H, m), 8.22 (1H, s) MS (ESI⁺): 368 [M+H]⁺, 390 [M+Na]⁺, IR (KBr): 3367, 1664, 1600, 1446, 1205 cm⁻¹, m.p.: 251.7° C. (IPA-H₂O)

EXAMPLE 18

3-Amino-5-(3-fluorophenyl)-6-(1-isopropyl-6-oxo-1,6-dihydro-3-pyridyl)-2-pyrazinecarboxamide ¹H-NMR (DMSO-d₆ δ): 1.01 (6H, d, J=6.8 Hz), 4.93 (1H, m), 6.35 (1H, d, J=9.4 Hz), 7.21-7.71 (9H, m), 8.22 (1H, s) MS (ESI⁺): 368 [M+H]⁺, 390 [M+Na]⁺, IR (KBr): 3394, 1658, 1590, 1533, 1452 cm⁻¹, m.p.: 258.8° C. (IPA-H₂O)

EXAMPLE 19

3-Amino-5-(4-fluorophenyl)-6-(1-isopropyl-6-oxo-1,6-dihydro-3-pyridyl)-2-pyrazinecarboxamide ¹H-NMR (DMSO-d₆ δ): 0.97 (6H, d, J=6.8 Hz), 4.90 (1H, m), 6.32 (1H, d, J=9.4 Hz), 7.34-7.46 (6H, m), 7.66-7.72 (3H, m), 8.19 (1H, s) MS (ESI⁺): 390 [M+Na]⁺, IR (KBr): 3293, 1660, 1583, 1450, 1153 cm⁻¹, m.p.: 235.6° C. (IPA-H₂O)

EXAMPLE 20

3-Amino-5-(2-chlorophenyl)-6-[(1-isopropyl-6-oxo-1,6-dihydro-3-pyridyl)-2-pyrazinecarboxamide ¹H-NMR (DMSO-d₆ δ): 0.90 (6H, m), 4.87 (1H, m), 6.34 (1H, d, J=9.4 Hz), 7.16 (1H, d, J=2.4 Hz), 7.48-7.68 (6H, m), 7.73 (1H, s), 7.82 (1H, dd, J=2.4, 9.4 Hz), 8.24 (1H, s) MS (ESI⁺): 384 [M+H]⁺, 406 [M+Na]⁺, IR (KBr): 3367, 1666, 1604, 1454, 1157 cm⁻¹, m.p.: 254.5° C. (IPA-H₂O)

EXAMPLE 21

3-Amino-5-(3-chlorophenyl)-6-(1-isopropyl-6-oxo-1,6-dihydro-3-pyridyl)-2-pyrazinecarboxamide ¹H-NMR (DMSO-d₆ δ): 1.01 (6H, d, J=6.8 Hz), 4.93 (1H, m), 6.35 (1H, d, J=9.4 Hz), 7.35-7.46 (5H, m), 7.49 (2H, s), 7.57-7.72 (3H, m), 8.21 (1H, s) MS (ESI⁺): 384 [M+H]⁺, 406 [M+Na]⁺, IR (KBr): 3396, 1658, 1589, 1452, 1250 cm⁻¹, m.p.: 232.6° C. (IPA-H₂O)

EXAMPLE 22

3-Amino-5-(4-chlorophenyl)-6-(1-isopropyl-6-oxo-1,6-dihydro-3-pyridyl)-2-pyrazinecarboxamide ¹H-NMR (DMSO-d₆ δ): 1.02 (6H, d, J=6.8 Hz), 4.94 (1H, m), 6.34 (1H, d, J=9.4 Hz), 7.40 (1H, d, J=2.4 Hz), 7.49 (6H, s), 7.65 (1H, dd, J=2.4, 9.4 Hz), 7.70 (1H, s), 8.21 (1H, s) MS (ESI⁺): 406 [M+Na]⁺, IR (KBr): 3278, 1664, 1587, 1450, 1093 cm⁻¹, m.p.: 246.2° C. (IPA-H₂O)

EXAMPLE 23

3-Amino-6-(1-isopropyl-6-oxo-1,6-dihydro-3-pyridyl)-5-(2-methoxyphenyl)-2-pyrazinecarboxamide ¹H-NMR (DMSO-d₆ δ): 0.89-1.05 (6H, m), 3.48 (3H, s), 4.88 (1H, m), 6.32 (1H, d, J=9.4 Hz), 6.99-7.13 (2H, m), 7.22 (1H, d, J=2.4 Hz), 7.37-7.65 (2H, m), 7.59 (2H, brs), 7.66 (1H, s), 7.75 (1H, dd, J=2.4, 9.4 Hz), 8.16 (1H, s) MS (ESI⁺): 380 [M+H]⁺, 402 [M+Na]⁺, IR (KBr): 3259, 1662, 1596, 1452, 1259 cm⁻¹, m.p.: 263.1° C. (IPA-H₂O)

EXAMPLE 24

3-Amino-6-(1-isopropyl-6-oxo-1,6-dihydro-3-pyridyl)-5-(3-methoxyphenyl)-2-pyrazinecarboxamide ¹H-NMR (DMSO-d₆ δ): 1.01 (6H, d, J=6.8 Hz), 3.71 (3H, s), 4.90 (1H, m), 6.33 (1H, d, J=9.4 Hz), 6.94-7.02 (3H, m), 7.30-7.39 (2H, m), 7.65-7.71 (3H, m), 8.19 (1H, s) MS (ESI⁺): 380 [M+H]⁺, 402 [M+Na]⁺, IR (KBr): 3442, 1660, 1581, 1444, 1268 cm⁻¹, IR (KBr): 3442, 1660, 1581, 1444, 1268 cm⁻¹, m.p.: 192.3° C. (IPA-H₂O)

EXAMPLE 25

3-Amino-6-(1-isopropyl-6-oxo-1,6-dihydro-3-pyridyl)-5-(4-methoxyphenyl)-2-pyrazinecarboxamide $^1$H-NMR (DMSO-$d_6$ δ): 1.05 (6H, d, J=6.8 Hz), 3.77 (3H, s), 4.94 (1H, m), 6.32 (1H, d, J=9.4 Hz), 6.97 (2H, d, J=8.8 Hz), 7.42 (2H, d, J=8.8 Hz), 7.45-7.64 (5H, m), 8.15 (1H, s) MS (ESI$^+$): 380 [M+H]$^+$, 402 [M+Na]$^+$, IR (KBr): 3266, 1664, 1600, 1448, 1255 cm$^{-1}$, m.p.: 243.9° C. (IPA-H$_2$O)

EXAMPLE 26

3-Amino-6-(1-isopropyl-6-oxo-1,6-dihydro-3-pyridyl)-5-[2-(trifluoromethoxy)phenyl]-2-pyrazinecarboxamide $^1$H-NMR (DMSO-$d_6$ δ): 0.90 (6H, m), 4.88 (1H, m), 6.34 (1H, d, J=9.4 Hz), 7.20 (1H, d, J=2.4 Hz), 7.34-7.39 (1H, m), 7.54-7.78 (7H, m), 8.24 (1H, s) MS (ESI$^+$): 434 [M+H]$^+$, 456 [M+Na]$^+$, IR (KBr): 3386, 1662, 1596, 1257, 1162 cm$^{-1}$, m.p.: 206.5° C. (IPA-H$_2$O)

EXAMPLE 27

3-Amino-6-(1-isopropyl-6-oxo-1,6-dihydro-3-pyridyl)-5-[3-(trifluoromethoxy)phenyl]-2-pyrazinecarboxamide $^1$H-NMR (DMSO-$d_6$ δ): 0.98 (6H, d, J=6.8 Hz), 4.88 (1H, m), 6.35 (1H, d, J=9.4 Hz), 7.37-7.81 (9H, m), 8.22 (1H, s) MS (ESI$^+$): 434 [M+H]$^+$, 456 [M+Na]$^+$, IR (KBr): 3403, 1660, 1592, 1452, 1263 cm$^{-1}$, m.p.: 265.5° C. (IPA-H$_2$O)

EXAMPLE 28

3-Amino-6-(1-isopropyl-6-oxo-1,6-dihydro-3-pyridyl)-5-[4-(trifluoromethoxy)phenyl]-2-pyrazinecarboxamide $^1$H-NMR (DMSO-$d_6$ δ): 0.98 (6H, d, J=6.8 Hz), 4.91 (1H, m), 6.37 (1H, d, J=9.4 Hz), 7.30 (1H, d, J=2.4 Hz), 7.42 (2H, d, J=8.2 Hz), 7.58 (2H, d, J=8.2 Hz), 7.70 (3H, m), 7.78 (1H, dd, J=2.4, 9.4 Hz), 8.21 (1H, s) MS (ESI$^+$): 434 [M+H]$^+$, 456 [M+Na]$^+$, IR (KBr): 3403, 1660, 1592, 1452, 1263 cm$^{-1}$, m.p.: 264.0° C. (IPA-H$_2$O)

EXAMPLE 29

3-Amino-5-(3,4-difluorophenyl)-6-(1-isopropyl-6-oxo-1,6-dihydro-3-pyridyl)-2-pyrazinecarboxamide $^1$H-NMR (DMSO-$d_6$ δ): 1.05 (6H, d, J=6.8 Hz), 4.96 (1H, m), 6.35 (1H, d, J=9.2 Hz), 7.28 (1H, d, J=6.4 Hz), 7.46-7.65 (6H, m), 7.71 (1H, s), 8.21 (1H, s) MS (ESI$^+$): 386 [M+H]$^+$, 408 [M+Na]$^+$, IR (KBr): 3382, 1662, 1602, 1444, 1191 cm$^{-1}$, m.p.: 225.8° C. (IPA-H$_2$O)

EXAMPLE 30

3-Amino-5-(3,5-difluorophenyl)-6-(1-isopropyl-6-oxo-1,6-dihydro-3-pyridyl)-2-pyrazinecarboxamide $^1$H-NMR (DMSO-$d_6$ δ): 1.05 (6H, d, J=6.8 Hz), 4.95 (1H, m), 6.37 (1H, d, J=9.4 Hz), 7.14-7.37 (3H, m), 7.46 (1H, d, J=2.4 Hz), 7.66 (1H, dd, J=2.4, 9.4 Hz)), 7.73 (3H, m), 8.23 (1H, s) MS (ESI$^+$): 408 [M+Na]$^+$, IR (KBr): 3284, 1664, 1587, 1446, 1120 cm$^{-1}$, m.p.: 248.8° C. (IPA-H$_2$O)

EXAMPLE 31

3-Amino-5-(4-cyanophenyl)-6-(1-isopropyl-6-oxo-1,6-dihydro-3-pyridyl)-2-pyrazinecarboxamide $^1$H-NMR (DMSO-$d_6$ δ): 0.98 (6H, d, J=6.8 Hz), 4.92 (1H, m), 6.35 (1H, d, J=9.4 Hz), 7.38 (1H, d, J=2.4 Hz), 7.65 (2H, d, J=8.4 Hz), 7.65-7.69 (4H, m), 7.74 (1H, s), 7.90 (1H, d, J=8.4 Hz), 8.24 (1H, s) MS (ESI$^+$): 397 [M+Na]$^+$, IR (KBr): 3432, 2223, 1671, 1606, 1450 cm$^{-1}$, m.p.: 292° C. (IPA-H$_2$O)

EXAMPLE 32

3-Amino-6-(1-isopropyl-6-oxo-1,6-dihydro-3-pyridyl)-5-phenyl-2-pyrazinecarbonitrile $^1$H-NMR (DMSO-$d_6$ δ): 0.94 (6H, d, J=6.8 Hz), 4.89 (1H, m), 6.35 (1H, d, J=9.4 Hz), 7.28 (1H, d, J=2.4 Hz), 7.39-7.49 (8H, m) MS (ESI$^+$): 332 [M+H]$^+$, 354 [M+Na]$^+$, IR (KBr): 3357, 2219, 1652, 1579, 1465, 1203 cm$^{-1}$, m.p.: 205.4° C. (IPA-H$_2$O)

EXAMPLE 33

3-Amino-5-(2-fluorophenyl)-6-(1-isopropyl-6-oxo-1,6-dihydro-3-pyridyl)-2-pyrazinecarbonitrile $^1$H-NMR (DMSO-$d_6$ δ): 0.91 (6H, d, J=6.8 Hz), 4.87 (1H, m), 6.37 (1H, d, J=9.4 Hz), 7.18-7.63 (8H, m) MS (ESI$^+$): 350 [M+H]$^+$, 372 [M+Na]$^+$, IR (KBr): 3366, 2214, 1615, 1516, 1200 cm$^{-1}$, m.p.: 210.6° C. (IPA-H$_2$O)

EXAMPLE 34

3-Amino-5-(3-fluorophenyl)-6-(1-isopropyl-6-oxo-1,6-dihydro-3-pyridyl)-2-pyrazinecarbonitrile $^1$H-NMR (DMSO-$d_6$ δ): 0.98 (6H, d, J=6.8 Hz), 4.92 (1H, m), 6.37 (1H, d, J=9.4 Hz), 7.22-7.53 (8H, m) MS (ESI$^+$): 350 [M+H]$^+$, 372 [M+Na]$^+$, IR (KBr): 3360, 2214, 1660, 1570, 1205 cm$^{-1}$, m.p.: 210.6° C. (IPA-H$_2$O)

EXAMPLE 35

3-Amino-5-(4-fluorophenyl)-6-(1-isopropyl-6-oxo-1,6-dihydro-3-pyridyl)-2-pyrazinecarbonitrile $^1$H-NMR (DMSO-$d_6$ δ): 0.98 (6H, d, J=6.8 Hz), 4.92 (1H, m), 6.37 (1H, d, J=9.4 Hz), 7.22-7.68 (8H, m) MS (ESI$^+$): 350 [M+H]$^+$, IR (KBr): 3364, 2214, 1660, 1572, 1200 cm$^{-1}$, m.p.: 207.0° C. (IPA-H$_2$O)

EXAMPLE 36

3-Amino-6-(1-isopropyl-6-oxo-1,6-dihydro-3-pyridyl)-5-(2-methoxyphenyl)-2-pyrazinecarbonitrile $^1$H-NMR (DMSO-$d_6$ δ): 0.97 (6H, brs), 3.46 (3H, s), 4.86 (1H, m), 6.34 (1H, d, J=9.4 Hz), 6.99 (1H, d, J=8.2 Hz), 7.10 (1H, t, 7.6 Hz), 7.18 (1H, d, 2.5 Hz), 7.37-7.50 (5H, m) MS (ESI$^+$): 362 [M+H]$^+$, 384 [M+Na]$^+$, IR (KBr): 3266, 2214, 1600, 1448, 1255 cm$^{-1}$, m.p.: 222.6° C. (IPA-H$_2$O)

EXAMPLE 37

3-Amino-6-(1-isopropyl-6-oxo-1,6-dihydro-3-pyridyl)-5-(3-methoxyphenyl)-2-pyrazinecarbonitrile $^1$H-NMR (DMSO-$d_6$ δ): 0.98 (6H, d, J=6.8 Hz), 3.69 (3H, s), 4.91 (1H, m), 6.35 (1H, d, J=9.4 Hz), 6.95-6.97 (1H, m), 7.00 (2H, s), 7.30-7.47 (5H, m) MS (ESI$^+$): 362 [M+H]$^+$, 384 [M+Na]$^+$, IR (KBr): 3360, 2215, 1655, 1570, 1205 cm$^{-1}$, m.p.: 192.3° C. (IPA-H$_2$O)

EXAMPLE 38

3-Amino-6-(1-isopropyl-6-oxo-1,6-dihydro-3-pyridyl)-5-(4-methoxyphenyl)-2-pyrazinecarbonitrile $^1$H-NMR (DMSO-$d_6$ δ): 1.02 (6H, d, J=6.8 Hz), 3.76 (3H, s), 4.93 (1H, m), 6.35 (1H, d, J=9.4 Hz), 6.98 (2H, d, 7.2 Hz), 7.38-7.43 (6H, m) MS (ESI$^+$): 362 [M+H]$^+$, 384 [M+Na]$^+$, IR (KBr): 3357, 2218, 1650, 1570, 1200 cm$^{-1}$, m.p.: 243.9° C. (IPA-H$_2$O)

EXAMPLE 39

3-Amino-5-(3,4-difluorophenyl)-6-(1-isopropyl-6-oxo-1,6-dihydro-3-pyridyl)-2-pyrazinecarbonitrile $^1$H-NMR (DMSO-$d_6$ δ): 1.02 (6H, d, J=6.8 Hz), 4.95 (1H, m), 6.38 (1H, d, J=9.0 Hz), 7.26 (1H, m), 7.38-7.58 (6H, m), MS (ESI$^+$): 368 [M+H]$^+$, 390 [M+Na]$^+$, IR (KBr): 3166, 2210, 1658, 1461, 1201 cm$^{-1}$, m.p.: 180° C. (IPA-H$_2$O)

EXAMPLE 40

3-Amino-5-(4-fluorophenyl)-6-(1-isopropyl-6-oxo-1,6-dihydro-3-pyridyl)-2-pyrazinecarboxamide (30 g) was suspended in dioxane (60 ml) and 2N aq. NaOH (600 ml). The mixture was heated at 90° C. with stirring for 4 hours. The above reaction mixture was cooled to 25-30° C. The pH of the suspension was adjusted to 2.5 with 35% HCl (105 ml). The precipitate was collected by filtration and washed with water and dried in vacuo at 50° C. for 15 hours to give 3-amino-5-(4-fluorophenyl)-6-(1-isopropyl-6-oxo-1,6-dihydro-3-pyridyl)-2-pyrazinecarboxylic acid as yellow powder. (29.6 g)

$^1$H-NMR (DMSO-$d_6$ δ): 1.00 (6H, d, J=6.8 Hz), 4.93 (1H, m), 6.37 (1H, d, J=9.4 Hz), 7.22-7.36 (3H, m), 7.48-7.68 (5H, m), 13.00 (1H, s)

IR (KBr): 3266, 1725, 1662, 1600, 1455 cm$^{-1}$, m.p.: 222.2° C. (IPA-H$_2$O)

EXAMPLE 41

3-Amino-5-(4-fluorophenyl)-6-(1-isopropyl-6-oxo-1,6-dihydro-3-pyridyl)-2-pyrazinecarboxylic acid (25 g) was suspended in 1,2-dichlorobenzene (125 ml). The suspension was heated at 165-170° C. with stirring for 4 hours. The reaction mixture was cooled to 20-25° C. To the cooled mixture was added IPE (250 ml). The suspension was stirred at 25-30° C. for 3 hours. The precipitate was collected by filtration and dried in vacuo. The above dried precipitate was purified by chromatography on silica gel (500 g) eluting with CHCl$_3$:MeOH (9:1, 21). Evaporation of solvent in vacuo gave yellowish crystal residue, which was recrystallized from 70% EtOH (322 ml) to give 5-[5-amino-3-(4-fluorophenyl)-2-pyrazinyl]-1-isopropyl-2(1H)-pyridone as yellowish crystal (19.4 g).

$^1$H-NMR (DMSO-$d_6$ δ): 1.00 (6H, d, J=6.8 Hz), 4.93 (1H, m), 6.33 (1H, d, J=9.2 Hz), 6.63 (2H, s), 7.17-7.26 (3H, m), 7.38-7.46 (3H, m), 7.93 (1H, s) MS (ESI$^+$): 325 [M+H]$^+$, 347 [M+Na]$^+$, IR (KBr): 3166, 1666, 1604, 1533, 1467, 1222 cm$^{-1}$, m.p.: 257.7° C. (IPA-H$_2$O)

EXAMPLE 42

A mixture of 3-amino-6-(1-isopropyl-6-oxo-1,6-dihydro-3-pyridyl)-5-phenyl-2-pyrazinecarboxylic acid (70 mg), methylamine hydrochloride (14.8 mg), 1-ethyl-3-[3'-(dimethylamino)propyl]-carbodiimide (34.1 mg), and 1-hydroxybenzotriazole (29.7 mg) in CH$_2$Cl$_2$ (0.7 ml) was stirred at 25° C. for 4 hours. Water and EtOAc were poured into the mixture. The organic layer was separated, washed with water, sat. aq. NaHCO$_3$, and brine, and dried over MgSO$_4$. The solvent was removed under reduced pressure. The residue was purified by silica-gel column chromatography (n-hexane-EtOAc then CH$_2$Cl$_2$—MeOH) and then crystallized from MeOH-IPE to give 3-amino-6-(1-isopropyl-6-oxo-1,6-dihydro-3-pyridyl)-N-methyl-5-phenyl-2-pyrazinecarboxamide (40 mg).

$^1$H-NMR (DMSO-$d_6$ δ): 0.93 (6H, d, J=6.8 Hz), 2.84 (3H, d, J=4.8 Hz), 4.89 (1H, qq, J=6.8, 6.8 Hz), 6.38 (1H, d, J=9.4 Hz), 7.26 (1H, d, J=2.5 Hz), 7.42 (5H, m), 7.62 (2H, brs), 7.79 (1H, dd, J=2.5, 9.4 Hz), 8.69 (1H, m) MS (ESI$^+$): 364 [M+H]$^+$ The following 4 compounds were obtained in a similar manner to that of Example 42.

EXAMPLE 43

3-Amino-6-(1-isopropyl-6-oxo-1,6-dihydro-3-pyridyl)-N,N-dimethyl-5-phenyl-2-pyrazinecarboxamide $^1$H-NMR (DMSO-$d_6$ δ): 0.93 (6H, d, J=6.7 Hz), 3.04 (3H, s), 3.10 (3H, s), 4.89 (1H, qq, J=6.7, 6.7 Hz), 6.36 (1H, d, J=9.4 Hz), 6.73 (2H, brs), 7.21 (1H, d, J=2.5 Hz), 7.3-7.6 (6H, m) MS (ESI$^-$): 376 [M–H]$^-$

EXAMPLE 44

5-[5-Amino-6-(4-morpholinylcarbonyl)-3-phenyl-2-pyrazinyl]-1-isopropyl-2(1H)-pyridone $^1$H-NMR (DMSO-$d_6$): 0.95 (6H, d, J=6.8 Hz), 3.63 (4H, brs), 3.70 (4H, brs), 4.86 (1H, qq, J=6.8, 6.8 Hz), 6.36 (1H, d, J=9.4 Hz), 6.78 (2H, brs), 7.24 (1H, d, J=2.4 Hz), 7.3-7.5 (6H, m) MS (ESI$^+$): 420 [M+H]$^+$

EXAMPLE 45

3-Amino-6-(1-isopropyl-6-oxo-1,6-dihydro-3-pyridyl)-5-phenyl-N-(2-pyridylmethyl)-2-pyrazinecarboxamide $^1$H-NMR (DMSO-$d_6$ δ): 0.94 (6H, d, J=6.8 Hz), 4.64 (2H, d, J=6.0 Hz), 4.87 (1H, qq, J=6.8, 6.8 Hz), 6.39 (1H, d, J=9.4 Hz), 7.1-7.9 (12H, m), 8.52 (1H, distorted d, J=4.1 Hz), 9.37 (1H, t, J=6.0 Hz) MS (ESI$^+$): 441 [M+H]$^+$

EXAMPLE 46

3-Amino-N-(cyanomethyl)-6-(1-isopropyl-6-oxo-1,6-dihydro-3-pyridyl)-5-phenyl-2-pyrazinecarboxamide $^1$H-NMR (DMSO-$d_6$ δ): 0.92 (6H, d, J=6.8 Hz), 4.34 (2H, d, J=5.9 Hz), 4.88 (1H, qq, J=6.8, 6.8 Hz), 6.41 (1H, d, J=9.4 Hz), 7.24 (1H, d, J=2.4 Hz), 7.3-7.5 (5H, m), 7.61 (2H, brs), 7.83 (1H, dd, J=2.4, 9.4 Hz), 9.27 (1H, brt, J=5.9 Hz) MS (ESI$^+$): 389 [M+H]$^+$, 411 [M+Na]$^+$

EXAMPLE 47

To a mixture of 3-amino-6-(1-isopropyl-6-oxo-1,6-dihydro-3-pyridyl)-5-phenyl-2-pyrazinecarboxylic acid (70 mg) and NEt$_3$ (40.4 mg) in THF (0.7 ml), was added isobutyl chloroformate (32.7 mg) under ice-bath cooling. After 1.5 hours stirring at the same temperature, the mixture was poured into a mixture of sodium borohydride (30.2 mg) in a mixture of THF (0.7 ml) and water (1.4 ml) under ice-bath cooling. After 2.5 hours stirring at the same temperature, the mixture was diluted with water and EtOAc, and then the organic layer was separated, washed with water and brine, and dried over MgSO$_4$. The solvent was removed under reduced pressure. The residue was purified by silica-gel column chromatography (CH$_2$:Cl$_2$:MeOH=25:1-10:1). A desired fraction was triturated with IPE to give 5-[5-amino-6-(hydroxymethyl)-3-phenyl-2-pyrazinyl]-1-isopropyl-2(1H)-pyridone (24 mg).

$^1$H-NMR (DMSO-d$_6$ δ): 0.95 (6H, d, J=6.8 Hz), 4.59 (2H, d, J=5.6 Hz), 4.90 (1H, qq, J=6.8, 6.8 Hz), 5.34 (1H, t, J=5.6 Hz), 6.3-6.4 (3H, m), 7.20 (1H, d, J=2.4 Hz), 7.2-7.5 (5H, m), 7.50 (1H, dd, J=2.4, 9.4 Hz) MS (ESI$^+$): 337 [M+H]$^+$, 359 [M+Na]$^+$

The following 3 compounds were obtained in a similar manner to that of Example 42.

EXAMPLE 48

5-[5-Amino-6-(1-azetidinylcarbonyl)-3-phenyl-2-pyrazinyl]-1-isopropyl-2(1H)-pyridone $^1$H-NMR (DMSO-d$_6$ δ): 0.92 (6H, d, J=6.8 Hz), 2.25 (2H, m), 4.09 (2H, t, J=7.6 Hz), 4.70 (2H, t, J=7.6 Hz), 4.91 (1H, qq, J=6.8, 6.8 Hz), 6.36 (1H, d, J=9.4 Hz), 7.29 (1H, d, J=2.4 Hz), 7.3-7.6 (6H, m), 7.62 (2H, brs) MS (ESI$^+$): 390 [M+H]$^+$

EXAMPLE 49

3-Amino-N-(2-hydroxyethyl)-6-(1-isopropyl-6-oxo-1,6-dihydro-3-pyridyl)-5-phenyl-2-pyrazinecarboxamide $^1$H-NMR (DMSO-d$_6$ δ): 0.93 (6H, d, J=6.8 Hz), 3.4-3.5 (2H, m), 3.5-3.6 (2H, m), 4.7-5.0 (2H, m), 6.39 (1H, d, J=9.4 Hz), 7.26 (1H, 2.4 Hz), 7.3-7.5 (5H, m), 7.63 (2H, brs), 7.75 (1H, dd, J=2.4, 9.4 Hz), 8.63 (1H, t, J=5.8 Hz) MS (ESI$^+$): 394 [M+H]$^+$, 416 [M+Na]$^+$

EXAMPLE 50

3-Amino-N-cyclopropyl-6-(1-isopropyl-6-oxo-1,6-dihydro-3-pyridyl)-5-phenyl-2-pyrazinecarboxamide $^1$H-NMR (DMSO-d$_6$ δ): 0.6-0.8 (4H, m), 0.93 (6H, d, J=6.8 Hz), 2.84 (1H, m), 4.89 (1H, qq, J=6.8, 6.8 Hz), 6.37 (1H, d, J=9.4 Hz), 7.29 (1H, d, J=2.4 Hz), 7.3-7.5 (5H, m), 7.61 (2H, brs), 7.75 (1H, dd, J=2.4, 9.4 Hz), 8.57 (1H, t, J=4.2 Hz) MS (ESI$^+$): 390 [M+H]$^+$, 412 [M+Na]$^+$

EXAMPLE 51

3-Amino-6-(1-isopropyl-6-oxo-1,6-dihydro-3-pyridyl)-5-phenyl-2-pyrazinecarboxylic acid The title compound was obtained in a similar manner to that of Example 40.

$^1$H-NMR (DMSO-d$_6$ δ): 0.95 (6H, d, J=6.8 Hz), 4.90 (1H, qq, J=6.8, 6.8 Hz), 6.37 (1H, d, J=9.4 Hz), 7.31 (1H, d, J=2.4 Hz), 7.2-7.6 (7H, m), 7.59 (1H, dd, J=2.4, 9.4 Hz), 13.0 (1H, brs) MS (ESI$^-$): 349 [M−H]$^-$

EXAMPLE 52

5-(5-Amino-3-phenyl-2-pyrazinyl)-1-isopropyl-2(1H)-pyridone

The title compound was obtained in a similar manner to that of Example 41.

$^1$H-NMR (DMSO-d$_6$ δ): 0.95 (6H, d, J=6.8 Hz), 4.90 (1H, qq, J=6.8, 6.8 Hz), 6.32 (1H, d, J=9.4 Hz), 6.60 (2H, brs), 7.21 (1H, d, J=2.4 Hz), 7.2-7.5 (6H, m), 7.93 (1H, s) MS (ESI$^+$): 307 [M+H]$^+$, 329 [M+Na]$^+$

EXAMPLE 53

A mixture of 5-(5-amino-3-phenyl-2-pyrazinyl)-1-isopropyl-2(1H)-pyridone (100 mg) and N-bromosuccinimide (87.1 mg) in DMF was heated at 50° C. with stirring for 20 minutes. Sat. aq. NaHCO$_3$ and EtOAc were poured into the mixture. The organic layer was separated, washed with water and brine, and dried over MgSO$_4$. The solvent was removed under reduced pressure. The residue was purified by silica gel column chromatography (n-hexane:EtOAc=10:1-2:1). A desired product was recrystallized with IPE and dried in vacuo to give 5-(5-amino-6-bromo-3-phenyl-2-pyrazinyl)-3-bromo-1-isopropyl-2(1H)-pyridone (57 mg).

$^1$H-NMR (DMSO-d$_6$ δ): 0.94 (6H, d, J=6.8 Hz), 4.89 (1H, qq, J=6.8, 6.8 Hz), 6.97 (2H, brs), 7.24 (1H, d, J=2.4 Hz), 7.2-7.6 (5H, m), 7.92 (1H, d, J=2.4 Hz) MS (ESI$^+$): 463 [M+H]$^+$

EXAMPLE 54

3-Amino-6-(1-isopropyl-6-oxo-1,6-dihydro-3-pyridyl)-N-methoxy-N-methyl-5-phenyl-2-pyrazinecarboxamide The title compound was obtained in a similar manner to that of Example 42.

$^1$H-NMR (DMSO-d$_6$ δ): 0.94 (6H, d, J=6.8 Hz), 3.36 (3H, s), 3.75 (3H, s), 4.89 (1H, qq, J=6.8, 6.8 Hz), 6.36 (1H, d, J=9.3 Hz), 6.79 (2H, brs), 7.24 (1H, d, J=2.4 Hz), 7.3-7.6 (6H, m) MS (ESI$^+$): 394 [M+H]$^+$

EXAMPLE 55

5-(5-Amino-6-chloro-3-phenyl-2-pyrazinyl)-3-chloro-1-isopropyl-2(1H)-pyridone

The title compound was obtained in a similar manner to that of Example 53.

$^1$H-NMR (DMSO-d$_6$ δ): 0.95 (6H, d, J=6.8 Hz), 4.90 (1H, qq, J=6.8, 6.8 Hz), 7.05 (2H, brs), 7.22 (1H, d, J=2.4 Hz), 7.2-7.6 (5H, m), 7.74 (1H, d, J=2.4 Hz) MS (ESI$^+$): 375 [M+H]$^+$, 397 [M+Na]$^+$

EXAMPLE 56

5-{5-Amino-6-[(3-methoxy-1-azetidinyl)carbonyl]-3-phenyl-2-pyrazinyl}-1-isopropyl-2(1H)-pyridone The title compound was obtained in a similar manner to that of Example 1.

¹H-NMR (DMSO-d₆ δ): 1.00 (6H, d, J=6.8 Hz), 3.24 (3H, s), 3.8-4.0 (1H, m), 4.2-4.5 (2H, m), 4.4-4.6 (1H, m), 4.8-5.1 (2H, m), 6.35 (1H, J=9.2 Hz), 7.3-7.5 (7H, m), 7.62 (2H, brs) MS (ESI⁺): 420 [M+H]⁺

EXAMPLE 57

Under ice-bath cooling, to a suspension of 3-amino-6-(1-isopropyl-6-oxo-1,6-dihydro-3-pyridyl)-N-methoxy-N-methyl-5-phenyl-2-pyrazinecarboxamide (200 mg) in THF (4.0 ml) was added 3.0M solution of methylmagnesium chloride in THF (0.85 ml) dropwise. The mixture was stirred at the same temperature for 5 hours. The mixture was poured into sat. aq ammonium chloride (20 ml) and an organic layer was extracted with EtOAc (50 ml), washed with water and brine, and dried over MgSO₄. The solvent was removed under reduced pressure. The residue was purified by silica-gel column chromatography (CH₂Cl₂:MeOH=50:1-15:1). The desired fraction was recrystallized from MeOH and dried in vacuo to give 5-(6-acetyl-5-amino-3-phenyl-2-pyrazinyl)-1-isopropyl-2(1H)-pyridone (111 mg).

¹H-NMR (DMSO-d₆ δ): 0.95 (6H, d, J=6.8 Hz), 2.66 (3H, s), 4.91 (1H, qq, J=6.8, 6.8 Hz), 6.41 (1H, d, J=9.4 Hz), 7.30 (1H, d, J=2.4 Hz), 7.3-7.6 (5H, m), 7.61 (1H, dd, J=2.4, 9.4 Hz), 7.81 (2H, brs) MS (ESI⁺): 249 [M+H]⁺, 371 [M+Na]⁺

EXAMPLE 58

3-Amino-N-[2-(dimethylamino)ethyl]-6-(1-isopropyl-6-oxo-1,6-dihydro-3-pyridyl)-5-phenyl-2-pyrazinecarboxamide The title compound was obtained in a similar manner to that of Example 42.

¹H-NMR (DMSO-d₆ δ): 0.97 (6H, d, J=6.8 Hz), 2.20 (6H, s), 2.42 (2H, t, J=6.6 Hz), 3.3-3.5 (2H, m), 4.91 (1H, qq, J=6.8, 6.8 Hz), 6.37 (1H, d, J=9.4 Hz), 7.31 (1H, d, J=2.4 Hz), 7.3-7.5 (5H, m), 7.66 (1H, dd, J=2.4, 9.4 Hz), 8.62 (1H, t, J=5.7 Hz) MS (ESI⁺): 421 [M+H]⁺

EXAMPLE 59

3-Amino-6-(1-methyl-6-oxo-1,6-dihydro-3-pyridyl)-5-phenyl-2-pyrazinecarbonitrile The title compound was obtained in a similar manner to that of Example 1.

¹H-NMR (DMSO-d₆ δ): 3.40 (3H, s), 6.17 (1H, d, J=9.4 Hz), 6.97 (1H, dd, J=2.6, 9.4 Hz), 7.40-7.49 (7H, m), 7.81 (1H, d, J=2.6 Hz) MS (ESI⁺): 304 [M+H]⁺, 326 [M+Na]⁺, IR (KBr): 3386, 2221, 1670, 1590, 1542, 1205 cm⁻¹

EXAMPLE 60

A mixture of 3-amino-5-chloro-6-(1-isopropyl-6-oxo-1,6-dihydro-3-pyridyl)-2-pyrazinecarboxamide (500 mg), (4-methoxyphenyl)boronic acid (740 mg), and Pd(PPh₃)₄ (56.3 mg) in 2M aq. Na₂CO₃ (3.25 ml) and dioxane (20 ml) was refluxed for 3 hours. Water (40 ml) and of EtOAc (30 ml) were poured into the reaction mixture and the aqueous solution was extracted with EtOAc. The organic layer was washed with water and brine, and dried over MgSO₄. After filtration, the solvent was removed under reduced pressure. The residual solid was placed on a column of silica-gel and eluted with CHCl₃:MeOH (25:1). The eluent was evaporated and the residue was suspended with IPE and filtrated to give 3-amino-6-(1-isopropyl-6-oxo-1,6-dihydro-3-pyridyl)-5-(4-methoxyphenyl)-2-pyrazinecarboxamide (512 mg) as a yellow powder.

¹H-NMR (DMSO-d₆ δ): 1.05 (6H, d, J=7.0 Hz), 4.94 (1H, sept, J=7.0 Hz), 6.32 (1H, d, J=9.5 Hz), 6.98 (2H, d, J=9.0 Hz), 7.39-7.64 (7H, m), 8.15 (1H, brs) MS (ESI⁺): 380 [M+H]⁺, 421 [M+H+MeCN]⁺

The following 18 compounds were obtained in a similar manner to that of Example 60.

EXAMPLE 61

3-Amino-6-(1-isopropyl-6-oxo-1,6-dihydro-3-pyridyl)-5-(2-methoxyphenyl)-2-pyrazinecarboxamide ¹H-NMR (DMSO-d₆ δ): 0.89 (6H, brs), 3.48 (3H, s), 4.88 (1H, sept, J=6.8 Hz), 6.32 (1H, d, J=9.5 Hz), 7.00-7.13 (2H, m), 7.22 (1H, d, J=2.5 Hz), 7.37-7.79 (6H, m), 8.16 (1H, brs)

EXAMPLE 62

3-Amino-6-(1-isopropyl-6-oxo-1,6-dihydro-3-pyridyl)-5-(3-methoxyphenyl)-2-pyrazinecarboxamide ¹H-NMR (DMSO-d₆ δ): 1.00 (6H, d, J=7.0 Hz), 3.71 (3H, s), 4.92 (1H, sept, J=7.0 Hz), 6.33 (1H, d, J=9.5 Hz), 6.94-7.02 (3H, m), 7.30-7.39 (2H, m), 7.65-7.71 (4H, m), 8.20 (1H, brs)

EXAMPLE 63

3-Amino-6-(1-isopropyl-6-oxo-1,6-dihydro-3-pyridyl)-5-(2-methylphenyl)-2-pyrazinecarboxamide ¹H-NMR (DMSO-d₆ δ): 0.88 (6H, d, J=7.0 Hz), 1.99 (3H, s), 4.85 (1H, sept, J=7.0 Hz), 6.33 (1H, d, J=9.5 Hz), 7.11 (1H, d, J=2.5 Hz), 7.32 (4H, brs), 7.70 (3H, brs), 7.89 (1H, dd, J=2.5, 9.5 Hz), 8.23 (1H, brs) MS (ESI⁺): 364 [M+H]⁺, 405 [M+H+MeCN]⁺

EXAMPLE 64

3-Amino-5-(2,3-difluorophenyl)-6-(1-isopropyl-6-oxo-1,6-dihydro-3-pyridyl)-2-pyrazinecarboxamide ¹H-NMR (DMSO-d₆ δ): 0.97 (6H, d, J=7.0 Hz), 4.92 (1H, sept, J=7.0 Hz), 6.37 (1H, d, J=9.0 Hz), 7.34-7.79 (8H, m), 8.26 (1H, brs) MS (ESI⁺): 386 [M+H]⁺, 427 [M+H+MeCN]⁺

EXAMPLE 65

3-Amino-5-(2,4-difluorophenyl)-6-(1-isopropyl-6-oxo-1,6-dihydro-3-pyridyl)-2-pyrazinecarboxamide ¹H-NMR (DMSO-d₆ δ): 0.99 (6H, d, J=6.8 Hz), 4.93 (1H, sept, J=6.8 Hz), 6.36 (1H, d, J=9.0 Hz), 7.24-7.35 (3H, m), 7.65-7.77 (5H, m), 8.23 (1H, brs) MS (ESI⁺): 386 [M+H]⁺, 427 [M+H+MeCN]⁺

EXAMPLE 66

3-Amino-5-(2,5-difluorophenyl)-6-(1-isopropyl-6-oxo-1,6-dihydro-3-pyridyl)-2-pyrazinecarboxamide ¹H-NMR (DMSO-d₆ δ): 0.99 (6H, d, J=7.0 Hz), 4.92 (1H, sept, J=7.0 Hz), 6.37 (1H, d, J=9.5 Hz), 7.24-7.40 (3H, m), 7.48-7.79 (5H, m), 8.25 (1H., brs) MS (ESI⁺): 386 [M+H]⁺, 427 [M+H+MeCN]⁺

EXAMPLE 67

3-Amino-5-(2-furyl)-6-(1-isopropyl-6-oxo-1,6-dihydro-3-pyridyl)-2-pyrazinecarboxamide $^1$H-NMR (DMSO-d$_6$ δ): 1.25 (6H, d, J=6.8 Hz), 5.07 (1H, sept, J=6.8 Hz), 6.39 (1H, d, J=9.0 Hz), 6.61 (1H, dd, J=1.1, 3.5 Hz), 6.79 (1H, d, J=3.5 Hz), 7.55 (1H, dd, J=2.5, 9.5 Hz), 7.66 (3H, brs), 7.79 (2H, brs), 8.09 (1H, brs) MS (ESI$^+$): 340 [M+H]$^+$, 381 [M+H+MeCN]$^+$

EXAMPLE 68

3-Amino-5-(3-furyl)-6-(1-isopropyl-6-oxo-1,6-dihydro-3-pyridyl)-2-pyrazinecarboxamide $^1$H-NMR (DMSO-d$_6$ δ): 1.25 (6H, d, J=6.8 Hz), 5.07 (1H, sept, J=6.8 Hz), 6.39 (1H, d, J=9.0 Hz), 6.62 (1H, dd, J=2.0, 3.5 Hz), 6.79 (1H, d, J=3.5 Hz), 7.55 (1H, dd, J=2.5, 9.5 Hz), 7.66 (3H, brs), 7.99 (2H, s), 8.09 (1H, brs) MS (ESI$^+$): 340 [M+H]$^+$, 381 [M+H+MeCN]$^+$

EXAMPLE 69

3-Amino-6-(1-isopropyl-6-oxo-1,6-dihydro-3-pyridyl)-5-(2-thienyl)-2-pyrazinecarboxamide $^1$H-NMR (DMSO-d$_6$ δ): 1.23 (6H, d, J=6.8 Hz), 5.07 (1H, sept, J=6.8 Hz), 6.42 (1H, d, J=9.5 Hz), 7.04-7.06 (1H, m), 7.16-7.17 (1H, m), 7.49 (1H, d, J=2.5 Hz), 7.54 (1H, d, J=2.5 Hz), 7.65 (2H, brs), 7.69 (1H, d, J=5.5 Hz), 7.87 (1H, d, J=2.5 Hz), 8.06 (1H, brs) MS (ESI$^+$): 356 [M+H]$^+$, 397 [M+H+MeCN]$^+$

EXAMPLE 70

3-Amino-6-(1-isopropyl-6-oxo-1,6-dihydro-3-pyridyl)-5-(3-thienyl)-2-pyrazinecarboxamide $^1$H-NMR (DMSO-d$_6$ δ): 1.12 (6H, d, J=7.0 Hz), 4.98 (1H, sept, J=7.0 Hz), 6.36 (1H, d, J=9.0 Hz), 7.12 (1H, dd, J=1.3, 5.0 Hz), 7.54-7.71 (7H, m), 8.14 (1H, brs) MS (ESI$^+$): 356 [M+H]$^+$, 397 [M+H+MeCN]$^+$

EXAMPLE 71

3-Amino-6-(1-isopropyl-6-oxo-1,6-dihydro-3-pyridyl)-5-(5-methyl-2-thienyl)-2-pyrazinecarboxamide $^1$H-NMR (DMSO-d$_6$ δ): 1.26 (6H, d, J=6.5 Hz), 2.44 (3H, s), 5.08 (1H, sept, J=6.8 Hz), 6.41 (1H, d, J=9.5 Hz), 6.76 (1H, d, J=2.5 Hz), 6.98 (1H, d, J=3.5 Hz), 7.47 (1H, d, J=2.5 Hz), 7.52 (1H, d, J=2.5 Hz), 7.61 (2H, brs), 7.89 (1H, d, J=2.5 Hz), 8.01 (1H, brs) MS (ESI$^+$): 370 [M+H]$^+$, 411 [M+H+MeCN]$^+$

EXAMPLE 72

3-Amino-6-(1-isopropyl-6-oxo-1,6-dihydro-3-pyridyl)-5-(1H-pyrazol-4-yl)-2-pyrazinecarboxamide $^1$H-NMR (DMSO-d$_6$ δ): 1.23 (6H, d, J=7.0 Hz), 5.06 (1H, sept, J=7.0 Hz), 6.40 (1H, d, J=9.5 Hz), 7.50 (1H, dd, J=2.5, 9.5 Hz), 7.57 (5H, brs), 7.80 (1H, d, J=2.5 Hz), 8.01 (1H, brs), 13.06 (1H, brs) MS (ESI$^+$): 362 [M+Na]$^+$, 701[2M+Na]$^+$

EXAMPLE 73

3-Amino-6-(1-isopropyl-6-oxo-1,6-dihydro-3-pyridyl)-5-[(E)-2-phenylvinyl]-2-pyrazinecarboxamide $^1$H-NMR (DMSO-d$_6$ δ): 1.32 (6H, d, J=6.5 Hz), 5.12 (1H, sept, J=6.5 Hz), 6.50 (1H, d, J=9.5 Hz), 7.20-7.43 (5H, m), 7.59-7.83 (6H, m), 7.90 (1H, d, J=2.5 Hz), 8.10 (1H, brs) MS (ESI$^+$): 398 [M+Na]$^+$, 773[2M+Na]$^+$

EXAMPLE 74

3-Amino-6-(1-isopropyl-6-oxo-1,6-dihydro-3-pyridyl)-5-(3-pyridyl)-2-pyrazinecarboxamide $^1$H-NMR (DMSO-d$_6$ δ): 0.98 (6H, d, J=7.0 Hz), 4.93 (1H, sept, J=7.0 Hz), 6.36 (1H, d, J=9.5 Hz), 7.37-7.46 (3H, m), 7.66-7.75 (4H, m), 8.26 (1H, brs), 8.61-8.64 (2H, m) MS (ESI$^+$): 351 [M+H]$^+$, 392 [M+H+MeCN]$^+$

EXAMPLE 75

3-Amino-6-(1-isopropyl-6-oxo-1,6-dihydro-3-pyridyl)-5-(4-pyridyl)-2-pyrazinecarboxamide $^1$H-NMR (DMSO-d$_6$ δ): 1.00 (6H, d, J=7.0 Hz), 4.93 (1H, sept, J=7.0 Hz), 6.35 (1H, d, J=9.5 Hz), 7.42-7.89 (7H, m), 8.23 (1H, brs), 8.57 (1H, dd, J=2.0, 5.0 Hz), 8.64 (1H, d, J=2.0 Hz) MS (ESI$^+$): 351 [M+H]$^+$, 392 [M+H+MeCN]$^+$

EXAMPLE 76

3-Amino-5-(4-fluorophenyl)-6-(1-methyl-6-oxo-1,6-dihydro-3-pyridyl)-2-pyrazinecarboxamide $^1$H-NMR (DMSO-d$_6$ δ): 3.46 (3H, s), 6.17 (1H, d, J=9.5 Hz), 7.00 (1H, dd, J=2.5, 9.5 Hz), 7.25 (2H, t, J=9 Hz), 7.51-7.73 (5H, m), 8.15 (1H, d, J=2.5 Hz), 8.27 (1H, brs) MS (ESI$^+$): 362 [M+Na]$^+$, 701[2M+Na]$^+$

EXAMPLE 77

3-Amino-5-(2-furyl)-6-(1-methyl-6-oxo-1,6-dihydro-3-pyridyl)-2-pyrazinecarboxamide $^1$H-NMR (DMSO-d$_6$ δ): 3.50 (3H, s), 6.33 (1H, d, J=9.0 Hz), 6.63 (1H, dd, J=1.8, 3.5 Hz), 6.83 (1H, d, J=3.5 Hz), 7.28 (1H, dd, J=2.5, 9.5 Hz), 7.69-7.79 (4H, m), 8.10 (1H, d, J=2.5 Hz), 8.16 (1H, brs) MS (ESI$^+$): 334 [M+Na]$^+$

EXAMPLE 78

3-Amino-6-(1-methyl-6-oxo-1,6-dihydro-3-pyridyl)-5-(2-thienyl)-2-pyrazinecarboxamide $^1$H-NMR (DMSO-d$_6$ δ): 3.50 (3H, s), 6.35 (1H, d, J=9.5 Hz), 7.04-7.09 (1H, m), 7.19-7.21 (1H, m), 7.35 (1H, dd, J=2.5, 9.5 Hz), 7.66 (1H, brs), 7.70-7.72 (3H, m), 8.12-8.13 (2H, m) MS (ESI$^+$): 350 [M+Na]$^+$

EXAMPLE 79

A mixture of 3-amino-5-chloro-6-(1-isopropyl-6-oxo-1,6-dihydro-3-pyridyl)-2-pyrazinecarboxamide (200 mg), ethynylbenzen (331 mg), NEt$_3$ (658 mg), triphenylphosphine (17 mg), CuI (6.2 mg), and PdCl$_2$(PPh$_3$)$_2$ (23 mg) in DMF (2 ml) was heated at 80° C. for 18 hours. Water (20 ml) and EtOAc (20 ml) were poured into the reaction mixture and the aqueous solution was extracted with EtOAc. The organic layer was washed with water and brine, and dried over MgSO$_4$. After filtration, the solvent was removed under reduced pressure. The residual solid was placed on a column of silica-gel and eluted with CHCl$_3$—MeOH (97:3). The eluent was evaporated and the residue was suspended with IPE and filtrated to give 3-amino-6-(1-isopropyl-6-oxo-1,6-dihydro-3-pyridyl)-5-(phenylethynyl)-2-pyrazinecarboxamide (218 mg) as a yellow powder.

MS (ESI$^+$): 396 [M+Na]$^+$, 769[2M+Na]$^+$

EXAMPLE 80

A toluene solution of 3-amino-5-chloro-6-(1-isopropyl-6-oxo-1,6-dihydro-3-pyridyl)-2-pyrazinecarboxamide (200 mg), 2-(tributylstannyl)pyridine (311 mg), and Pd(PPh$_3$)$_4$ (22.5 mg) was refluxed for 5 hours. Water (20 ml) and EtOAc (15 ml) were poured into the reaction mixture and the aqueous solution was extracted with EtOAc. The organic layer was washed with water and brine, and dried over MgSO$_4$. After filtration, the solvent was removed under reduced pressure. The residual solid was placed on a column of silica-gel and eluted with CHCl$_3$—MeOH (97:3). The eluent was evaporated and the residue was suspended with IPE and filtrated to give 3-amino-6-(1-isopropyl-6-oxo-1,6-dihydro-3-pyridyl)-5-(2-pyridyl)-2-pyrazinecarboxamide (64 mg) as a yellow powder.

$^1$H-NMR (DMSO-d$_6$ δ): 1.01 (6H, d, J=6.5 Hz), 4.93 (1H, sept, J=6.5 Hz), 6.30 (1H, d, J=9.5 Hz), 7.35-7.46 (2H, m), 7.59-7.75 (5H, m), 7.96 (1H, dt, J=1.7, 7.8 Hz), 8.24 (1H, brs), 8.55 (1H, d, J=4.5 Hz) MS (ESI$^+$): 351 [M+H]$^+$

EXAMPLE 81

To a suspension of 3-amino-6-(1-isopropyl-6-oxo-1,6-dihydro-3-pyridyl)-5-(4-methoxyphenyl)-2-pyrazinecarboxamide (210 mg) in dioxane (2 ml) was added an aq. NaOH (2M, 4 ml) and this solution was heated at 100° C. for 4 hours. This reaction mixture was cooled to room temperature and the pH of this solution was adjusted to 2.5 with 2N aq. HCl. The precipitate was collected by filtration and washed with water to give 3-amino-6-(1-isopropyl-6-oxo-1,6-dihydro-3-pyridyl)-5-(4-methoxyphenyl)-2-pyrazinecarboxylic acid (203 mg) as a yellow powder.

$^1$H-NMR (DMSO-d$_6$): 1.03 (1H, d, J=7 Hz), 3.77 (3H, s), 4.94 (1H, sept, J=7.0 Hz), 6.36 (1H, d, J=9.5 Hz), 6.98 (2H, d, J=9.0 Hz), 7.41-7.56 (6H, m), 12.91 (1H, brs) MS (ESI$^+$): 381 [M+H]$^+$, 422 [M+H+MeCN]$^+$ The following 24 compounds were obtained in a similar manner to that of Example 81.

EXAMPLE 82

3-Amino-6-(1-isopropyl-6-oxo-1,6-dihydro-3-pyridyl)-5-(2-methoxyphenyl)-2-pyrazinecarboxylic acid $^1$H-NMR (DMSO-d$_6$ δ): 0.91 (6H, brs), 3.48 (3H, s), 4.87 (1H, sept, J=6.8 Hz), 6.35 (1H, d, J=9.5 Hz), 7.01 (1H, d, J=8 Hz), 7.10 (1H, t, J=7.5 Hz), 7.19 (1H, d, J=2.5 Hz), 7.38-7.49 (4H, m), 7.62 (1H, dd, J=2.5, 9.0 Hz), 12.93 (1H, brs) MS (ESI$^+$): 381 [M+H]$^+$, 422 [M+H+MeCN]$^+$

EXAMPLE 83

3-Amino-6-(1-isopropyl-6-oxo-1,6-dihydro-3-pyridyl)-5-(3-methoxyphenyl)-2-pyrazinecarboxylic acid $^1$H-NMR (DMSO-d$_6$ δ): 0.99 (6H, d, J=7 Hz), 3.70 (3H, s), 4.92 (1H, sept, J=7.0 Hz), 6.37 (1H, d, J=9.5 Hz), 6.95-7.04 (3H, m), 7.30-7.38 (2H, m), 7.50 (2H, brs), 7.58 (1H, dd, J=2.5, 9.0 Hz), 13 (1H, brs) MS (ESI$^+$): 381 [M+H]$^+$, 422 [M+H+MeCN]$^+$

EXAMPLE 84

3-Amino-6-(1-isopropyl-6-oxo-1,6-dihydro-3-pyridyl)-5-(2-methylphenyl)-2-pyrazinecarboxylic acid $^1$H-NMR (DMSO-d$_6$ δ): 0.88 (6H, d, J=7.0 Hz), 1.99 (3H, s), 4.85 (1H, t, J=7.0 Hz), 6.37 (1H, d, J=9.5 Hz), 7.09 (1H, d, J=2.5 Hz), 7.26-7.40 (4H, m), 7.49 (2H, brs), 7.73 (1H, dd, J=2.5, 9.5 Hz), 13.05 (1H, brs)

EXAMPLE 85

3-Amino-5-(2,3-difluorophenyl)-6-(1-isopropyl-6-oxo-1,6-dihydro-3-pyridyl)-2-pyrazinecarboxylic acid $^1$H-NMR (DMSO-d$_6$ δ): 0.95 (6H, d, J=3.5 Hz), 4.92 (1H, sept, J=3.5 Hz), 6.40 (1H, d, J=4.7 Hz), 7.30 (1H, d, J=1.1 Hz), 7.34-7.63 (6H, m), 13.20 (1H, brs) MS (ESI$^+$): 387 [M+H]$^+$, 428 [M+H+MeCN]$^+$

EXAMPLE 86

3-Amino-5-(2,4-difluorophenyl)-6-(1-isopropyl-6-oxo-1,6-dihydro-3-pyridyl)-2-pyrazinecarboxylic acid $^1$H-NMR (DMSO-d$_6$ δ): 0.97 (6H, d, J=3.4 Hz), 4.92 (1H, sept, J=3.4 Hz), 6.39 (1H, d, J=4.8 Hz), 7.26-7.33 (3H, m), 7.56 (2H, brs), 7.61 (1H, dd, J=1.3, 4.8 Hz), 7.68-7.74 (1H, m), 13.15 (1H, brs) MS (ESI$^+$): 387 [M+H]$^+$, 428 [M+H+MeCN]$^+$

EXAMPLE 87

3-Amino-5-(2,5-difluorophenyl)-6-(1-isopropyl-6-oxo-1,6-dihydro-3-pyridyl)-2-pyrazinecarboxylic acid $^1$H-NMR (DMSO-d$_6$ δ): 0.97 (6H, d, J=3.5 Hz), 4.92 (1H, sept, J=3.5 Hz), 6.4 (1H, d, J=4.8 Hz), 7.25-7.38 (3H, m), 7.51-7.55 (1H, m), 7.58 (2H, brs), 7.62 (1H, dd, J=1.3, 4.8 Hz), 13.19 (1H, brs) MS (ESI$^+$): 387 [M+H]$^+$, 428 [M+H+MeCN]$^+$

EXAMPLE 88

3-Amino-5-(2-furyl)-6-(1-isopropyl-6-oxo-1,6-dihydro-3-pyridyl)-2-pyrazinecarboxylic acid $^1$H-NMR (DMSO-d$_6$ δ): 1.24 (6H, d, J=6.5 Hz), 5.09 (1H, sept, J=6.5 Hz), 6.43 (1H, d, J=9 Hz), 6.62 (1H, dd, J=2, 3.5 Hz), 6.77 (1H, d, J=3 Hz), 7.45-7.51 (3H, m), 7.75-7.82 (2H, m)

EXAMPLE 89

3-Amino-5-(3-furyl)-6-(1-isopropyl-6-oxo-1,6-dihydro-3-pyridyl)-2-pyrazinecarboxylic acid $^1$H-NMR (DMSO-d$_6$ δ): 1.21 (6H, d, J=3.5 Hz), 5.06 (1H, sept, J=3.5 Hz), 6.43 (1H, d, J=4.8 Hz), 6.54 (1H, d, J=0.9

Hz), 7.44 (2H, brs), 7.48 (1H, dd, J=1.3, 4.8 Hz), 7.72-7.77 (3H, m), 12.95 (1H, brs) MS (ESI$^+$): 341 [M+H]$^+$, 382 [M+H+MeCN]$^+$

EXAMPLE 90

3-Amino-6-(1-isopropyl-6-oxo-1,6-dihydro-3-pyridyl)-5-(2-thienyl)-2-pyrazinecarboxylic acid $^1$H-NMR (DMSO-d$_6$ δ): 1.22 (6H, d, J=7.0 Hz), 5.08 (1H, sept, J=7.0 Hz), 6.46 (1H, d, J=9.0 Hz), 7.05-7.09 (1H, m), 7.2 (1H, dd, J=1.0, 4.0 Hz), 7.42-7.48 (3H, m), 7.73 (1H, dd, J=1.0, 5.0 Hz), 7.83 (1H, d, J=2.5 Hz), 13.00 (1H, brs) MS (ESI$^+$): 357 [M+H]$^+$, 398 [M+H+MeCN]$^+$

EXAMPLE 91

3-Amino-6-(1-isopropyl-6-oxo-1,6-dihydro-3-pyridyl)-5-(3-thienyl)-2-pyrazinecarboxylic acid $^1$H-NMR (DMSO-d$_6$ δ): 1.10 (6H, d, J=6.5 Hz), 4.98 (1H, sept, J=6.5 Hz), 6.37-6.43 (1H, m), 7.13 (1H, dd, J=11.5, 5.0 Hz), 7.46-7.60 (5H, m), 7.72 (1H, dd, J=1.3, 3 Hz) MS (ESI$^+$): 357 [M+H]$^+$, 398 [M+H+MeCN]$^+$

EXAMPLE 92

3-Amino-6-(1-isopropyl-6-oxo-1,6-dihydro-3-pyridyl)-5-(5-methyl-2-thienyl)-2-pyrazinecarboxylic acid $^1$H-NMR (DMSO-d$_6$ δ): 1.25 (6H, d, J=7.0 Hz), 5.09 (1H, sept, J=7.0 Hz), 2.44 (3H, s), 6.45 (1H, d, J=9.5 Hz), 6.77-6.78 (1H, m), 7.01 (1H, d, J=3.5 Hz), 7.40-7.46 (3H, m), 7.85 (1H, d, J=2.5 Hz), 12.98 (1H, brs) MS (ESI$^+$): 371 [M+H]$^+$, 412 [M+H+MeCN]$^+$

EXAMPLE 93

3-amino-6-(1-isopropyl-6-oxo-1,6-dihydro-3-pyridyl)-5-(1H-pyrazol-4-yl)-2-pyrazinecarboxylic acid $^1$H-NMR (DMSO-d$_6$ δ): 1.23 (1H, d, J=7.0 Hz), 5.07 (1H, sept, J=7.0 Hz), 6.44 (1H, d, J=9.0 Hz), 7.37 (2H, brs), 7.43 (1H, dd, J=2.5, 9.0 Hz), 7.66 (2H, s), 7.77 (1H, d, J=2.5 Hz), 12.99 (1H, brs) MS (ESI$^-$): 339 [M−H]$^-$

EXAMPLE 94

3-Amino-6-(1-isopropyl-6-oxo-1,6-dihydro-3-pyridyl)-5-[(E)-2-phenylvinyl]-2-pyrazinecarboxylic acid

MS (ESI$^-$): 375 [M−H]$^-$

EXAMPLE 95

3-Amino-5-(4-fluorophenyl)-6-(1-methyl-6-oxo-1,6-dihydro-3-pyridyl)-2-pyrazinecarboxylic acid $^1$H-NMR (DMSO-d$_6$ δ): 3.43 (3H, s), 6.22 (1H, d, J=9.5 Hz), 7.05 (1H, dd, J=2.8, 9.5 Hz), 7.26 (2H, t, J=8.8 Hz), 7.50 (2H, brs), 7.55 (2H, dd, J=5.5, 9.0 Hz), 7.92 (1H, d, J=2.5 Hz)

EXAMPLE 96

3-Amino-5-(2-furyl)-6-(1-methyl-6-oxo-1,6-dihydro-3-pyridyl)-2-pyrazinecarboxylic acid

MS (ESI$^-$): 311 [M−H]$^-$

EXAMPLE 97

3-Amino-6-(1-methyl-6-oxo-1,6-dihydro-3-pyridyl)-5-(2-thienyl)-2-pyrazinecarboxylic acid $^1$H-NMR (DMSO-d$_6$ δ): 3.49 (3H, s), 6.40 (1H, d, J=9.5 Hz), 7.08 (1H, dd, J=4.0, 5.0 Hz), 7.22 (1H, dd, J=1.0, 4.0 Hz), 7.36 (1H, dd, J=2.8, 9.5 Hz), 7.48 (2H, brs), 7.74 (1H, dd, J=1.0, 5.0 Hz), 7.97 (1H, d, J=2.5 Hz)

EXAMPLE 98

3-Amino-6-(1-isopropyl-6-oxo-1,6-dihydro-3-pyridyl)-5-(phenylethynyl)-2-pyrazinecarboxylic acid

MS (ESI$^-$): 373 [M−H]$^-$

EXAMPLE 99

3-Amino-5-(2-fluorophenyl)-6-(1-isopropyl-6-oxo-1,6-dihydro-3-pyridyl)-2-pyrazinecarboxylic acid $^1$H-NMR (DMSO-d$_6$ δ): 0.92 (1H, d, J=7.0 Hz), 4.88 (1H, sept, J=7.0 Hz), 6.38 (1H, d, J=9.5 Hz), 7.18-7.69 (8H, m), 13.12 (1H, brs) MS (ESI$^+$): 369 [M+H]$^+$, 410 [M+H+MeCN]$^+$

EXAMPLE 100

3-Amino-5-(3-fluorophenyl)-6-(1-isopropyl-6-oxo-1,6-dihydro-3-pyridyl)-2-pyrazinecarboxylic acid $^1$H-NMR (DMSO-d$_6$ δ): 0.99 (6H, d, J=6.5 Hz), 4.93 (1H, t, J=6.5 Hz), 6.38 (1H, d, J=9.0 Hz), 7.22-7.60 (8H, m), 13.07 (1H, brs) MS (ESI$^+$): 369 [M+H]$^+$, 410 [M+H+MeCN]$^+$

EXAMPLE 101

3-Amino-5-(3-chlorophenyl)-6-(1-isopropyl-6-oxo-1,6-dihydro-3-pyridyl)-2-pyrazinecarboxylic acid $^1$H-NMR (DMSO-d$_6$ δ): 0.99 (1H, d, J=7.0 Hz), 4.94 (1H, sept, J=7.0 Hz), 6.39 (1H, d, J=9.5 Hz), 7.37-7.62 (8H, m), 13.06 (1H, brs) MS (ESI$^+$): 385 [M+H]$^+$, 426 [M+H+MeCN]$^+$

EXAMPLE 102

3-Amino-5-(4-chlorophenyl)-6-(1-isopropyl-6-oxo-1,6-dihydro-3-pyridyl)-2-pyrazinecarboxylic acid $^1$H-NMR (DMSO-d$_6$ δ): 1.00 (6H, d, J=7.0 Hz), 4.94 (1H, t, J=7.0 Hz), 6.38 (1H, d, J=9.5 Hz), 7.34-7.59 (8H, m), 13.04 (1H, brs) MS (ESI$^+$): 385 [M+H]$^+$, 426 [M+H+MeCN]$^+$

EXAMPLE 103

3-Amino-5-(3,4-difluorophenyl)-6-(1-isopropyl-6-oxo-1,6-dihydro-3-pyridyl)-2-pyrazinecarboxylic acid $^1$H-NMR (DMSO-d$_6$ δ): 1.03 (6H, d, J=7.0 Hz), 4.96 (1H, sept, J=6.8 Hz), 6.39 (1H, d, J=9.0 Hz), 7.30-7.61 (7H, m), 13.06 (1H, brs) MS (ESI$^+$): 387 [M+H]$^+$, 428 [M+H+MeCN]$^+$

EXAMPLE 104

3-Amino-5-(3,5-difluorophenyl)-6-(1-isopropyl-6-oxo-1,6-dihydro-3-pyridyl)-2-pyrazinecarboxylic acid $^1$H-NMR (DMSO-d$_6$ δ): 1.03 (1H, d, J=6.5 Hz), 4.97 (1H, sept, J=6.5 Hz), 6.40 (1H, d, J=9.5 Hz), 7.16-7.59 (7H, m), 13.16 (1H, brs) MS (ESI$^+$): 387 [M+H]$^+$, 428 [M+H+MeCN]$^+$

EXAMPLE 105

3-Amino-6-(1-methyl-6-oxo-1,6-dihydro-3-pyridyl)-5-phenyl-2-pyrazinecarboxylic acid $^1$H-NMR (DMSO-d$_6$ δ): 3.42 (3H, s), 6.18 (1H, d, J=9.0 Hz), 7.03 (1H, dd, J=2.8, 9.0 Hz), 7.38-7.53 (7H, m), 7.91 (1H, d, J=2.5 Hz)

EXAMPLE 106

A suspension of 3-amino-6-(1-isopropyl-6-oxo-1,6-dihydro-3-pyridyl)-5-(4-methoxyphenyl)-2-pyrazinecarboxylic acid in 1,2-dichlorobenzen (3 ml) was heated at 200° C. and stirred for 4 hours. This reaction mixture was cooled to room temperature. To this solution was added IPE and stirred at room temperature for 1 hour. The precipitate was collected by filtration and washed with IPE. The residual solid was placed on a column of silica-gel and eluted with CHCl$_3$—MeOH (20:1). The eluent was evaporated and the residue was purified by recrystallization from EtOH—water to give 5-[5-amino-3-(4-methoxyphenyl)-2-pyrazinyl]-1-isopropyl-2(1H)-pyridone (88 mg) as a pale brown crystal.

$^1$H-NMR (DMSO-d$_6$ δ): 1.02 (6H, d, J=7.0 Hz), 3.75 (3H, s), 4.94 (1H, sept, J=7.0 Hz), 6.31 (1H, d, J=9.5 Hz), 6.55 (2H, brs), 6.94 (2H, d, J=9.0 Hz), 7.29-7.42 (4H, m), 7.87 (1H, s) MS (ESI$^+$): 337 [M+H]$^+$, 378 [M+H+MeCN]$^+$ The following 24 compounds were obtained in a similar manner to that of Example 106.

EXAMPLE 107

5-[5-Amino-3-(2-methoxyphenyl)-2-pyrazinyl]-1-isopropyl-2(1H)-pyridone $^1$H-NMR (DMSO-d$_6$ δ): 0.91 (6H, brs), 3.48 (3H, s), 4.87 (1H, sept, J=6.8 Hz), 6.31 (1H, d, J=9.0 Hz), 6.51 (2H, brs), 6.97-7.10 (3H, m), 7.33-7.51 (3H, m), 7.90 (1H, s) MS (ESI$^+$): 337 [M+H]$^+$, 378 [M+H+MeCN]$^+$

EXAMPLE 108

5-[5-Amino-3-(3-methoxyphenyl)-2-pyrazinyl]-1-isopropyl-2(1H)-pyridone $^1$H-NMR (DMSO-d$_6$ δ): 0.98 (6H, d, J=7.0 Hz), 3.69 (3H, s), 4.92 (1H, sept, J=7.0 Hz), 6.32 (1H, d, J=9.5 Hz), 6.61 (2H, brs), 6.89-6.95 (3H, m), 7.24-7.33 (3H, m), 7.43 (1H, dd, J=2.5, 9.5 Hz), 7.92 (1H, s)

EXAMPLE 109

5-[5-Amino-3-(2-methylphenyl)-2-pyrazinyl]-1-isopropyl-2(1H)-pyridone $^1$H-NMR (DMSO-d$_6$ δ): 0.88 (6H, d, J=6.5 Hz), 1.97 (3H, s), 4.84 (1H, sept, J=6.5 Hz), 6.32 (1H, d, J=9.0 Hz), 6.58 (2H, brs), 7.02 (1H, d, J=2.5 Hz), 7.27 (4H, brs), 7.56 (1H, dd, J=2.5, 9.0 Hz), 7.95 (1H, s)

EXAMPLE 110

5-[5-Amino-3-(2,3-difluorophenyl)-2-pyrazinyl]-1-isopropyl-2(1H)-pyridone $^1$H-NMR (DMSO-d$_6$ δ): 0.96 (6H, d, J=7 Hz), 4.91 (1H, sept, J=7 Hz), 6.36 (1H, d, J=9.5 Hz), 6.75 (2H, brs), 7.2 (1H, d, J=2.5 Hz), 7.3-7.51 (4H, m), 8.01 (1H, s) MS (ESI$^+$): 343 [M+H]$^+$, 484 [M+H+MeCN]$^+$

EXAMPLE 111

5-[5-Amino-3-(2,4-difluorophenyl)-2-pyrazinyl]-1-isopropyl-2(1H)-pyridone $^1$H-NMR (DMSO-d$_6$ δ): 0.97 (6H, d, J=7.0 Hz), 4.92 (1H, t, J=7.0 Hz), 6.35 (1H, d, J=9.0 Hz), 6.7 (2H, brs), 7.19-7.30 (3H, m), 7.47 (1H, dd, J=2.8, 9.0 Hz), 7.56-7.68 (1H, m), 7.97 (1H, s) MS (ESI$^+$): 343 [M+H]$^+$, 384 [M+H+MeCN]$^+$

EXAMPLE 112

5-[5-Amino-3-(2,5-difluorophenyl)-2-pyrazinyl]-1-isopropyl-2(1H)-pyridone $^1$H-NMR (DMSO-d$_6$ δ): 0.97 (6H, d, J=6.8 Hz), 4.91 (1H, sept, J=6.8 Hz), 6.36 (1H, d, J=9.5 Hz), 6.73 (2H, brs), 7.21-7.30 (3H, m), 7.44-7.52 (2H, m), 7.99 (1H, s) MS (ESI$^+$): 343 [M+H]$^+$, 384 [M+H+MeCN]$^+$

EXAMPLE 113

5-[5-Amino-3-(2-furyl)-2-pyrazinyl]-1-isopropyl-2(1H)-pyridone $^1$H-NMR (DMSO-d$_6$ δ): 1.22 (6H, d, J=7.0 Hz), 5.06 (1H, sept, J=7.0 Hz), 6.38 (1H, d, J=9.0 Hz), 6.56 (1H, dd, J=1.8, 3.5 Hz), 6.65-6.66 (1H, m), 7.36 (3H, dd, J=2.8, 9.5 Hz), 7.58 (2H, d, J=2.5 Hz), 7.70 (1H, m), 7.87 (1H, s) MS (ESI$^+$): 297 [M+H]$^+$, 338 [M+H+MeCN]$^+$

EXAMPLE 114

5-[5-Amino-3-(3-furyl)-2-pyrazinyl]-1-isopropyl-2(1H)-pyridone $^1$H-NMR (DMSO-d$_6$ δ): 1.19 (6H, d, J=6.5 Hz), 5.04 (1H, sept, J=6.5 Hz), 6.4 (1H, d, J=12.0 Hz), 6.42 (1H, brs), 6.54 (2H, brs), 7.39 (1H, dd, J=2.5, 9.5 Hz), 7.59 (1H, d, J=2.5 Hz), 7.65-7.69 (2H, m), 7.84 (1H, brs) MS (ESI$^+$): 297 [M+H]$^+$, 338 [M+H+MeCN]$^+$

EXAMPLE 115

5-[5-Amino-3-(2-thienyl)-2-pyrazinyl]-1-isopropyl-2(1H)-pyridone $^1$H-NMR (DMSO-d$_6$ δ): 1.20 (6H, d, J=6.5 Hz), 5.06 (1H, sept, J=6.5 Hz), 6.4 (1H, d, J=9.5 Hz), 6.63 (2H, brs), 6.99-7.04 (2H, m), 7.36 (1H, dd, J=2.5, 9.5 Hz), 7.59 (1H, dd, J=2.0, 4.5 Hz), 7.68 (1H, d, J=2.0 Hz), 7.84 (1H, s) MS (ESI$^+$): 313 [M+H]$^+$, 354 [M+H+MeCN]$^+$

EXAMPLE 116

5-[5-Amino-3-(3-thienyl)-2-pyrazinyl]-1-isopropyl-2(1H)-pyridone $^1$H-NMR (DMSO-d$_6$ δ): 1.09 (6H, d, J=6.5 Hz), 4.97 (1H, sept, J=6.5 Hz), 6.35 (1H, d, J=9.5 Hz), 6.56 (2H, brs), 7.04

(1H, dd, J=1.3, 5.0 Hz), 7.38-7.44 (2H, m), 7.51-7.58 (2H, m), 7.87 (1H, s) MS (ESI$^+$): 313 [M+H]$^+$, 354 [M+H+MeCN]$^+$

EXAMPLE 117

5-[5-Amino-3-(5-methyl-2-thienyl)-2-pyrazinyl]-1-isopropyl-2(1H)-pyridone $^1$H-NMR (DMSO-d$_6$ δ): 1.22 (6H, d, J=6.5 Hz), 2.41 (3H, s), 5.07 (1H, sept, J=6.5 Hz), 6.40 (1H, d, J=9.5 Hz), 6.57 (2H, brs), 6.69-6.70 (1H, m), 6.84 (1H, d, J=3.5 Hz), 7.35 (1H, dd, J=2.5, 9.0 Hz), 7.70 (1H, d, J=2.5 Hz), 7.79 (1H, s) MS (ESI$^+$): 327 [M+H]$^+$, 368 [M+H+MeCN]$^+$

EXAMPLE 118

5-[5-Amino-3-(1H-pyrazol-4-yl)-2-pyrazinyl]-1-isopropyl-2(1H)-pyridone $^1$H-NMR (DMSO-d$_6$ δ): 1.20 (6H, d, J=6.5 Hz), 5.05 (1H, sept, J=6.5 Hz), 6.38 (1H, d, J=9.0 Hz), 6.45 (2H, brs), 7.34 (1H, dd, J=2.5, 9.0 Hz), 7.50-7.62 (3H, m), 7.77 (1H, s), 12.92 (1H, brs) MS (ESI$^+$): 319 [M+Na]$^+$, 615[2M+Na]$^+$

EXAMPLE 119

5-{5-Amino-3-[(E)-2-phenylvinyl]-2-pyrazinyl}-1-isopropyl-2(1H)-pyridone $^1$H-NMR (DMSO-d$_6$ δ): 1.30 (6H, d, J=7.0 Hz), 5.13 (1H, sept, J=7.0 Hz), 6.49 (1H, d, J=9.5 Hz), 6.58 (2H, brs), 7.16 (1H, d, J=15.6 Hz), 7.29-7.40 (3H, m), 7.53-7.65 (4H, m), 7.74 (1H, d, J=2.0 Hz), 7.88 (1H, s) MS (ESI$^+$): 333 [M+H]$^+$, 355 [M+Na]$^+$, 687[2M+Na]$^+$

EXAMPLE 120

5-[5-Amino-3-(4-fluorophenyl)-2-pyrazinyl]-1-methyl-2(1H)-pyridone $^1$H-NMR (DMSO-d$_6$ δ): 3.40 (3H, s), 6.20 (1H, d, J=9.5 Hz), 6.62 (2H, brs), 7.01 (1H, dd, J=2.5, 9.5 Hz), 7.21 (1H, t, J=8.5 Hz), 7.46 (1H, dd, J=5.5, 8.5 Hz), 7.74 (1H, d, J=2.5 Hz), 7.90 (1H, s) MS (ESI$^+$): 297 [M+H]$^+$, 319 [M+Na]$^+$, 615[2M+Na]$^+$

EXAMPLE 121

5-[5-Amino-3-(2-furyl)-2-pyrazinyl]-1-methyl-2(1H)-pyridone $^1$H-NMR (DMSO-d$_6$ δ): 3.46 (3H, s), 6.33 (1H, d, J=9.5 Hz), 6.57 (1H, dd, J=1.5, 3.5 Hz), 6.65-6.68 (3H, m), 7.22 (1H, dd, J=2.5, 9.5 Hz), 7.69 (1H, s), 7.78 (1H, d, J=2.5 Hz), 7.85 (1H, s) MS (ESI$^+$): 269 [M+H]$^+$, 291 [M+Na]$^+$, 559 [2M+Na]$^+$

EXAMPLE 122

5-[5-Amino-3-(2-thienyl)-2-pyrazinyl]-1-methyl-2(1H)-pyridone $^1$H-NMR (DMSO-d$_6$ δ): 3.46 (3H, s), 6.36 (1H, d, J=9.5 Hz), 6.64 (2H, brs), 6.99-7.07 (2H, m), 7.28 (1H, dd, J=2.5, 9.5 Hz), 7.60 (1H, d, J=3.5 Hz), 7.82 (1H, s), 7.85 (1H, d, J=2.5 Hz) MS (ESI$^+$): 307 [M+Na]$^+$, 591[2M+Na]$^+$

EXAMPLE 123

5-[5-Amino-3-(phenylethynyl)-2-pyrazinyl]-1-isopropyl-2(1H)-pyridone $^1$H-NMR (DMSO-d$_6$ δ): 1.26 (6H, d, J=7.0 Hz), 5.06 (1H, t, J=7.0 Hz), 6.49 (1H, d, J=9.5 Hz), 6.75 (2H, brs), 7.43-7.54 (5H, m), 7.91 (1H, dd, J=2.5, 9.5 Hz), 7.95 (1H, s), 8.17 (1H, d, J=2.5 Hz) MS (ESI$^+$): 331 [M+H]$^+$, 353 [M+Na]$^+$, 683 [2M+Na]$^+$

EXAMPLE 124

5-[5-Amino-3-(2-fluorophenyl)-2-pyrazinyl]-1-isopropyl-2(1H)-pyridone $^1$H-NMR (DMSO-d$_6$ δ): 0.92 (6H, d, J=7.0 Hz), 4.88 (1H, sept, J=7.0 Hz), 6.34 (1H, d, J=9.5 Hz), 6.67 (2H, brs), 7.15-7.60 (6H, m), 7.97 (1H, s) MS (ESI$^+$): 325 [M+H]$^+$, 366 [M+H+MeCN]$^+$

EXAMPLE 125

5-[5-Amino-3-(3-fluorophenyl)-2-pyrazinyl]-1-isopropyl-2(1H)-pyridone $^1$H-NMR (DMSO-d$_6$ δ): 1.00 (6H, d, J=6.8 Hz), 4.94 (1H, sept, J=6.8 Hz), 6.35 (1H, d, J=9.0 Hz), 6.68 (2H, brs), 7.28-7.48 (6H, m), 7.95 (1H, s) MS (ESI$^+$): 341 [M+H]$^+$, 382 [M+H+MeCN]$^+$

EXAMPLE 126

5-(5-Amino-3-(3-chlorophenyl)-2-pyrazinyl]-1-isopropyl-2(1H)-pyridone $^1$H-NMR (DMSO-d$_6$ δ): 1.00 (6H, d, J=6.8 Hz), 4.94 (1H, sept, J=6.8 Hz), 6.35 (1H, d, J=9.0 Hz), 6.68 (2H, brs), 7.28-7.48 (6H, m), 7.95 (1H, s) MS (ESI$^+$): 341 [M+H]$^+$, 382 [M+H+MeCN]$^+$

EXAMPLE 127

5-[5-Amino-3-(4-chlorophenyl)-2-pyrazinyl]-1-isopropyl-2(1H)-pyridone $^1$H-NMR (DMSO-d$_6$ δ): 1.00 (6H, d, J=6.8 Hz), 4.93 (1H, sept, J=6.8 Hz), 6.34 (1H, d, J=9.5 Hz), 6.65 (2H, brs), 7.25 (1H, d, J=2.5 Hz), 7.38-7.48 (5H, m), 7.93 (1H, s) MS (ESI$^+$): 341 [M+H]$^+$, 382 [M+H+MeCN]$^+$

EXAMPLE 128

5-[5-Amino-3-(3,4-difluorophenyl)-2-pyrazinyl]-1-isopropyl-2(1H)-pyridone $^1$H-NMR (DMSO-d$_6$ δ): 1.03 (6H, d, J=6.8 Hz), 4.96 (1H, sept, J=6.8 Hz), 6.35 (1H, d, J=9.5 Hz), 6.68 (2H, brs), 7.20-7.53 (6H, m), 7.95 (1H, s) MS (ESI$^+$): 343 [M+H]$^+$, 384 [M+H+MeCN]$^+$

EXAMPLE 129

5-[5-Amino-3-(3,5-difluorophenyl)-2-pyrazinyl]-1-isopropyl-2(1H)-pyridone $^1$H-NMR (DMSO-d$_6$ δ): 1.04 (6H, d, J=6.8 Hz), 4.96 (1H, sept, J=6.8 Hz), 6.37 (1H, d, J=9.0 Hz), 6.72 (2H, brs), 7.07-7.46 (5H, m), 7.97 (1H, s) MS (ESI$^+$): 343 [M+H]$^+$, 384 [M+H+MeCN]$^+$

EXAMPLE 130

5-(5-Amino-3-phenyl-2-pyrazinyl)-1-methyl-2(1H)-pyridone $^1$H-NMR (DMSO-d$_6$ δ): 3.38 (3H, s), 6.16 (1H, d, J=4.8 Hz), 6.60 (2H, brs), 6.99 (1H, dd, J=1.4, 4.8 Hz), 7.36-7.42 (5H, m), 7.72 (1H, d, J=1.4 Hz), 7.90 (1H, s)

EXAMPLE 131

To a suspention of 3-amino-6-(1-isopropyl-6-oxo-1,6-dihydro-3-pyridyl)-5-(2-pyridyl)-2-pyrazinecarboxamide (52 mg) in dioxane (0.5 ml) was added an aq. NaOH (2M, 1 ml) and this solution was heated at 100° C. for 4 hours. This reaction mixture was cooled to room temperature and the pH of this solution was adjusted to 2.5 with 2N aq. HCl. This solution was evaporated under reduced pressure to give yellow solid. A suspension of this yellow solid in 1,2-dichlorobenzene (2 ml) was heated at 200° C. and stirred for 4 hours. This reaction mixture was cooled to room temperature. To this solution was added IPE and stirred at room temperature for 1 hour. The precipitate was collected by filtration and washed with IPE. The residual solid was placed on a column of silica-gel and eluted with CHCl$_3$—MeOH—28% aq. ammonia (15:1:0.1). The eluent was evaporated and the residue was purified by recrystallization from EtOAc-IPE to give 5-[5-amino-3-(2-pyridyl)-2-pyrazinyl]-1-isopropyl-2(1H)-pyridone (5 mg) as a pale yellow crystal.

$^1$H-NMR (DMSO-d$_6$ δ): 1.13 (6H, d, J=7.0 Hz), 5.18 (1H, t, J=7.0 Hz), 6.48 (1H, d, J=9.0 Hz), 7.29-7.38 (3H, m), 7.46 (1H, d, J=7.5 Hz), 7.75 (1H, dt, J=1.7, 7.5 Hz), 8.09 (1H, s), 8.71 (1H, d, J=4.5 Hz) MS (ESI$^+$): 308 [M+H]$^+$, 349 [M+H+MeCN]$^+$

The following 2 compounds were obtained in a similar manner to that of Example 131.

EXAMPLE 132

5-[5-Amino-3-(3-pyridyl)-2-pyrazinyl]-1-isopropyl-2(1H)-pyridone $^1$H-NMR (DMSO-d$_6$ δ): 0.98 (6H, d, J=7.0 Hz), 4.92 (1H, t, J=7.0 Hz), 6.35 (1H, d, J=9.5 Hz), 6.71 (2H, brs), 7.3 (1H, d, J=2.5 Hz), 7.38-7.46 (2H, m), 7.79 (1H, dt, J=2.5, 4.0 Hz), 7.97 (1H, s), 8.51 (1H, dd, J=1.5, 5.0 Hz), 8.56 (1H, d, J=1.5 Hz) MS (ESI$^+$): 308 [M+H]$^+$, 349 [M+H+MeCN]$^+$

EXAMPLE 133

5-[5-Amino-3-(4-pyridyl)-2-pyrazinyl]-1-isopropyl-2(1H)-pyridone $^1$H-NMR (DMSO-d$_6$ δ): 0.96 (6H, d, J=7.0 Hz), 4.92 (1H, t, J=7.0 Hz), 6.36 (1H, d, J=9.5 Hz), 6.74 (2H, brs), 7.25 (1H, d, J=2.5 Hz), 7.36-7.48 (3H, m), 7.99 (1H, brs), 8.56-8.59 (2H, m) MS (ESI$^+$): 308 [M+H]$^+$, 349 [M+H+MeCN]$^+$

EXAMPLE 134

3-Amino-5-chloro-6-(1-isopropyl-6-oxo-1,6-dihydro-3-pyridyl)-2-pyrazinecarboxamide (500 mg), (4-methoxyphenyl)boronic acid (740 mg), and Pd(PPh$_3$)$_4$ (56.3 mg) in 2M aq. Na$_2$CO$_3$ (3.25 ml) and dioxane (20 ml) was refluxed for 3 hours. Water (40 ml) and EtOAc (30 ml) were poured into the reaction mixture and the aqueous solution was extracted with EtOAc. The organic layer was washed with water and brine, and dried over MgSO$_4$. After filtration, the solvent was removed under reduced pressure. The residual solid was placed on a column of silica-gel and eluted with CHCl$_3$—MeOH (97:3). The eluent was evaporated and the residue was suspended with IPE and filtrated to give yellow powder. To a suspension of this yellow powder in dioxane (0.5 ml) was added an aq. NaOH (2M, 1 ml) and this solution was heated at 100° C. for 4 hours. This reaction mixture was cooled to room temperature and the pH of this solution was adjusted to 2.5 with 2N aq. HCl. This solution was evaporated under reduced pressure to give yellow solid. A suspension of this yellow solid in 1,2-dichlorobenzen (2 ml) was heated at 200° C. and stirred for 4 hours. This reaction mixture was cooled to room temperature. To this solution was added IPE and stirred at room temperature for 1 hour. The precipitate was collected by filtration and washed with IPE. The residual solid was placed on a column of silica-gel and eluted with CHCl$_3$—MeOH (97:3). The eluent was evaporated and the residue was purified by GPC (Gel Permeation Chromatography) to give 5-[5-amino-3-(5-chloro-2-thienyl)-2-pyrazinyl]-1-isopropyl-2(1H)-pyridone (25 mg) and 5-[5-amino-3-(5'-chloro-2,2'-bithien-5-yl)-2-pyrazinyl]-1-isopropyl-2(1H)-pyridone (26 mg) as yellow powder.

5-[5-Amino-3-(5-chloro-2-thienyl)-2-pyrazinyl]-1-isopropyl-2(1H)-pyridone $^1$H-NMR (DMSO-d$_6$ δ): 1.24 (6H, d, J=7.0 Hz), 5.08 (1H, sept, J=7.0 Hz), 6.43 (1H, d, J=9.0 Hz), 6.7 (2H, brs), 6.86 (1H, d, J=11.4 Hz), 7.02 (1H, d, J=4.0 Hz), 7.38 (1H, dd, J=2.5, 9.0 Hz), 7.77 (1H, d, J=2.5 Hz), 7.85 (1H, brs) MS (ESI$^+$): 347 [M+H]$^+$, 388 [M+H+MeCN]$^+$ 5-[5-Amino-3-(5'-chloro-2,2'-bithien-5-yl)-2-pyrazinyl]-1-isopropyl-2(1H)-pyridone $^1$H-NMR (DMSO-d$_6$ δ): 1.24 (6H, d, J=6.5 Hz), 5.09 (1H, sept, J=6.5 Hz), 6.44 (1H, d, J=9.5 Hz), 6.69 (2H, brs), 6.93 (1H, d, J=3.5 Hz), 7.12-7.21 (3H, m), 7.40 (1H, dd, J=2.5, 9.5 Hz), 7.78 (1H, d, J=2.5 Hz), 7.85 (1H, s) MS (ESI$^+$): 429 [M+H]$^+$, 470 [M+H+MeCN]$^+$

EXAMPLE 135

3-Amino-5-(4-fluorophenyl)-6-(1-isopropyl-6-oxo-1,6-dihydro-3-pyridyl)-N-methyl-2-pyrazinecarboxamide The title compound was obtained in a similar manner to that of Preparation 42.

$^1$H-NMR (DMSO-d$_6$ δ): 0.98 (6H, d, J=7.0 Hz), 2.84 (3H, d, J=5.0 Hz), 4.92 (1H, sept, J=7.0 Hz), 6.39 (1H, d, J=9.0 Hz), 7.21-7.78 (8H, m), 8.68 (1H, d, J=5.0 Hz) MS (ESI$^+$): 382 [M+H]$^+$, 404 [M+Na]$^+$, 785[2M+Na]$^+$

EXAMPLE 136

To a suspension of 3-amino-6-(1-isopropyl-6-oxo-1,6-dihydro-3-pyridyl)-5-phenyl-2-pyrazinecarboxylic acid (350 mg) in MeOH (7.0 ml), was added thionyl chloride (0.146 m) dropwise under ice-bath cooling. After 1 hour stirring at the same temperature, the mixture was allowed to warm to room temperature. The mixture was stirred for 6 hours and then refluxed with stirring for 15 hours. After cooling, the solvent was removed under reduced pressure. Water was poured into the residue and the pH of the mixture was adjusted to 10 with 1N aq. NaOH. A precipitate was isolated by filtration, washed with water, and dried in vacuo to give methyl 3-amino-6-(1-isopropyl-6-oxo-1,6-dihydro-3-pyridyl)-5-phenyl-2-pyrazinecarboxylate (244 mg).

$^1$H-NMR (DMSO-d$_6$ δ): 0.91 (6H, d, J=6.8 Hz), 3.89 (3H, s), 4.89 (1H, qq, J=6.8, 6.8 Hz), 6.41 (1H, d, J=9.3 Hz), 7.21 (1H, d, J=2.4 Hz), 7.30-7.50 (7H, m), 7.56 (1H, dd, J=2.4, 9.3 Hz) MS (ESI$^+$): 365 [M+H]$^+$, 387 [M+Na]$^+$

EXAMPLE 137

Under ice-bath cooling, methylmagnesium chloride (3M solution, 0.46 ml) was added to a suspension of methyl 3-amino-6-(1-isopropyl-6-oxo-1,6-dihydro-3-pyridyl)-5-phenyl-2-pyrazinecarboxylate (100 mg) in THF (10 ml). After 7.5 hours stirring at the same temperature, sat. aq. ammonium chloride solution (1 ml) was poured into the mixture. Water and EtOAc were poured into the mixture and the organic layer was separated, washed with water and brine, and dried over MgSO$_4$. The solvent was removed under reduced pressure. The residue was recrystallized from MeOH-IPE and dried under reduced pressure to give 5-[5-amino-6-(1-hydroxy-1-methylethyl)-3-phenyl-2-pyrazinyl]-1-isopropyl-2(1H)-pyridone (41 mg).

$^1$H-NMR (DMSO-d$_6$ δ): 0.93 (6H, d, J=6.8 Hz), 1.56 (6H, s), 4.89 (1H, qq, J=6.8, 6.8 Hz), 5.76 (1H, brs), 6.37 (1H, d, J=9.3 Hz), 6.59 (2H, brs), 7.17 (1H, d, J=2.4 Hz), 7.20-7.50 (5H, m), 7.53 (1H, dd, J=2.4, 9.3 Hz) MS (ESI$^+$): 365 [M+H]$^+$

EXAMPLE 138

To a solution of 5-(6-acetyl-5-amino-3-phenyl-2-pyrazinyl)-1-isopropyl-2(1H)-pyridone (82 mg) in THF-MeOH (1:1, 2.0 ml), was added sodium borohydride (8.9 mg). The mixture was stirred st room temperature for 4 hours. 1N HCl (0.05 ml) was poured into the mixtre. Water and EtOAc were poured into the mixture and the organic layer was separated, washed with water and brine, and dried over MgSO$_4$. The solvent was removed under reduced pressure. The residue was purified by column chromatography. The desired product was recrystallized from EtOH and dried in vacuo to give 5-[5-amino-6-(1-hydroxyethyl)-3-phenyl-2-pyrazinyl]-1-isopropyl-2(1H)-pyridone (16 mg).

$^1$H-NMR (DMSO-d$_6$ δ): 0.93 (3H, d, J=6.7 Hz), 0.94 (3H, d, J=6.7 Hz), 1.46 (3H, d, J=6.5 Hz), 4.70-5.00 (2H, m), 5.57 (1H, d, J=5.4 Hz), 6.35 (1H, d, J=9.4 Hz), 6.40 (2H, brs), 7.18 (1H, d, J=2.5 Hz), 7.40 (5H, m), 7.53 (1H, dd, J=2.5, 9.4 Hz) MS (ESI$^+$): 351 [M+H]$^+$

EXAMPLE 139

Under ice-bath cooling, NaH (60% pure, 18 mg) was added to a suspension of 5-[5-amino-6-(hydroxymethyl)-3-phenyl-2-pyrazinyl]-1-isopropyl-2(1H)-pyridone (100 mg) in DMF (1.0 ml). After 10 minute stirring, MeI (127 mg) was added to the mixture. After 10 minutes stirring at the same temperature, the mixture was allowed to warm to 25° C. After 3.5 hours stirring, EtOAc and water were poured into the mixture, and the organic layer was separated, washed with water and brine, and dried over MgSO$_4$. The solvent was removed under reduced pressure and the residue was purified by column chromatography, triturated with IPE, and dried in vacuo to give 5-[5-amino-6-(methoxymethyl)-3-phenyl-2-pyrazinyl]-1-isopropyl-2(1H)-pyridone (40 mg).

$^1$H-NMR (DMSO-d$_6$ δ): 0.93 (6H, d, J=6.7 Hz), 3.36 (3H, s), 4.53 (2H, s), 4.89 (1H, qq, J=6.7, 6.7 Hz), 6.36 (1H, d, J=9.4 Hz), 6.41 (2H, brs), 7.17 (1H, d, J=2.5 Hz), 7.2-7.5 (4H, m), 7.50 (1H, dd, J=2.5, 9.4 Hz) MS (ESI$^+$): 351 [M+H]$^+$, 373 [M+Na]$^+$

EXAMPLE 140

5-{5-Amino-6-[(benzyloxy)methyl]-3-phenyl-2-pyrazinyl}-1-isopropyl-2(1H)-pyridone The title compound was obtained in a similar manner to that of Preparation 139.

$^1$H-NMR (DMSO-d$_6$ δ): 0.93 (6H, d, J=6.8 Hz), 4.62 (2H, s), 4.67 (2H, s), 4.89 (1H, qq, J=6.8, 6.8 Hz), 6.35 (1H, d, J=9.4 Hz), 6.45 (2H, brs), 7.18 (1H, d, J=2.4 Hz), 7.20-7.40 (10H, m), 7.49 (1H, dd, J=2.4, 9.4 Hz) MS (ESI$^+$): 427 [M+H]$^+$, 449 [M+Na]$^+$

EXAMPLE 141

Under ice-bath cooling, N-bromosuccinimide (1.83 g) was added to a solution of 5-(5-amino-3-phenyl-2-pyrazinyl)-1-isopropyl-2(1H)-pyridone (3.0 g) in DMF (90 ml). The mixture was stirred at the same temperature for 2 hours. Water and CH$_2$Cl$_2$ were poured into the mixture and the organic layer was separated, washed with sat. aq. sodium thiosulfate solution, sat. aq. NaHCO$_3$ solution, water, and brine, and dried over MgSO$_4$. The solvent was removed under reduced pressure. The residue was purified by column chromatography (silica-gel, toluene-EtOAc), recrystallized from EtOH, and dried in vacuo to give 5-(5-amino-6-bromo-3-phenyl-2-pyrazinyl)-1-isopropyl-2(1H)-pyridone (3.0 g).

$^1$H-NMR (DMSO-d$_6$ δ): 0.93 (6H, d, J=6.8 Hz), 4.88 (1H, qq, J=6.8, 6.8 Hz), 6.35 (1H, d, J=9.4 Hz), 6.89 (2H, brs), 7.20 (1H, d, J=2.5 Hz), 7.30-7.50 (6H, m) MS (ESI$^+$): 385 [M+H]$^+$, 407 [M+Na]$^+$

EXAMPLE 142

To a suspension of 5-(5-amino-6-bromo-3-phenyl-2-pyrazinyl)-1-isopropyl-2(1H)-pyridone (100 mg) and Pd(PPh$_3$)$_4$ (15 mg) in THF (1.0 ml), was added a solution of methylzinc chloride in THF (2.0M, 0.75 ml). The mixture was stirred at 25° C. for 7.5 hours and then heated at 60° C. for 1.5 hours. After cooling, EtOAc and water were poured into the mixture, and the organic layer was separated, washed with water and brine, and dried over MgSO$_4$. The solvent was removed under reduced pressure. The residue was crystalized form MeOH-IPE and dried in vacuo to give 5-(5-amino-6-methyl-3-phenyl-2-pyrazinyl)-1-isopropyl-2(1H)-pyridone (95 mg).

$^1$H-NMR (DMSO-d$_6$ δ): 0.94 (0.6H, d, J=6.8 Hz), 2.38 (3H, s), 4.89 (1H, qq, J=6.8, 6.8 Hz), 6.33 (1H, d, J=9.4 Hz), 6.38 (2H, s), 7.15 (1H, d, J=2.4 Hz), 7.20-7.50 (5H, m), 7.49 (1H, dd, J=2.4, 9.4 Hz) MS (ESI$^+$): 321 [M+H]$^+$, 343 [M+Na]$^+$

EXAMPLE 143

A mixture of 5-(5-amino-6-bromo-3-phenyl-2-pyrazinyl)-1-isopropyl-2(1H)-pyridone (100 mg), phenylboronic acid (79 mg), Pd(PPh$_3$)$_4$ (9 mg), a solution of Na$_2$CO$_3$ (110 mg) in water (0.8 ml) and dioxane (2.0 ml) was heated at 90° C. with stirring for 1 hour. After cooling, EtOAc and water were poured into the mixture, and the organic layer was separated, washed with water and brine, and dried over MgSO$_4$. The solvent was removed under reduced pressure. The residue was recrystallized from MeOH-IPE and dried in vacuo to give 5-(5-amino-3,6-diphenyl-2-pyrazinyl)-1-isopropyl-2(1H)-pyridone (84 mg).

¹H-NMR (DMSO-d₆ δ): 0.94 (6H, d, J=6.8 Hz), 4.90 (1H, qq, J=6.8, 6.8 Hz), 6.30-6.40 (3H, m), 7.24 (dH, d, J=2.0 Hz), 7.30-7.70 (9H, m), 7.80-7.90 (2H, m) MS (ESI⁺): 383 [M+H]⁺, 405 [M+Na]⁺

EXAMPLE 144

5-[5-Amino-6-(2-furyl)-3-phenyl-2-pyrazinyl]-1-isopropyl-2(1H)-pyridone

The title compound was obtained in a similar manner to that of Preparation 143.

¹H-NMR (DMSO-d₆ δ): 0.95 (6H, d, J=6.8 Hz), 4.91 (1H, qq, J=6.8, 6.8 Hz), 6.38 (1H, d, J=9.4 Hz), 6.60-6.80 (3H, m), 7.19 (1H, d, J=3.4 Hz), 7.27 (1H, d, J=2.4 Hz), 7.30-7.50 (5H, m), 7.59 (1H, dd, J=2.4, 9.4 Hz), 7.89 (1H, d, J=1.1 Hz) MS (ESI⁺): 373 [M+H]⁺, 395 [M+Na]⁺

EXAMPLE 145

A mixture of 5-(5-amino-6-bromo-3-phenyl-2-pyrazinyl)-1-isopropyl-2(1H)-pyridone (100 mg), acrylamide (55 mg), Pd(OAc)₂ (3 mg), tris(2-methylphenyl)phosphine (8 mg), NEt₃ (0.11 ml), and DMF (1.0 ml) was heated with stirring at 60° C. for 1 hour and then at 90° C. for 5 hours. After cooling, EtOAc and water were poured into the mixture, and the organic layer was separated, washed with water and brine, and dried over MgSO₄. The solvent was removed under reduced pressure. The residue was recrystallized from EtOAc and dried in vacuo to give (2E)-3-[3-amino-6-(1-isopropyl-6-oxo-1,6-dihydro-3-pyridyl)-5-phenyl-2-pyrazinyl]acrylamide (70 mg).

¹H-NMR (DMSO-d₆ δ): 0.93 (6H, d, J=6.8 Hz), 4.90 (1H, qq, J=6.8, 6.8 Hz), 6.40 (1H, d, J=9.4 Hz), 6.81 (2H, brs), 7.08 (1H, d, J=14.9 Hz), 7.10-7.20 (2H, m), 7.20-7.50 (5H, m), 7.62 (1H, dd, J=2.5, 9.3 Hz), 7.70 (1H, brs), 7.75 (1H, d, J=14.9 Hz) MS (ESI⁺): 376 [M+H]⁺, 398 [M+Na]⁺

EXAMPLE 146

(2E)-3-[3-amino-6-(1-isopropyl-6-oxo-1,6-dihydro-3-pyridyl)-5-phenyl-2-pyrazinyl]-N,N-dimethylacrylamide The title compound was obtained in a similar manner to that of Preparation 145.

¹H-NMR (DMSO-d₆ δ): 0.96 (6H, d, J=6.7 Hz), 2.96 (3H, s), 3.16 (3H, s), 4.92 (1H, qq, J=6.7, 6.7 Hz), 6.36 (1H, d, J=9.4 Hz), 6.84 (2H, brs), 7.30-7.60 (8H, m), 7.79 (1H, d, J=14.6 Hz) MS (ESI⁺): 404 [M+H]⁺, 426 [M+Na]⁺

EXAMPLE 147

To a mixture of 5-(5-amino-6-bromo-3-phenyl-2-pyrazinyl)-1-isopropyl-2(1H)-pyridone (500 mg), ethynyl(trimethyl)silane (255 mg), PdCl₂(PPh₃)₂ (46 mg), CuI (12 mg), and CH₂Cl₂ (10 ml), was added NEt₃ (0.2 ml) under ice-bath cooling. The mixture was allowed to warm to 25° C. and stirred for 15 hours. Water and EtOAc were poured into the mixture, and the organic layer was separated, washed with water and brine, and dried over MgSO₄. The solvent was removed under reduced pressure. The residue was purified by column chromatography (silica-gel; CH₂Cl₂—MeOH), recrystallized from EtOH, and dried in vacuo to give 5-{5-amino-3-phenyl-6-[(trimethylsilyl)ethynyl]-2-pyrazinyl}-1-isopropyl-2(1H)-pyridone (373 mg).

¹H-NMR (DMSO-d₆ δ): 0.29 (9H, s), 0.94 (6H, d, J=6.7 Hz), 4.89 (1H, qq, J=6.7, 6.7 Hz), 6.34 (1H, d, J=9.4 Hz), 6.70 (2H, brs), 7.21 (1H, d, J=2.4 Hz), 7.30-7.50 (5H, m), 7.47 (1H, dd, J=2.5, 9.4 Hz) MS (ESI⁺): 403 [M+H]⁺, 425 [M+Na]⁺

EXAMPLE 148

A mixture of 5-{5-amino-3-phenyl-6-[(trimethylsilyl)ethynyl]-2-pyrazinyl}-1-isopropyl-2(1H)-pyridone (300 mg) and sat. K₂CO₃ in MeOH (4.5 ml) was stirred at 25° C. for 3 hours. Water and EtOAc were poured into the mixture, and the organic layer was separated, washed with water and brine, and dried over MgSO₄. The solvent was removed under reduced pressure. The residue was purified by short column (silica-gel; CH₂Cl₂) and recrystallized from EtOH to give 5-(5-amino-6-ethynyl-3-phenyl-2-pyrazinyl)-1-isopropyl-2(1H)-pyridone (100 mg).

¹H-NMR (DMSO-d₆ δ): 0.95 (6H, d, J=6.8 Hz), 4.71 (1H, s), 4.89 (1H, qq, J=6.8, 6.8 Hz), 6.34 (1H, d, J=9.3 Hz), 6.75 (2H, brs), 7.22 (1H, d, J=2.5 Hz), 7.30-7.50 (6H, m) MS (ESI⁺): 331 [M+H]⁺, 353 [M+Na]⁺

EXAMPLE 149

A mixture of 5-(5-amino-6-bromo-3-phenyl-2-pyrazinyl)-1-isopropyl-2(1H)-pyridone (100 mg), sodium methoxide (70 mg), CuI (5 mg) in NMP (1.0 ml) was heated at 100° C. for 2.5 hours. After cooling, EtOAc and water were poured into the mixture, and the organic layer was separated, washed with water and brine, and dried over MgSO₄. The solvent was removed under reduced pressure. The residue was recrystallized from MeOH-IPE to give 5-(5-amino-6-methoxy-3-phenyl-2-pyrazinyl)-1-isopropyl-2(1H)-pyridone (58 mg).

¹H-NMR (DMSO-d₆ δ): 0.94 (6H, d, J=6.7 Hz), 3.98 (3H, s), 4.90 (1H, qq, J=6.7, 6.7 Hz), 6.35 (1H, d, J=9.4 Hz), 6.49 (2H, brs), 7.19 (1H, d, J=9.4 Hz), 7.20-7.40 (5H, m), 7.52 (1H, dd, J=2.5, 9.4 Hz) MS (ESI⁺): 337 [M+H]⁺, 359 [M+Na]⁺

EXAMPLE 150

A mixture of 5-(5-amino-6-methoxy-3-phenyl-2-pyrazinyl)-1-isopropyl-2(1H)-pyridone (80 mg), conc. HCl (0.8 ml), and dioxane (1.6 ml) was heated with stirring at 100° C. for 3 hours. After cooling, the pH of the mixture was adjusted to 8 and a generated precipitate was isolated by filtration and dired in vacuo to give 5-(5-amino-6-hydroxy-3-phenyl-2-pyrazinyl)-1-isopropyl-2(1H)-pyridone (36 mg).

¹H-NMR (DMSO-d₆ δ): 1.08 (6H, d, J=6.8 Hz), 4.94 (1H, qq, J=6.8, 6.8 Hz), 6.26 (1H, d, J=9.4 Hz), 6.76 (2H, brs), 7.13 (1H, dd, J=2.2, 9.4 Hz), 7.1-7.3 (5H, m), 7.46 (1H, d, J=2.2 Hz), 11.91 (1H, brs) MS (ESI⁺): 323 [M+H]⁺, 345 [M+Na]⁺

EXAMPLE 151

To a solution of phenol (147 mg) in NMP (1.0 ml), was added 60% NaH (52 mg) under ice-bath cooling. After 5 minutes stirring, 5-(5-amino-6-bromo-3-phenyl-2-pyrazinyl)-1-isopropyl-2(1H)-pyridone (100 mg) was added to the mixture at the same temperature. And then the mixture was heated at 100° C. with stirring for 5.5 hours. After cooling, EtOAc and water were poured into the mixture, and the organic layer was separated, washed with water and brine, and dried over MgSO₄. The solvent was removed under reduced pressure. The residue was recrystallized from MeOH-IPE to give 5-(5-amino-6-phenoxy-3-phenyl-2-pyrazinyl)-1-isopropyl-2(1H)-pyridone (88 mg).

$^1$H-NMR (DMSO-$d_6$ δ): 0.90 (6H, d, J=6.8 Hz), 4.86 (1H, qq, J=6.8, 6.8 Hz), 6.23 (1H, d, J=10.1 Hz), 7.15 (2H, m), 7.20-7.50 (10H, m) MS (ESI$^+$): 399 [M+H]$^+$, 421 [M+Na]$^+$

EXAMPLE 152

A mixture of 5-(5-amino-6-bromo-3-phenyl-2-pyrazinyl)-1-isopropyl-2(1H)-pyridone (100 mg) and a solution of methylamine in THF (2.0M, 1.0 ml) was heated at 100° C. with stirring for 20 hours in a sealed tube. After cooling, the solvent was removed under reduced pressure and the residue was recrystallized from MeOH-IPE to give 5-[5-amino-6-(methylamino)-3-phenyl-2-pyrazinyl]-1-isopropyl-2(1H)-pyridone (13 mg). The filtrate was concentrated in vacuo, and the residue was rinsed with MeOH-IPE to give the desired product (60 mg).

$^1$H-NMR (DMSO-$d_6$ δ): 0.94 (6H, d, J=6.7 Hz), 2.93 (3H, d, J=4.4 Hz), 4.90 (1H, qq, J=6.7, 6.7 Hz), 6.11 (2H, brs), 6.33 (1H, d, J=9.3 Hz), 6.49 (1H, m), 7.19 (1H, d, J=2.4 Hz), 7.10-7.40 (5H, m), 7.52 (1H, dd, J=2.4, 9.4 Hz) MS (ESI$^+$): 336 [M+H]$^+$, 358 [M+Na]$^+$

EXAMPLE 153

A mixture of 5-(5-amino-6-bromo-3-phenyl-2-pyrazinyl)-1-isopropyl-2(1H)-pyridone (100 mg), morpholine (113 mg), and NMP (1.0 ml) was heated at 150° C. with stirring for 1 day. After cooling, EtOAc and water were poured into the mixture, and the organic layer was separated, washed with water and brine, and dried over MgSO$_4$. The solvent was removed under reduced pressure, and the residue was recrystallized from MeOH-IPE and dried in vacuo to give 5-[5-amino-6-(4-morpholinyl)-3-phenyl-2-pyrazinyl]-1-isopropyl-2(1H)-pyridone (84 mg).

$^1$H-NMR (DMSO-$d_6$ δ): 0.94 (6H, d, J=6.7 Hz), 3.10-3.20 (4H, m), 3.70-3.90 (4H, m), 4.90 (1H, qq, J=6.7, 6.7 Hz), 6.22 (2H, brs), 6.35 (1H, d, J=9.4 Hz), 7.19 (1H, d, J=2.4 Hz), 7.20-7.40 (5H, m), 7.54 (1H, dd, J=2.4, 9.4 Hz) MS (ESI$^+$): 392 [M+H]$^+$, 414 [M+Na]$^+$

EXAMPLE 154

A mixture of 5-(5-amino-6-bromo-3-phenyl-2-pyrazinyl)-1-isopropyl-2(1H)-pyridone (100 mg), dimethylamine hydrochloride (106 mg), N,N-diisopropylethylamine (201 mg) in NMP (1.0 ml) was heated at 150° C. with stirring for 65 hours. After cooling, EtOAc and water were poured into the mixture, and the organic layer was separated, washed with water and brine, and dried over MgSO$_4$. The solvent was removed under reduced pressure. The residue was recrystallized from MeOH-IPE and dried in vacuo to give 5-[5-amino-6-(dimethylamino)-3-phenyl-2-pyrazinyl]-1-isopropyl-2(1H)-pyridone (8 mg).

$^1$H-NMR (DMSO-$d_6$ δ): 0.94 (6H, d, J=7.0 Hz), 2.83 (6H, s), 4.90 (1H, qq, J=7.0, 7.0 Hz), 6.16 (2H, brs), 6.34 (1H, d, J=9.5 Hz), 7.20 (1H, d, J=2.5 Hz), 7.20-7.40 (5H, m), 7.54 (1H, dd, J=2.5, 9.5 Hz) MS (ESI$^+$): 350 [M+H]$^+$, 372 [M+Na]$^+$

EXAMPLE 155

To a solution of pyrazole (106 mg) in NMP (1.0 ml), was added 60% NaH (52 mg) under ice-bath cooling. After 5 minutes stirring, 5-(5-amino-6-bromo-3-phenyl-2-pyrazinyl)-1-isopropyl-2(1H)-pyridone (100 mg) was added to the mixture. And then the mixture was heated at 100° C. with stirring for 2 hours. After cooling, EtOAc and water were poured into the mixture, and the organic layer was separated, washed with water and brine, and dried over MgSO$_4$. The solvent was removed under reduced pressure, and the residue was recrystallized from MeOH and dried in vacuo to give 5-[5-amino-3-phenyl-6-(1H-pyrazol-1-yl)-2-pyrazinyl]-1-isopropyl-2(1H)-pyridone (60 mg).

$^1$H-NMR (DMSO-$d_6$ δ): 0.98 (6H, d, J=6.8 Hz), 4.92 (1H, qq, J=6.8, 6.8 Hz), 6.38 (1H, d, J=9.4 Hz), 6.68 (1H, m), 7.3-7.5 (6H, m), 7.5-7.7 (3H, m), 7.94 (1H, m), 8.78 (1H, m) MS (ESI$^-$): 371 [M–H]$^-$

EXAMPLE 156

5-[5-amino-3-phenyl-6-(1H-pyrrol-1-yl)-2-pyrazinyl]-1-isopropyl-2(1H)-pyridone

The title compound was obtained in a similar manner to that of Preparation 155.

$^1$H-NMR (DMSO-$d_6$ δ): 0.95 (6H, d, J=6.8 Hz), 4.90 (1H, qq, J=6.8, 6.8 Hz), 6.3-6.4 (3H, m), 6.49 (2H, brs), 7.28 (1H, d, J=2.4 Hz), 7.30-7.50 (7H, m), 7.53 (1H, dd, J=2.4, 9.4 Hz) MS (ESI$^+$): 372 [M+H]$^+$, 394 [M+Na]$^+$

EXAMPLE 157

To a suspension of 60% NaH (52 mg) in NMP (1.0 ml), was added thiophenol (143 mg) under ice-bath cooling. After 10 minute stirring, 5-(5-amino-6-bromo-3-phenyl-2-pyrazinyl)-1-isopropyl-2(1H)-pyridone (100 mg) was added to the mixture at the same temperature. The mixture was stirred at the same temperature for 10 minutes and then allowed to warm to 25° C. After 2 hours stirring, the mixture was heated at 100° C. for 1 hour. After cooling, EtOAc and water were poured into the mixture, and the organic layer was separated, washed with water and brine, and dried over MgSO$_4$. The solvent was removed under reduced pressure. The residue was recrystallized from MeOH-IPE to give 5-[5-amino-3-phenyl-6-(phenylthio)-2-pyrazinyl]-1-isopropyl-2(1H)-pyridone (93 mg).

$^1$H-NMR (DMSO-$d_6$ δ): 0.93 (6H, d, J=6.8 Hz), 4.87 (1H, qq, J=6.8, 6.8 Hz), 6.18 (1H, d, J=9.4 Hz), 6.62 (2H, brs), 7.06 (1H, dd, J=2.4, 9.4 Hz), 7.17 (1H, d, J=2.4 Hz), 7.3-7.5 (8H, m), 7.5-7.6 (2H, m) MS (ESI$^+$): 415 [M+H]$^+$, 437 [M+Na]$^+$

The invention claimed is:

1. A compound of formula (I):

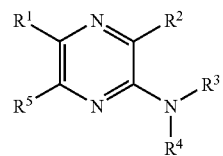

wherein
R$^1$ is

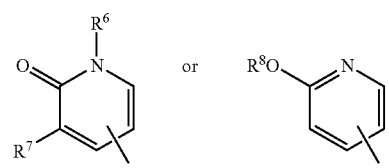

wherein
R⁶ is hydrogen, or optionally substituted lower alkyl;
R⁷ hydrogen or halogen;
R⁸ is lower alkyl;
R² is hydrogen; hydroxy; halogen; cyano; acyl; or lower alkyl, lower alkenyl, lower alkynyl, lower alkoxy, aryloxy, arylthio, aryl, heterocyclic group or amino, each of which is optionally substituted by substituent(s);
R³ and R⁴ are independently hydrogen, lower alkyl or acyl; and
R⁵ is cyano; or lower alkenyl, lower alkynyl, aryl or heterocyclic group, each of which is optionally substituted by substituent(s);
or a salt thereof.

2. The compound of claim 1, wherein
R¹ is

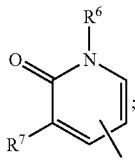

wherein
R⁶ is hydrogen, lower alkyl, aryl(lower)alkyl, heteroaryl(lower)alkyl;
R⁷ hydrogen or halogen;
R² is hydrogen, halogen, cyano, optionally substituted lower alkyl, optionally substituted lower alkynyl, lower alkoxy, aryloxy, arylthio, carbamoyl, carboxy, protected carboxy or optionally substituted amino;
R³ and R⁴ are independently hydrogen or lower alkyl; and
R⁵ is aryl or heteroaryl each of which is optionally substituted by one or more substituent(s);
or a salt thereof.

3. The compound of claim 2, wherein
R² is hydrogen, halogen, cyano, hydroxylated(lower)alkyl, lower alkynyl, lower alkoxy, aryloxy, arylthio, carboxy, esterified carboxy, carbamoyl, amidated carboxy, amino or mono- or di-(lower)alkylamino;
R³ and R⁴ are independently hydrogen;
R⁵ is aryl or heteroaryl, each of which is optionally substituted by one or more substituent(s) selected from the group consisting of halogen and lower alkoxy;
R⁶ is hydrogen or lower alkyl; and
R⁷ is hydrogen;
or a salt thereof.

4. The compound of claim 3, wherein
R² is hydrogen, bromo, cyano, hydroxymethyl, hydroxyethyl, hydroxypropyl, ethynyl, methoxy, ethoxy, propoxy, phenyloxy, phenylthio, carboxy, carbamoyl, mono- or di-methylaminocarbonyl, pyridylmethylaminocarbonyl, hydroxymethylaminocarbonyl or mono- or di-methylamino;
R³ and R⁴ are independently hydrogen;
R⁵ is phenyl, pyridyl, furyl, thienyl, pyrrolyl or pyrazolyl, each of which is optionally substituted by one or more substituent(s) selected from the group consisting of fluoro, chloro and methoxy;
R⁶ is hydrogen, methyl, ethyl, n-propyl, isopropyl, n-butyl or t-butyl; and
R⁷ is hydrogen;
or a salt thereof.

5. The compound of claim 4, wherein
R² is hydrogen, cyano, ethynyl, methoxy, phenyloxy, phenylthio, carboxy, carbamoyl or methylamino; and
R⁵ is phenyl, furyl or thienyl, each of which is optionally substituted by one or more substituent(s) selected from the group consisting of fluoro, chloro and methoxy;
or a salt thereof.

6. The compound of claim 5, wherein
R² is hydrogen, cyano, carboxy, carbamoyl or methylamino;
R⁵ is phenyl which is optionally substituted by one or more fluoro; and
R⁶ is hydrogen, methyl, ethyl or isopropyl;
or a salt thereof.

7. A process for preparing the pyrazine compound of the following formula (I):

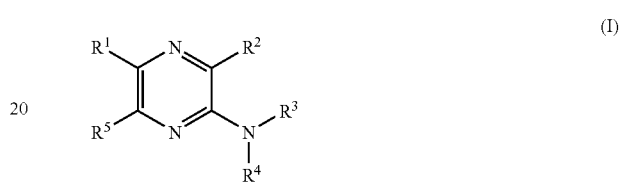

wherein
R¹ is

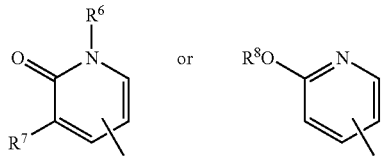

wherein
R⁶ is hydrogen, or optionally substituted lower alkyl;
R⁷ is hydrogen or halogen;
R⁸ is alkyl;
R² is hydrogen; hydroxy; halogen; cyano; acyl; or lower alkyl, lower alkenyl, lower alkynyl, lower alkoxy, aryloxy, arylthio, aryl, heterocyclic group or amino, each of which is optionally substituted by substituent(s);
R³ and R⁴ are independently hydrogen, lower alkyl or acyl; and
R⁵ is cyano; or lower alkenyl, lower alkynyl, aryl or heterocyclic group, each of which is optionally substituted by substituent(s); or a salt thereof;
which comprises
(1) reacting of a compound of the formula (II):

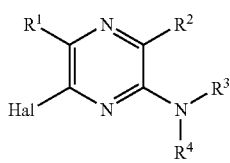

wherein R¹, R², R³ and R⁴ are each as defined above, and Hal is a halogen atom;
or a salt thereof,
with a compound of the formula (III):

R⁵-Z            (III)

wherein
R⁵ is as defined above, and
Z is hydrogen, an alkali metal (e.g. lithium, sodium, potassium, etc.), SnBu₃, BW₂ or Met-Hal;
wherein BW₂ is a part of organoboron compound; and
Met-Hal is a part of metalhalide compound;
or a salt thereof, to give a compound of the formula (I):

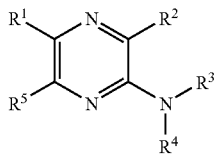
(I)

wherein $R^1$, $R^2$, $R^3$, $R^4$ and $R^5$ are each as defined above, or a salt thereof, (2) hydrolyzing of a compound of the formula (Ia)

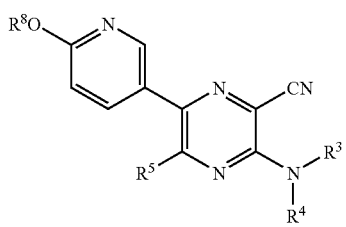
(Ia)

wherein $R^3$, $R^4$ and $R^5$ are each as defined above, and $R^8$ is as defined in claim 1, or a salt thereof, to give a compound of the formula (Iba):

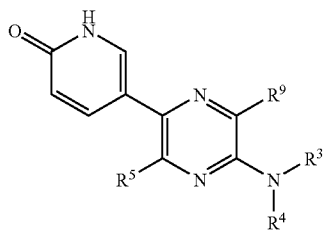
(Iba)

wherein $R^3$, $R^4$ and $R^5$ are each as defined above, and $R^9$ is cyano, carbamoyl or carboxy; or a salt thereof, (3) alkylating to a nitrogen atom of a compound of the formula (Ib):

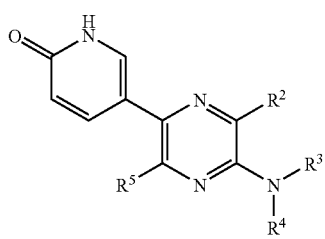
(Ib)

wherein $R^2$, $R^3$, $R^4$ and $R^5$ are each as defined above, or a salt thereof,
with a compound of the formula (IV):

$R^{10}$—Y  (IV)

wherein $R^{10}$ is lower alkyl, aryl(lower)alkyl or heteroaryl(lower)alkyl, each of which is optionally substituted by one or more suitable substituent(s), and
Y is a leaving group;
or a salt thereof,
to give a compound of the formula (Ic):

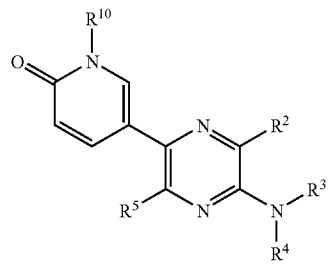
(Ic)

wherein $R^2$, $R^3$, $R^4$, $R^5$ and $R^{10}$ are each as defined above, or a salt thereof, (4) hydrolyzing of a compound of the formula (Id):

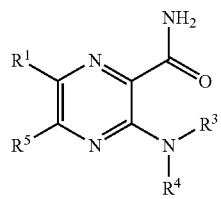
(Id)

wherein $R^1$, $R^3$, $R^4$ and $R^5$ are each as defined above, or a salt thereof,
to give a compound of the formula (Ie):

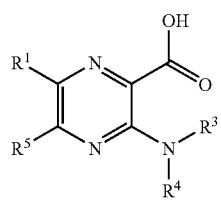
(Ie)

wherein $R^1$, $R^3$, $R^4$ and $R^5$ are each as defined above, or a salt thereof, (5) decarboxylating of a compound (Ie) or a salt thereof above to give a compound of the formula (If):

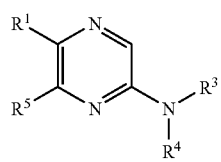
(If)

wherein $R^1$, $R^3$, $R^4$ and $R^5$ are each as defined above, or a salt thereof, (6) halogenating of a compound (If) or a salt thereof above to give a compound of the formula (Ih):

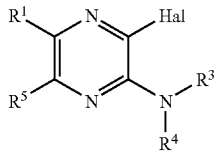 (Ih)

wherein $R^1$, $R^3$, $R^4$, $R^5$ and Hal are each as defined above, or a salt thereof, (7) reacting of a compound (Ih) or a salt thereof above with a compound of the formula (V):

$R^{13}$-Z  (V)

wherein Z is defined above, and
$R^{13}$ is lower alkyl, lower alkenyl, lower alkynyl, lower alkoxy, aryloxy, arylthio, acyl, aryl, heterocyclic group or amino, each of which is optionally substituted by substituent(s);
or a salt thereof,
to give a compound of the formula (Ij):

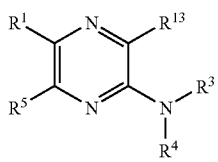 (Ij)

wherein $R^1$, $R^3$, $R^4$, $R^5$ and $R^{13}$ are each as defined above, or a salt thereof, (8) reacting of a compound of the formula (XI):

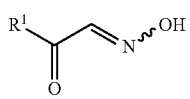 (XI)

wherein $R^1$ is as defined above, or a salt thereof, with aminomalonitrile, to give a compound of the formula (XII):

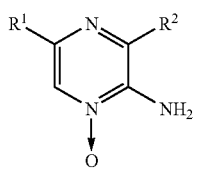 (XII)

wherein $R^1$ and $R^2$ are each as defined above, or a salt thereof, (9) halogenating of a compound of the formula (XV):

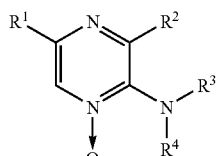 (XV)

wherein $R^1$, $R^2$, $R^3$ and $R^4$ are each as defined above, or a salt thereof,
with a compound of the formula (XVI):

PO(Hal)$_3$  (XVI)

wherein Hal is as defined above,
to give a compound (II) or a salt thereof above.

8. The process of claim 7, wherein BW$_2$ is a part of organoboron compound selected from the group consisting of B(OH)$_2$, B(CHCH$_3$CH(CH$_3$)$_2$)$_2$, tetramethyl-1,3,2-dioxaborolan-2-yl, and 9-borabicyclo[3.3.1]nonanyl.

9. The process of claim 7, wherein Met-Hal is a part of metalhalide selected from the group consisting of MgBr and ZnCl.

10. A pharmaceutical composition comprising the compound of claim 1 or a pharmaceutically acceptable salt thereof in admixture with a pharmaceutically acceptable carrier.

11. A method for treating a disease selected from the group consisting of depression, dementia, Parkinson's disease, anxiety, pain, and cerebral infarction, which comprises administering any of the compound of claim 1 or a pharmaceutically acceptable salt thereof to a human being or an animal.

12. A method for treating a disease selected from the group consisting of depression, dementia, Parkinson's disease and anxiety, which comprises administering any of the compound of claim 1 or a pharmaceutically acceptable salt thereof to a human being or an animal.

13. A method for treating Parkinson's disease, which comprises administering an effective amount of a compound of claim 1 or a pharmaceutically acceptable salt thereof to a human being or an animal in need thereof.

14. A process for preparing a pharmaceutical composition which comprises admixing the compound of claim 1 or a pharmaceutically acceptable salt thereof with a pharmaceutically acceptable carrier.

* * * * *